United States Patent
Hickey et al.

(10) Patent No.: US 12,151,044 B2
(45) Date of Patent: Nov. 26, 2024

(54) DECONTAMINATION OF GERMS ON HUMAN TOUCH POINTS

(71) Applicant: Microlumix LLC, Jacksonville, FL (US)

(72) Inventors: Christopher Eric Hickey, Jacksonville, FL (US); Debra Marie Vanderhoff, Jacksonville, FL (US)

(*) Notice: Subject to any disclaimer, the term of this patent is extended or adjusted under 35 U.S.C. 154(b) by 0 days.

(21) Appl. No.: 17/694,599

(22) Filed: Mar. 14, 2022

(65) Prior Publication Data
US 2022/0362426 A1   Nov. 17, 2022

Related U.S. Application Data

(63) Continuation-in-part of application No. 17/467,208, filed on Sep. 4, 2021, now abandoned.
(Continued)

(51) Int. Cl.
*A61L 2/24* (2006.01)
*A61L 2/10* (2006.01)

(52) U.S. Cl.
CPC ................... *A61L 2/24* (2013.01); *A61L 2/10* (2013.01); *A61L 2202/14* (2013.01)

(58) Field of Classification Search
None
See application file for complete search history.

(56) References Cited

U.S. PATENT DOCUMENTS 2,763,735 A   9/1956   Wahl
6,298,521 B1  10/2001  Butterfield
(Continued)

FOREIGN PATENT DOCUMENTS

CN   205597619 U   *   9/2016
CN   107264990 A       10/2017
(Continued)

OTHER PUBLICATIONS

Shane Thomas, Written Opinion of the International Searching Authority, Dec. 2, 2021, PCT International Searching Authority—US, Alexandria, Virginia, US, WIPO.
(Continued)

*Primary Examiner* — Andrew Smyth
(74) *Attorney, Agent, or Firm* — Dean E. Wolf, Esq.; WolfIP Law, PLLC

(57) ABSTRACT

A germ decontamination apparatus includes an enclosure including an access door configurable to be in an open or closed position, an opening for positioning the enclosure over or around a fomite, opening means for opening the access door in response to a trigger or triggering event, one or more ultraviolet light sources disposed inside the enclosure and configured to decontaminate the fomite. The germ decontamination apparatus may include one or more sensors configured to detect a triggering event. The one or more sensors may include an obstruction sensor, a motion sensor or detector, a light sensor, a sound sensor, and/or a heat or infrared sensor. The access door may include one or more access panels. The one or more ultraviolet light sources may produce UV-C radiation with a wavelength in the range of 200-280 nm. Methods of use and systems comprising the germ decontamination apparatus are also provided.

27 Claims, 47 Drawing Sheets

Related U.S. Application Data

(60) Provisional application No. 63/075,040, filed on Sep. 4, 2020.

(56) References Cited

U.S. PATENT DOCUMENTS

| | | | |
|---|---|---|---|
| 6,461,568 | B1 | 10/2002 | Eckhardt |
| 7,080,427 | B1 | 7/2006 | Campopiano et al. |
| 7,646,000 | B2 | 1/2010 | Shih |
| 7,989,779 | B1 | 8/2011 | Ray |
| 8,161,780 | B1 * | 4/2012 | Huml .................. E05B 65/1086 70/109 |
| 8,203,124 | B2 | 6/2012 | Havens |
| 8,283,639 | B2 | 10/2012 | Lane |
| 8,481,970 | B2 | 7/2013 | Cooper et al. |
| 8,598,539 | B2 | 12/2013 | Chuang |
| 9,295,741 | B2 | 3/2016 | Yerby |
| 9,808,547 | B2 | 11/2017 | Robert |
| 10,064,967 | B2 | 9/2018 | Nguyen |
| 10,092,669 | B2 | 10/2018 | Marshall |
| 10,309,124 | B2 | 6/2019 | York |
| 10,357,583 | B2 | 7/2019 | Dayton |
| 10,792,380 | B2 | 10/2020 | Schumacher |
| 10,925,983 | B2 | 2/2021 | Dayton |
| 10,994,040 | B2 | 5/2021 | Kennedy et al. |
| 11,033,645 | B1 | 6/2021 | Mora et al. |
| 11,191,857 | B2 | 12/2021 | Pangan, Jr. et al. |
| 2007/0071636 | A1 | 3/2007 | Bovino et al. |
| 2008/0067418 | A1 * | 3/2008 | Ross ...................... A61L 2/24 250/455.11 |
| 2009/0123331 | A1 * | 5/2009 | Ross ...................... A61L 2/10 422/186.3 |
| 2011/0174992 | A1 | 7/2011 | Sakita |
| 2012/0176241 | A1 | 7/2012 | Pasch et al. |
| 2012/0305804 | A1 | 12/2012 | Goldman |
| 2017/0348446 | A1 * | 12/2017 | Golden, Sr. ............... A61L 2/24 |
| 2018/0221519 | A1 * | 8/2018 | Nguyen .................. A61L 2/10 |
| 2018/0266169 | A1 * | 9/2018 | Wray ...................... E05F 15/40 |
| 2018/0266172 | A1 * | 9/2018 | Wray ...................... E05F 17/004 |
| 2018/0339075 | A1 * | 11/2018 | Kennedy ................ A61L 2/24 |
| 2019/0255206 | A1 * | 8/2019 | Wyman ................. A61L 2/0088 |
| 2019/0322546 | A1 | 10/2019 | Sugiyama et al. |
| 2020/0086477 | A1 | 3/2020 | Fulkerson |
| 2021/0330830 | A1 * | 10/2021 | Zerello ..................... A61L 2/10 |

FOREIGN PATENT DOCUMENTS

| | | | |
|---|---|---|---|
| CN | 111358204 A | | 7/2020 |
| CN | 210948047 | | 7/2020 |
| CN | 111358204 U | | 1/2021 |
| CN | 210948047 U | | 1/2021 |
| DE | 102017129860 A1 | | 6/2019 |
| EP | 2095830 A1 * | | 9/2009 ............... A61L 2/10 |
| FR | 3086543 A1 * | | 4/2020 ............... A61L 2/10 |
| IN | 202011056480 A | | 8/2021 |
| JP | 2020116430 A | | 8/2020 |
| KR | 20140005730 U * | | 11/2014 |
| PH | 2016000334 | | 4/2018 |
| WO | WO-2007136906 A2 * | | 11/2007 ............... A61L 2/10 |
| WO | 2013025894 | | 2/2013 |

OTHER PUBLICATIONS

Sun & Safe Denmark, Sun & Safe Denmark, Jan. 24, 2022, https://sunandsafe.com/uvhandle/.

* cited by examiner

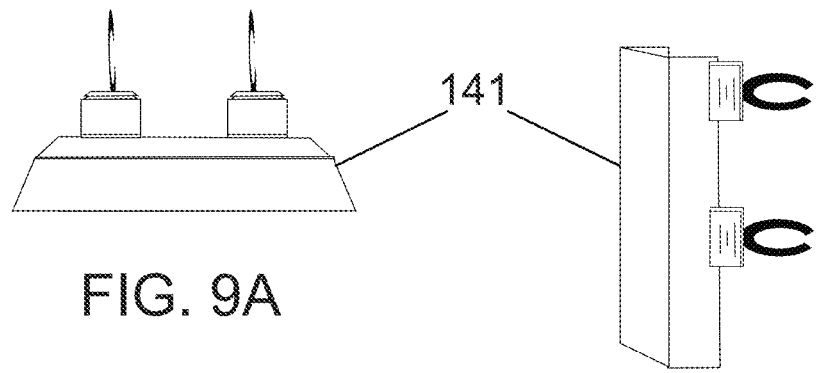
FIG. 9A
FIG. 9B
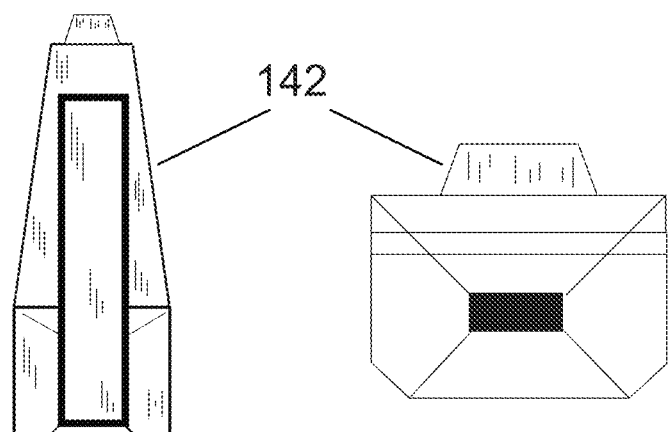
FIG. 9C
FIG. 9D

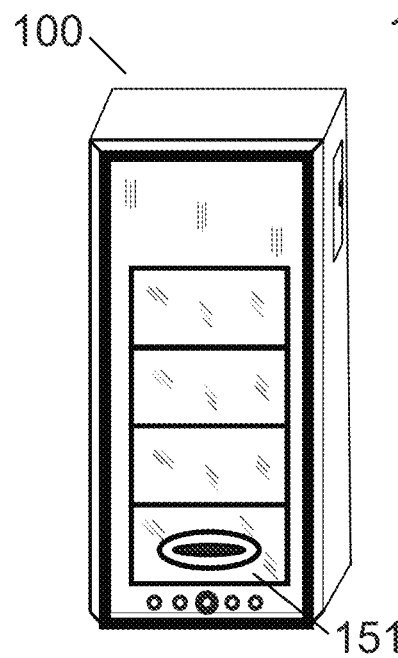
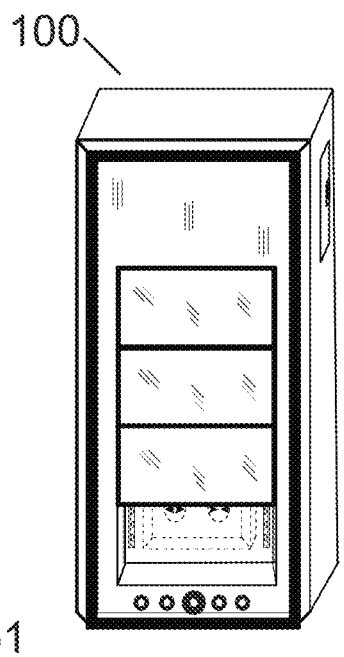
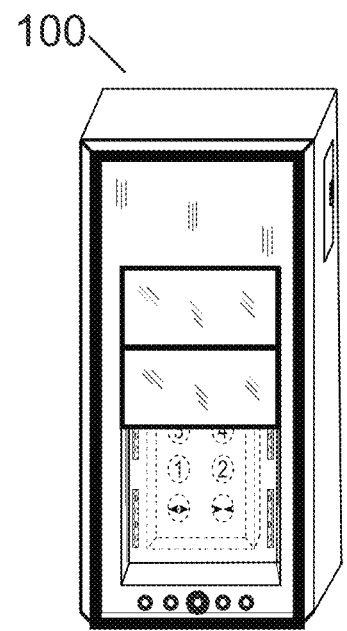
FIG. 17A   FIG. 17B   FIG. 17C
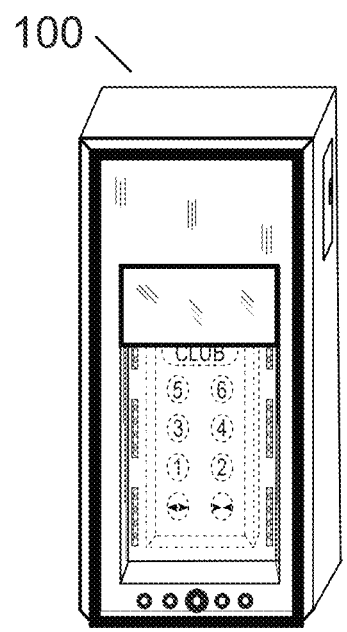
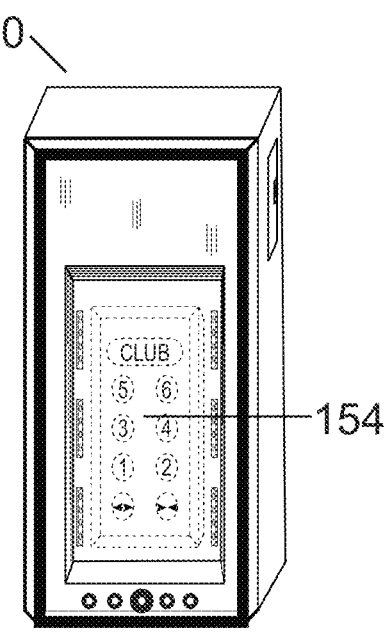
FIG. 17D   FIG. 17E

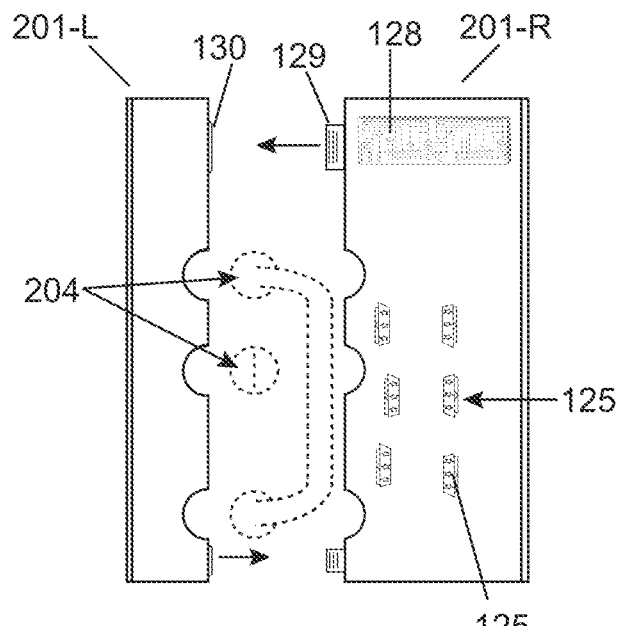
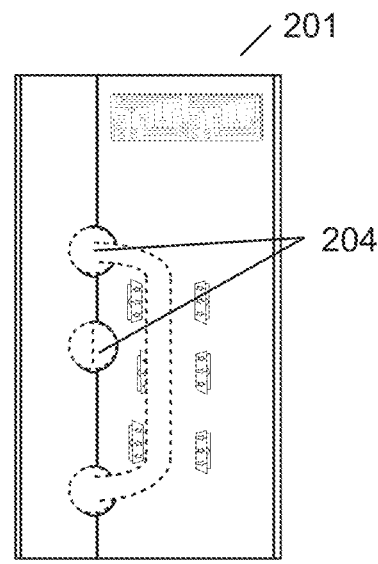
FIG. 18A    FIG. 18B
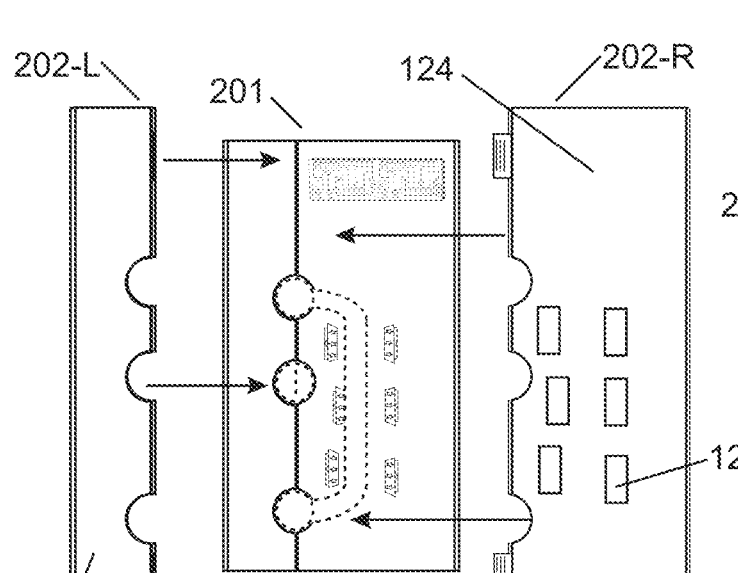
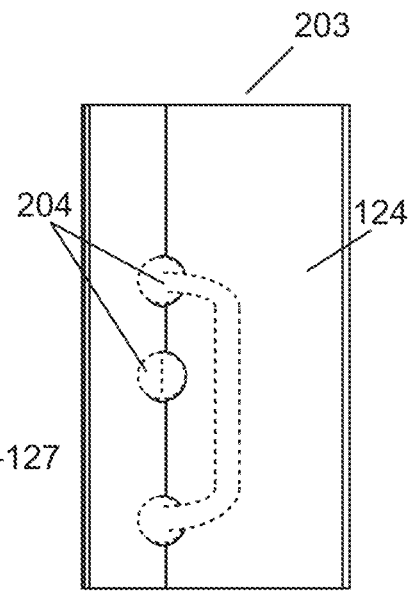
FIG. 18C    FIG. 18D

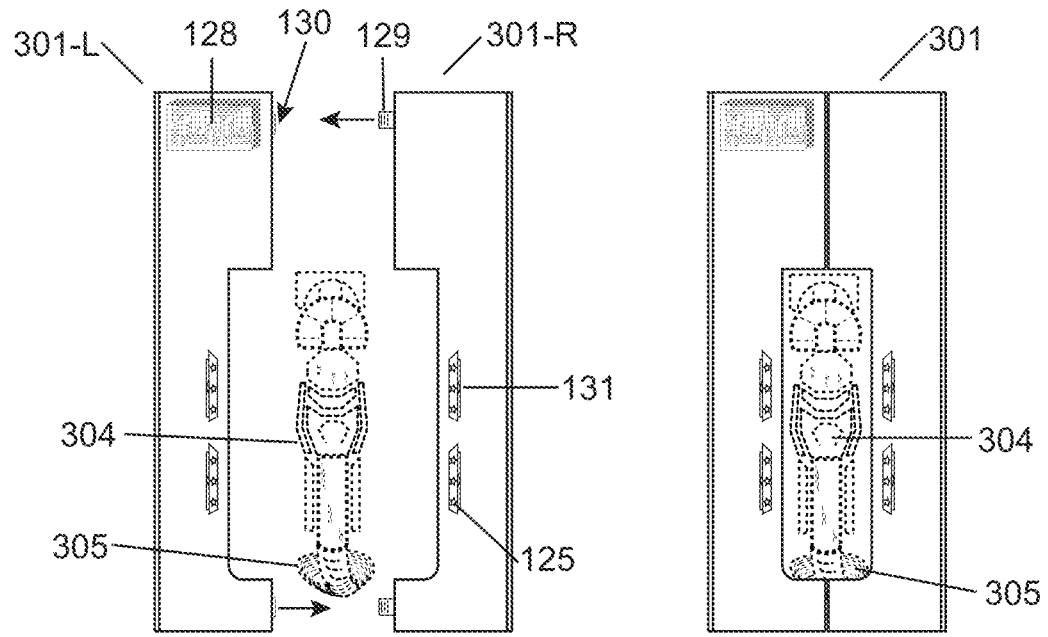
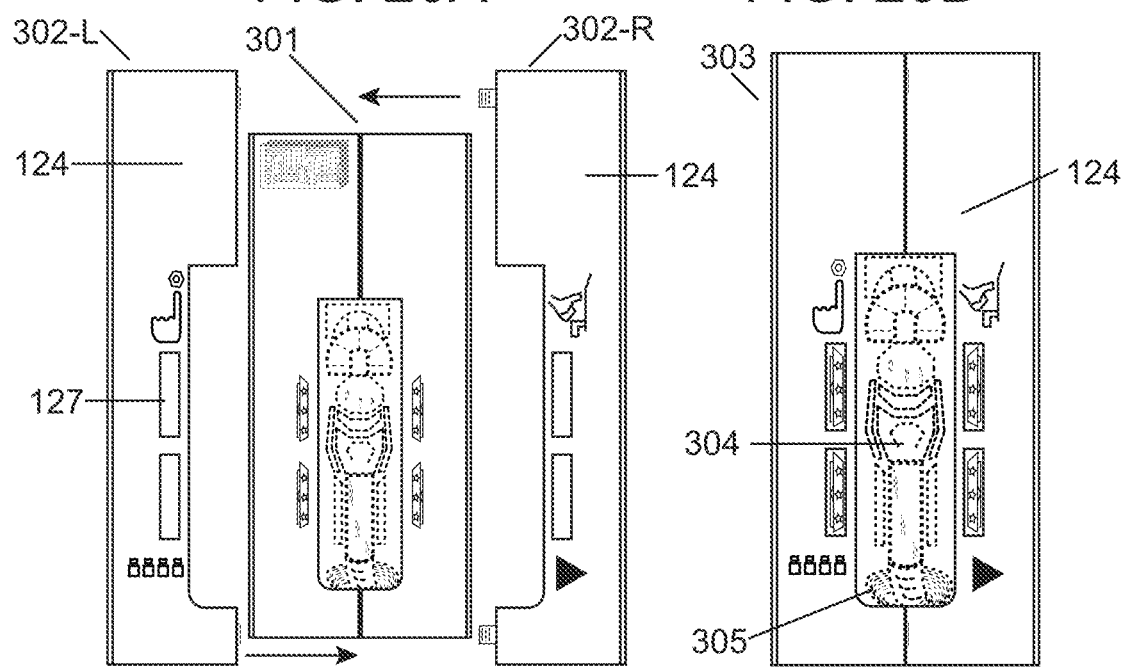
FIG. 20A  FIG. 20B  FIG. 20C  FIG. 20D

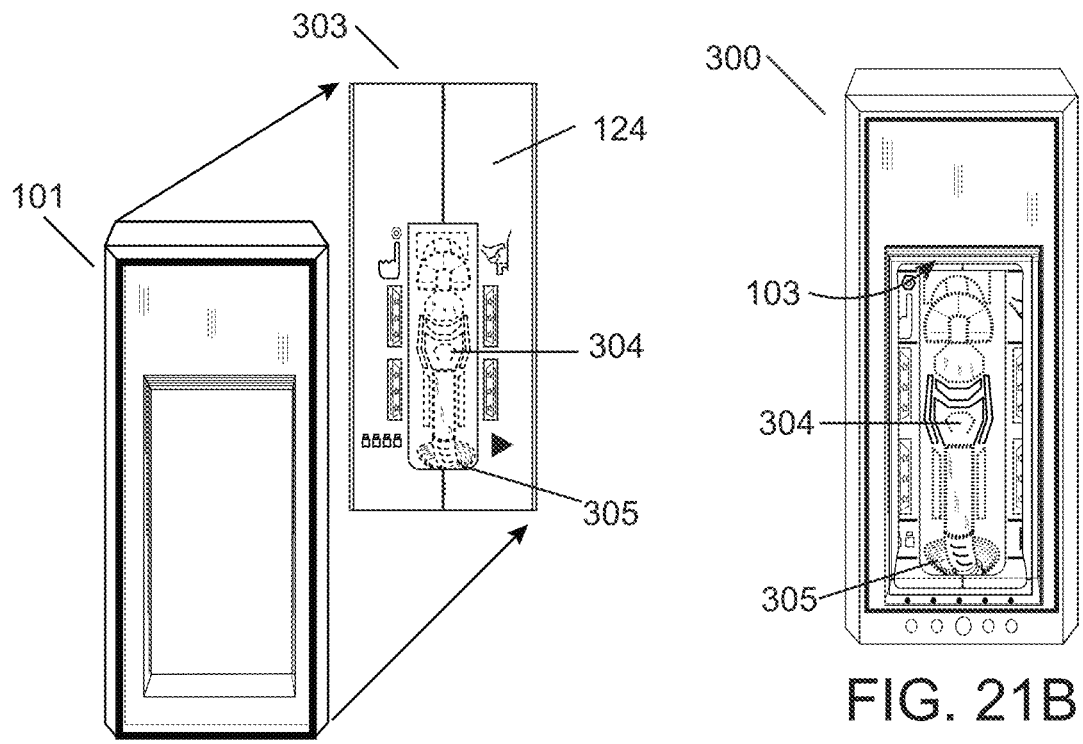
FIG. 21A
FIG. 21B
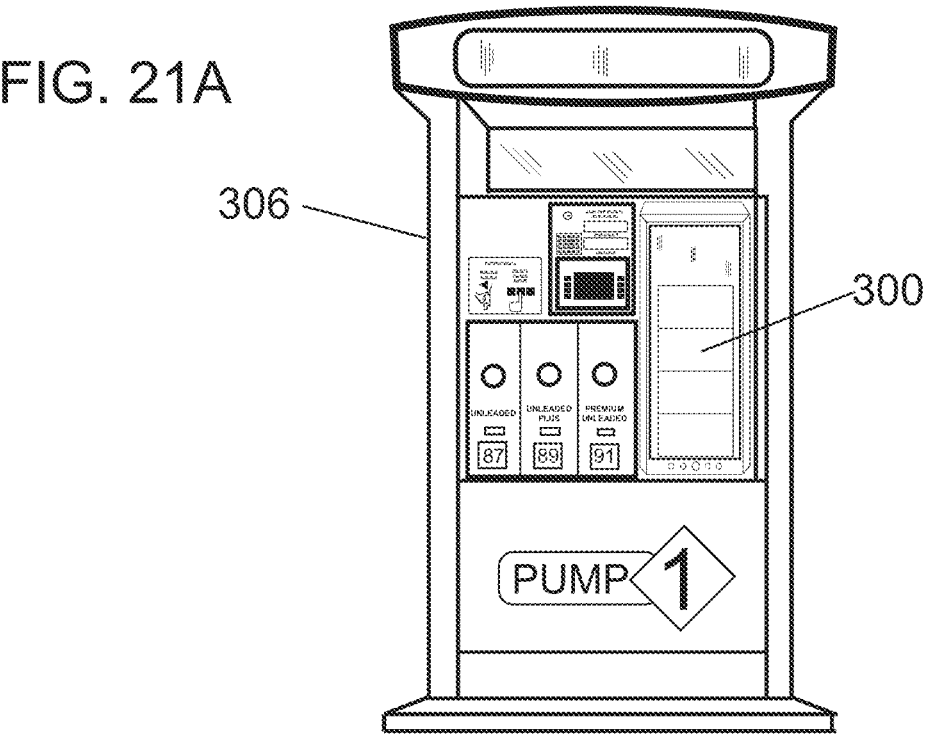
FIG. 21C

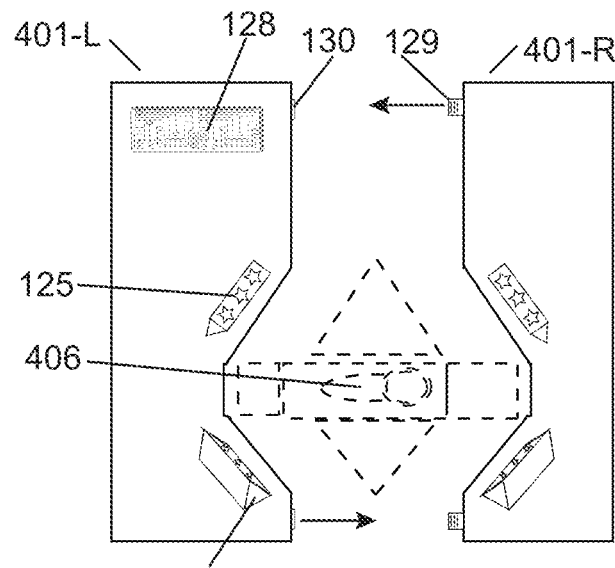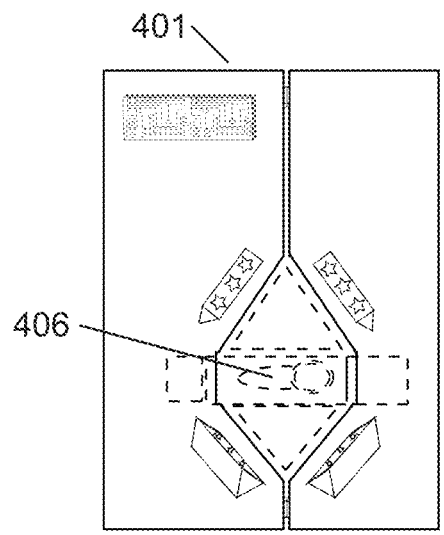
FIG. 23A
FIG. 23B
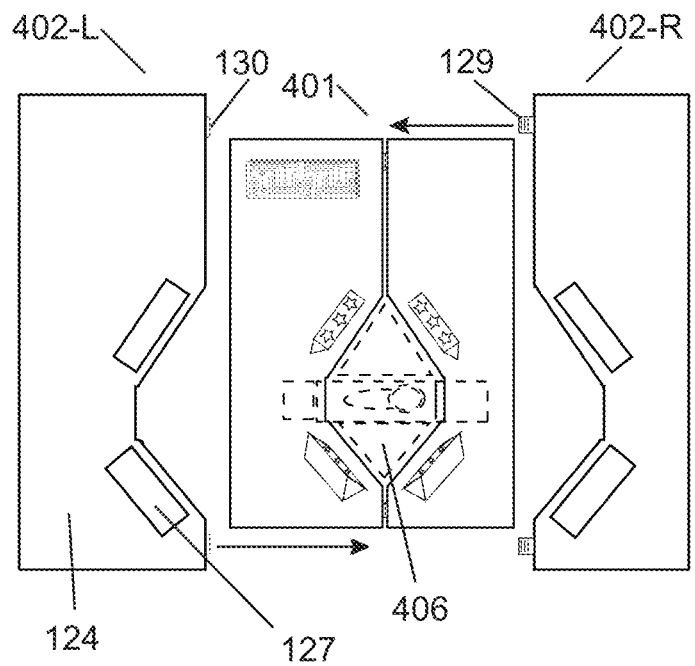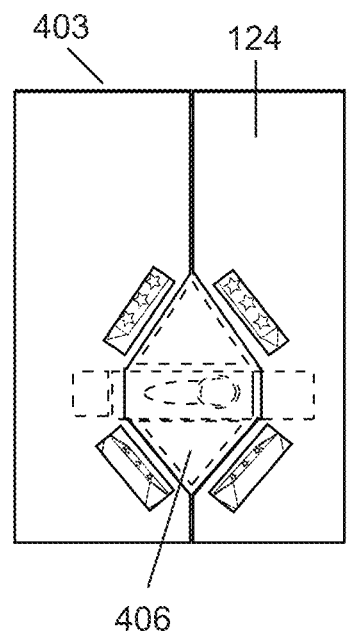
FIG. 23C
FIG. 23D

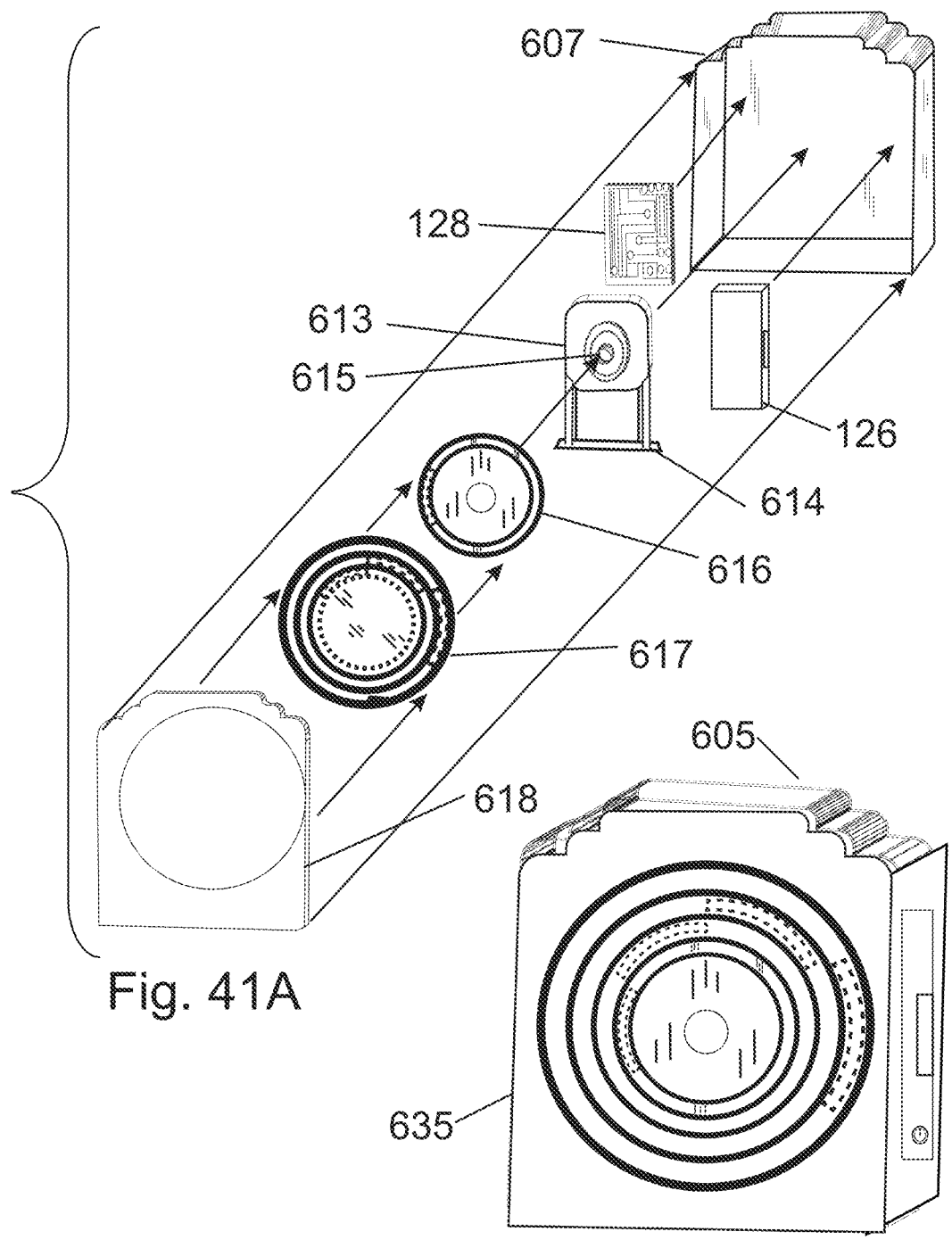

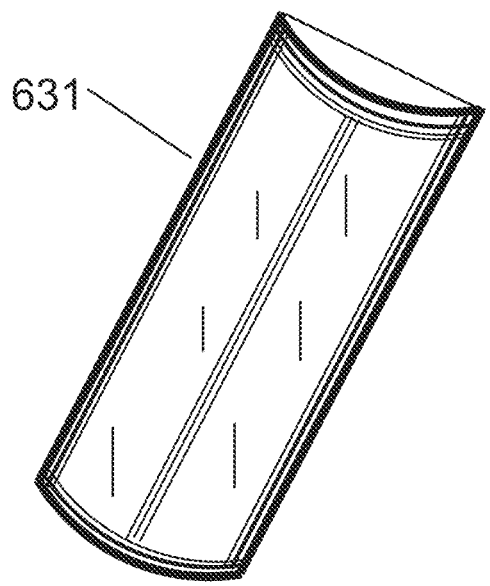
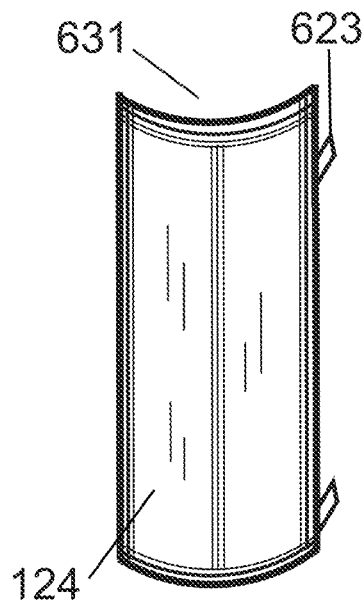
FIG. 45A
FIG. 45B
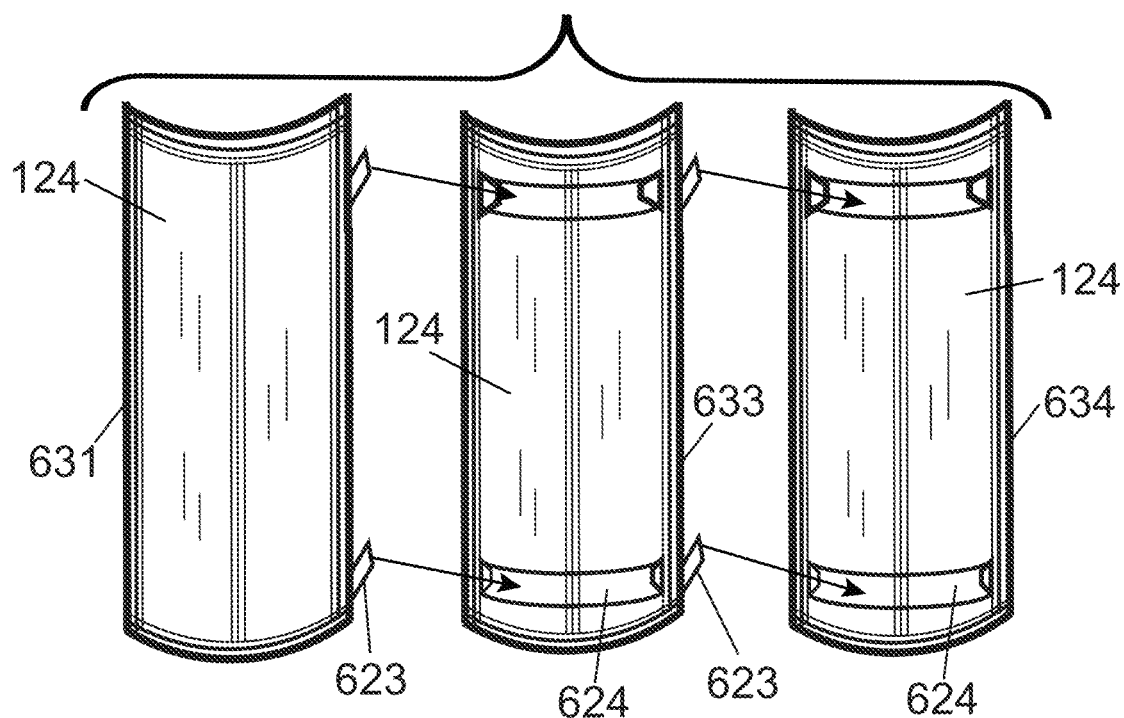
FIG. 45C

DECONTAMINATION OF GERMS ON HUMAN TOUCH POINTS

CROSS REFERENCE TO RELATED APPLICATIONS

This application is a Continuation-in-Part Patent Application that claims priority to U.S. Utility patent application Ser. No. 17/467,208 filed Sep. 4, 2021, which claims priority to U.S. Provisional Patent Application No. 63/075,040 filed Sep. 4, 2020, the entire contents of which are each herein incorporated by reference.

FIELD OF THE INVENTION

The present invention is in the technical field of infectious disease prevention. More particularly, the present invention is in the technical field infectious disease prevention through decontamination of pathogenic microorganisms adjacent to human touch points using ultraviolet germicidal irradiation.

BACKGROUND

Infectious diseases are caused by pathogenic microorganisms such as bacteria, viruses, fungi, and parasites which are often transmitted either directly or indirectly from person to person. Since germs thrive in a warm environment between 95-100°, the skin temperature of humans at 98.6° provides an optimal carrier platform for these microorganisms to survive and multiply. In fact, clinical studies have shown that some bacteria double every twenty minutes resulting in millions of bacteria forming in only eight hours.

While not all germs cause disease, all infectious disease is caused by germs. The four main classes of germs that can cause disease in humans include bacteria, viruses, fungi, and parasites. Studies have shown that 20% of people do not wash their hands after using the restroom and 30% of those that do wash their hands do not use soap. Overall, humans have between two and ten million germs between their fingertips and elbows at any given time. Each time an individual makes contact with a human touch point fomite (an inanimate object) such as, for example, a commercial door handle, a restroom stall latch, a credit card payment terminal, or a gas pump handle, the process of indirect germ transfer to the next user of the fomite is initiated.

Since 80% of infectious disease is transmitted by the hands, the rapid spread of pathogenic microorganisms through public touch points has been a major contributing factor in several global health pandemics including SARS and, most recently, COVID19. These events have crippled the world economy and led to the sickness and death of millions of people.

Current methods deployed to resolve this problem include manual cleaning, antimicrobial materials to manufacture and/or coat the fomites, automated and user-initiated mechanical sanitizing machines, and ultraviolet germicidal irradiation (UVGI). While each of these methods are helpful, their impact is relatively negligible in a high-traffic area due to issues such as rapid recontamination and a lengthy decontamination cycle.

Manual cleaning involves the use of sanitizers, disinfectants, and sterilizers to clean and disinfect surfaces of fomites, with each class of product designed to achieve a different result. Sanitizers prevent growth and/or kill bacteria, but not viruses, in 30 seconds to 5 minutes. Disinfectants serve as a microbicide on bacteria, some viruses, and fungi, achieving results in generally 10 minutes. Sterilizers are the most powerful cleaning agent and, when used properly, kill 100% of bacteria, viruses, fungi, and spores with the time to kill typically 10-15 minutes however this varies depending on the specific agent being used, the environment for which it is applied, and the composition of the material being sterilized.

In addition to the health risks to cleaning personnel and environmental hazards, the efficacy of cleaning agents is dependent on the application process and the surface material to which it is being applied. As noted previously, cleaning agents typically need to remain wet for 5-15 minutes to achieve a 100% reduction in pathogenic microorganisms. This time requirement is often neglected due to poor user training, worker productivity demands, and a desire to rapidly reinstate access to the fomite to users.

Additionally, cleaning personnel often use the same agents to clean all fomites regardless of whether they are constructed of porous or non-porous materials which reduces the sterilization efficacy since most cleaning agents are tailored toward specific types of surfaces. Hospital studies have also shown that some germs which have been "killed" through cleaning agents reproduce into living microorganisms in as little as two hours in a process known as photo reactivation. Lastly, even if the fomite has been properly sterilized, it only remains so until re-contaminated either by airborne bacteria or the next user interaction.

Antimicrobial materials have been used both as a material and as a surface coating for existing fomites. Most recently, copper and its alloys (brasses, bronzes, cupronickel, copper-nickel-zinc, etc.) have been shown to be natural anti-microbial materials with intrinsic properties to destroy a wide range of microorganisms. One detriment for the use of copper on public touch points is that studies have shown it takes two hours to kill 99.9% of bacteria and up to six hours to kill 99.9% of viruses when combined with a regular cleaning schedule.

Utilizing antimicrobial film and photodynamic polymer coatings have also been discussed as a potential solution. One of the problems with these solutions is the amount of time it takes for the material to be photosensitized. In the case of photodynamic polymers, which only require oxygen and natural light, this process takes sixty minutes to achieve a 1 log anti-microbial reduction.

There are three primary issues that prevent antimicrobial materials and coatings from being an adequate solution to prevent the transmission of infectious diseases from human touch point fomites. First, during the lengthy timeframe necessary to achieve a 99.9% inactivation of pathogenic microorganisms, millions of additional microorganisms have been placed on the fomite by new users making it unlikely that a fomite will be disinfected during a period of heavy use. Second, their efficacy varies depending on the germ it is combatting. Some are only effective against bacteria or viruses but not both. Of those that have proven capable of killing both bacteria and viruses, many of those are unable to kill other classes of pathogenic microorganisms such as fungi, spores, and/or parasites. Meanwhile, none of these materials have shown to be equally effective against all microorganisms. Lastly, the cost and deployment time to replace and coat all public facing fomites makes this option both undesirable and unrealistic.

Mechanical sterilizing options of human touch point fomites include user-actuated and automated mechanical machines to kill pathogenic microorganisms, utilizing either chemicals in the form of sanitizers, disinfectants, or sterilizers or germicidal light performing ultraviolet germicidal irradiation (herein referred to as UVGI). Machines utilizing chemicals are typically mounted adjacent to a fomite and have a housing filled with cleaning product which is applied to the target surface either through a user actuated lever or the triggering of the action through an automated sensor. The user actuated model poses a problem at the point of initiation since germs are spread to the lever from each user's hand which accumulate each time the machine is used.

The automated sensor-actuated machine resolves the user interface problem, but other critical issues persist in the fight against human touch point germ contamination especially in public spaces. First, chemicals typically need up to 15 minutes to achieve optimal efficacy in killing pathogenic microorganisms which is often not enough time for frequently accessed fomites to be contagion-free prior to the next user interaction. Second, even if effective in killing germs on the fomite, the chemical residue poses a new health risk as it is distributed to the hands of subsequent users. Lastly, the chemical residue surrounding the distribution area creates the potential for slip and fall injuries.

Ultraviolet germicidal irradiation (UVGI) has been validated as a method of sterilization in medical and surgical environments since the 1950's. The wavelength between 200-280 nm is classified as UV-C light and has the strongest germicidal effect. Through exposure to UV-C, the DNA of the pathogens is destroyed, rendering them incapable of replicating. Until relatively recently, the primary method of producing germicidal light was using mercury-filled tubes. Colloquially known as germicidal lamps, these are similar in appearance to a standard fluorescent light. Producing light at a peak of 253.7 nm, it is effective in killing pathogenic microorganisms but not optimal, since 265 nm has been proven to be the most effective wavelength against the broad spectrum of bacteria and viruses.

The use of UV-C light to eliminate pathogenic microorganisms is a globally accepted solution and is widely used in medical environments including sterilization of instruments, devices, operating and patient rooms, and within HVAC systems. It is also commonly used to treat air, water, and surfaces in various industries and sectors including but not limited to water purification plants, food production and packaging, and warehouses. In recent years, small user-actuated UV-C devices such as lamps and handheld wands have been made available to the consumer market for sterilization of surfaces such as sinks, toilets, toothbrushes, keys, and cell phones.

However, germicidal lamps have not proven to be a commercially viable solution for eradication of germs on public touch point fomites. The drawbacks of using germicidal lamps on high traffic surfaces such as door handles and elevator buttons, for example, include but are not limited to; the inability to perform rapid cycling, reduced total life expectancy when repeatedly cycled on and off, slow startup time to reach its peak wavelength, high heat production, additional equipment required to operate i.e. a ballast, and a danger to the general public if leaking mercury from defective or broken bulbs comes into contact with human skin or eyes.

Therefore, a need exists in the field for novel germ decontamination methods, devices, and apparatuses capable of rapid and efficient sterilization of human touch point fomites to prevent the spread of infectious disease and loss of millions of lives.

SUMMARY OF THE INVENTION

A germ decontamination apparatus includes an enclosure including an access door configurable to be in an open or closed position, an opening for positioning the enclosure over or around a fomite, a drive assembly configured to open the access door in response to a trigger or triggering event, one or more ultraviolet light sources disposed inside the enclosure and configured to decontaminate the fomite. The germ decontamination apparatus may include one or more sensors configured to detect a triggering event. The one or more sensors may include a motion detector sensor and/or a light sensor. The access door may include one or more access panels. The one or more ultraviolet light sources may produce UV-C radiation with a wavelength in the range of 200-280 nm.

The disclosure is directed to a germ decontamination method and apparatus which forms a chamber that affixes to and encloses human touch point fomites including but not limited to door handles, restroom stall latches, deadbolts, gas pump handles, retail point of-sale (POS) terminals, automatic teller machines, shopping cart handles, elevator control panels, public telephones, paper towel extraction levers, toilet handles and seats, etc. This apparatus automatically kills adjacent germs within seconds after each interaction with a user through ultraviolet germicidal irradiation (herein referred to as "UVGI"). The UVGI dose is delivered through UV-C LED semiconductor chips (herein also referred to as "UV-C") optimally mounted at a fixed or adjustable angle to the baseplate and/or upper housing to ensure proper coverage and the most effective placement. The chips are preferably delivering their dose at an optimal wavelength of 265 nm or alternatively through a multiwavelength UV-C LED array to specifically target different classes of germs. Internal components enveloping fomites within the chamber are layered with a UV-C reflective material such as aluminum foil, PTFE, UV-reflective paint, or any similar material proven to optimize reflectivity. Once the UVGI dose has been administered, the fomite remains sealed within the enclosure to prevent recontamination resulting from airborne pathogenic microorganisms. Upon detection of the presence of a subsequent user through sensor technology, the drive and pulley system retract the stacking access panels to allow germ-free touch point interaction with the fomite which, upon conclusion, triggers the closure of the access panels and the UVGI cycle to be repeated.

The disclosure is also directed to a germ decontamination system comprising a product comprising a fomite, wherein any of the germ decontamination apparatuses described herein are configured to be integrated into the product comprising a fomite. In certain embodiments, the product comprising a fomite is a door, a restroom stall, a deadbolt, a gas pump, a retail point of-sale (POS) terminal, an automatic teller machine, a shopping cart, an elevator, a public telephone, a paper towel dispenser, a computer keyboard, or a toilet.

Other features and aspects will be apparent from the following detailed description, the drawings, and the claims.

BRIEF DESCRIPTION OF THE DRAWINGS

The following figures show various features and aspects of the present invention.

FIG. 9A reveals a side view of a drive clip.

FIG. 9B displays a top view of a drive clip.

FIG. 9C presents an outer side view of an access panel support arm.

FIG. 9D illustrates an inner side view of an access panel support arm.

FIG. 17A shows a front view of a germ decontamination chamber closed and sealed.

FIG. 17B shows a front view of a germ decontamination chamber with the access panels 25% retracted.

FIG. 17C shows a front view of a germ decontamination chamber with the access panels 50% retracted.

FIG. 17D shows a front view of a germ decontamination chamber with the access panels 75% retracted.

FIG. 17E shows a front view of a germ decontamination chamber with the access panels 100% retracted and parked in the panel bay revealing an elevator control panel.

18A displays a front view of a detached fitted door handle baseplate and commercial door handle and lock.

FIG. 18B presents a front view of a fitted door handle baseplate adjacent to a commercial door handle and lock.

FIG. 18C illustrates a front view of a detached door handle baseplate cover and fitted door handle baseplate adjacent to a commercial door handle and lock.

FIG. 18D depicts a front view of a fitted door handle baseplate assembly and commercial door handle and lock.

Figure 19A:
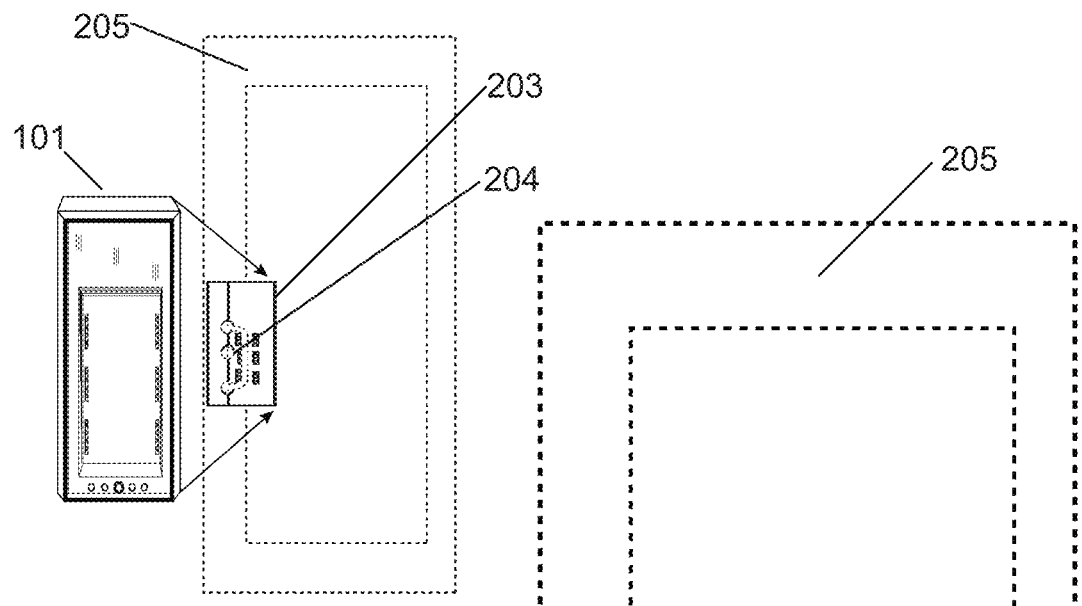

FIG. 19A shows a front perspective exploded view of the upper housing assembly projected into position adjacent to a door handle baseplate assembly and commercial door.

Figure 19B:
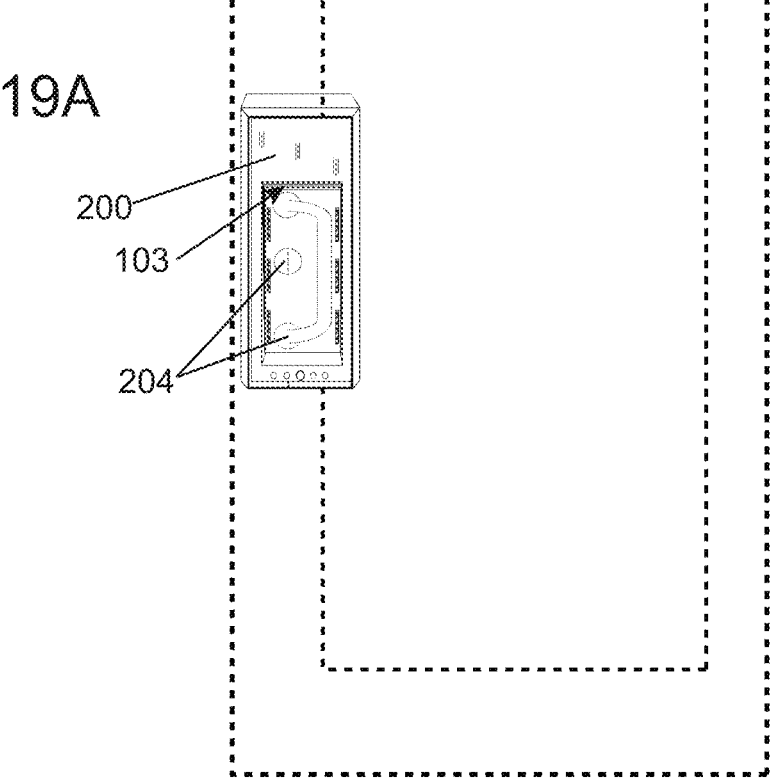

FIG. 19B portrays a front view of a commercial door handle germ decontamination chamber with access panels retracted adjacent to a commercial door.

FIG. 20A represents a front view of a detached fitted gas pump baseplate with a microcontroller, UV-C, and gas pump handle.

FIG. 20B exhibits a front view of a fitted gas pump baseplate with microcontroller and UV-C adjacent to a gas pump handle.

FIG. 20C reveals a front view of a detached gas pump baseplate cover and fitted baseplate adjacent to a gas pump handle.

FIG. 20D displays a front view of a fitted gas pump baseplate assembly and gas pump handle.

FIG. 21A presents a front exploded perspective view of the upper housing assembly projected into position adjacent to a gas pump baseplate assembly and gas pump handle.

FIG. 21B illustrates a front view of a germ decontamination chamber with access panels retracted adjacent to a gas pump handle.

FIG. 21C depicts a front view of a gas pump service island with a gas pump handle germ decontamination chamber adjacent to a gas pump.

Figure 22A:
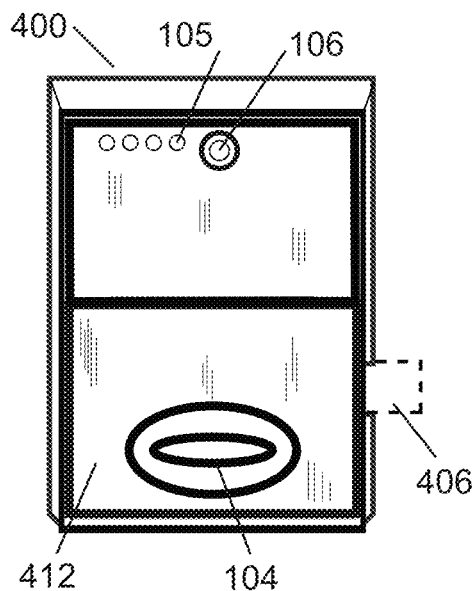

FIG. 22A shows a front view of a restroom stall latch germ decontamination chamber in the closed position.

Figure 22B:
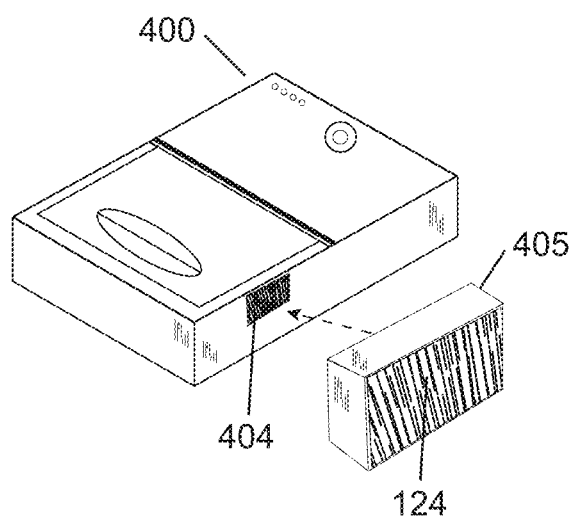

FIG. 22B exhibits an elevated side perspective view of a restroom stall latch germ decontamination chamber and brush shield.

Figure 22C:
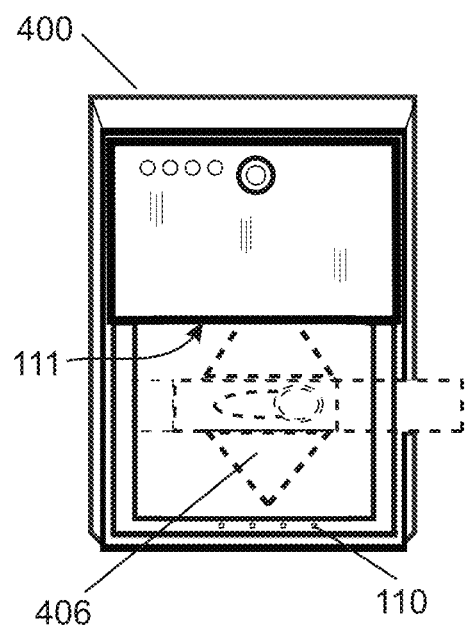

FIG. 22C portrays a front view of a restroom stall latch germ decontamination chamber in the open position adjacent to a stall latch.

Figure 22D:
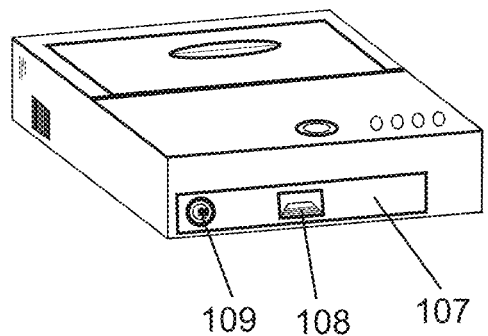

FIG. 22D represents a top perspective view of a restroom stall latch germ decontamination chamber and battery access door.

FIG. 23A displays a front view of a detached fitted stall latch baseplate, microcontroller, and mounted UV-C.

FIG. 23B exhibits a front view of a fitted stall latch baseplate with microcontroller and UV-C adjacent to a restroom stall latch.

FIG. 23C reveals a front view of a detached stall latch baseplate cover and fitted baseplate adjacent to a restroom stall latch.

FIG. 23D displays a front view of a fitted stall latch baseplate assembly and restroom stall latch.

Figure 24:
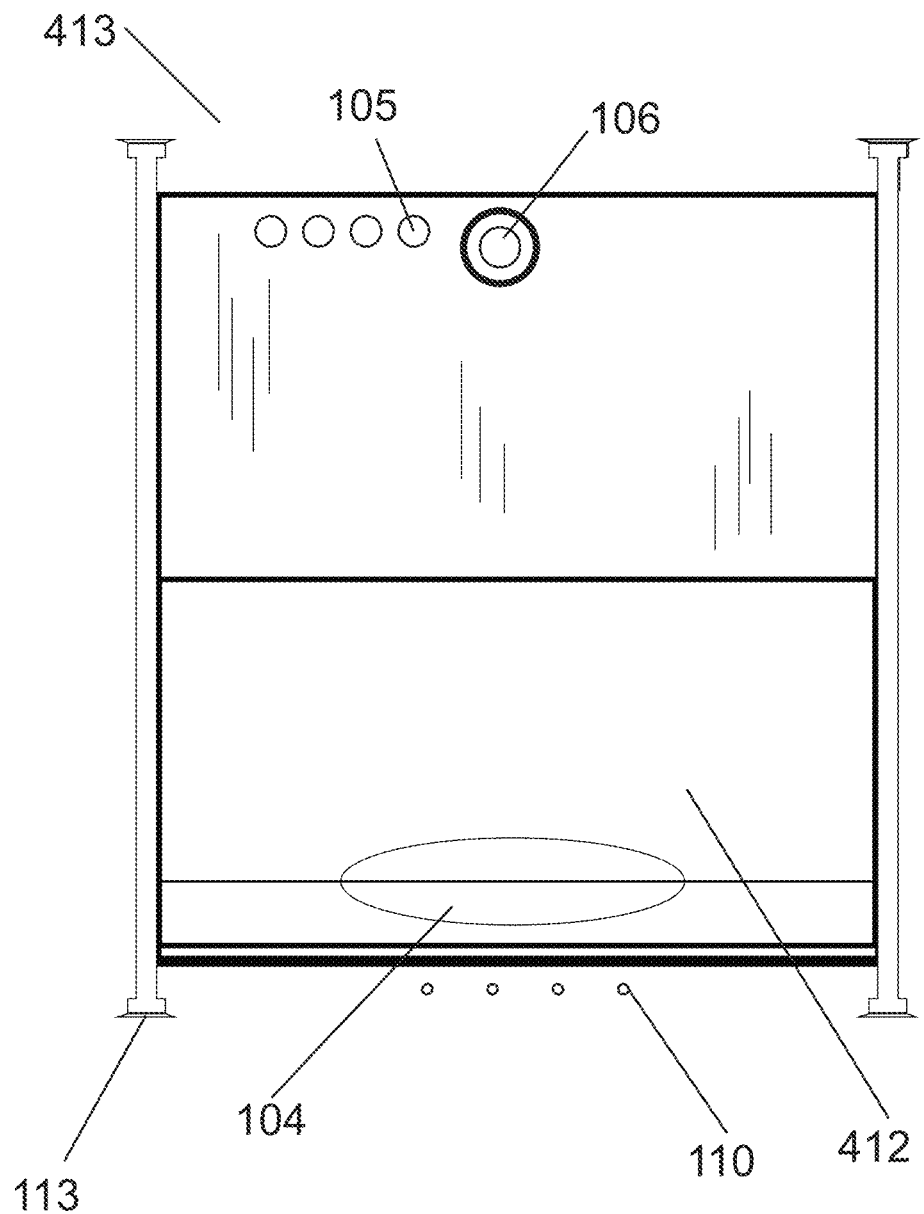

FIG. 24 shows a front closeup view of a restroom stall latch access panel assembly.

Figure 25:
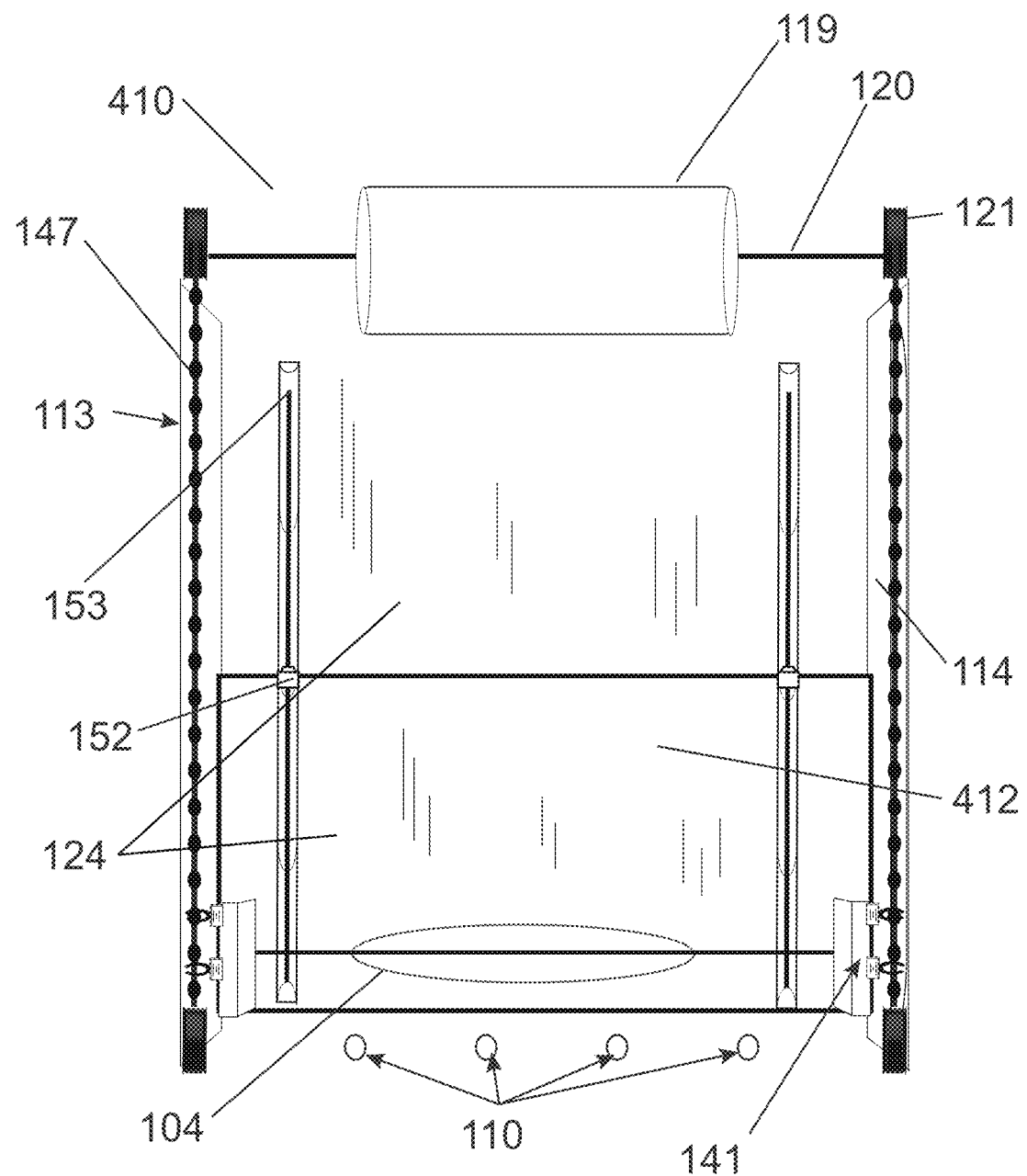

FIG. 25 portrays a rear closeup view of the restroom stall latch drive assembly.

Figure 26:
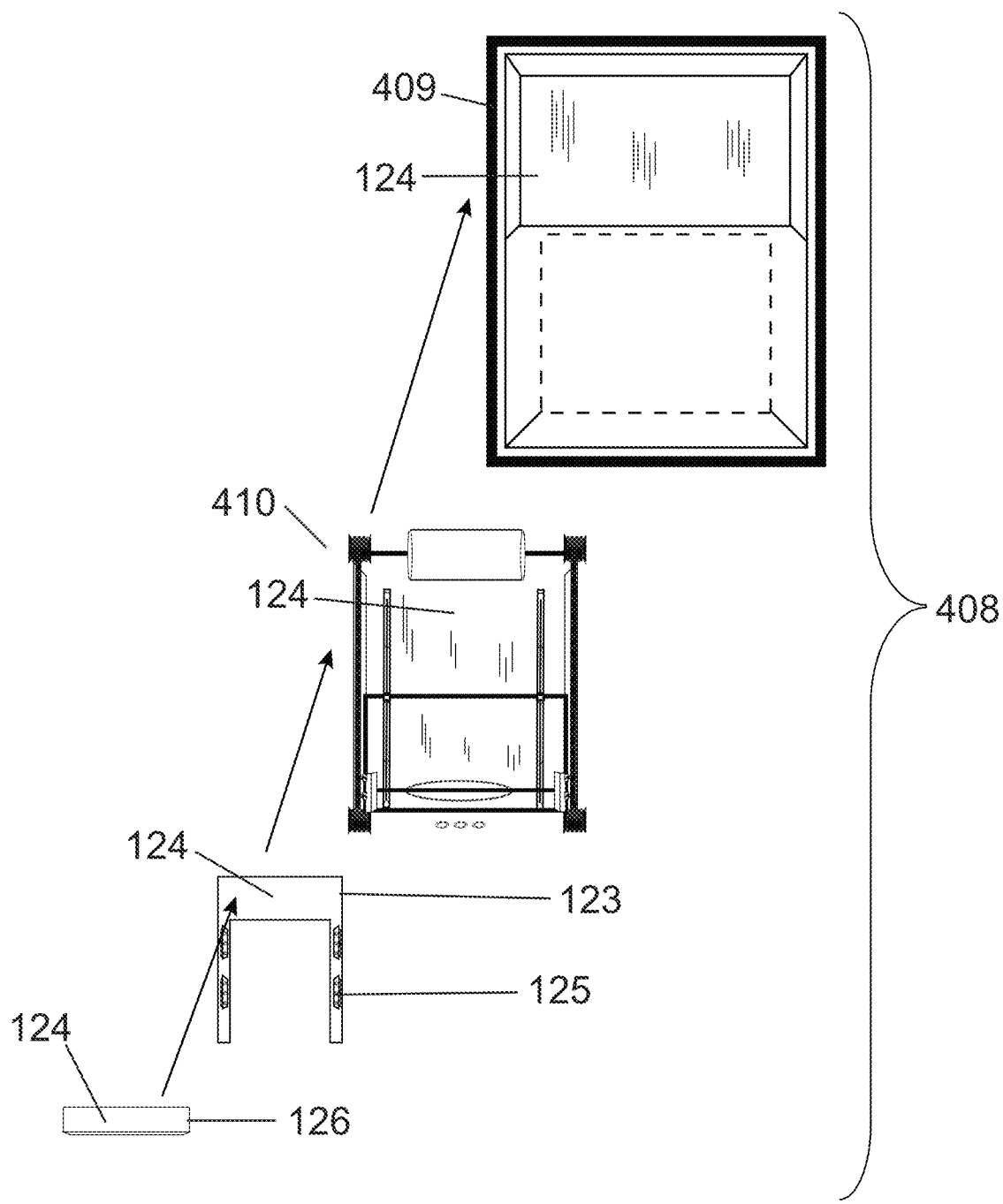

FIG. 26 represents a rear exploded view of the components comprised within the restroom stall latch upper housing assembly.

Figure 27:
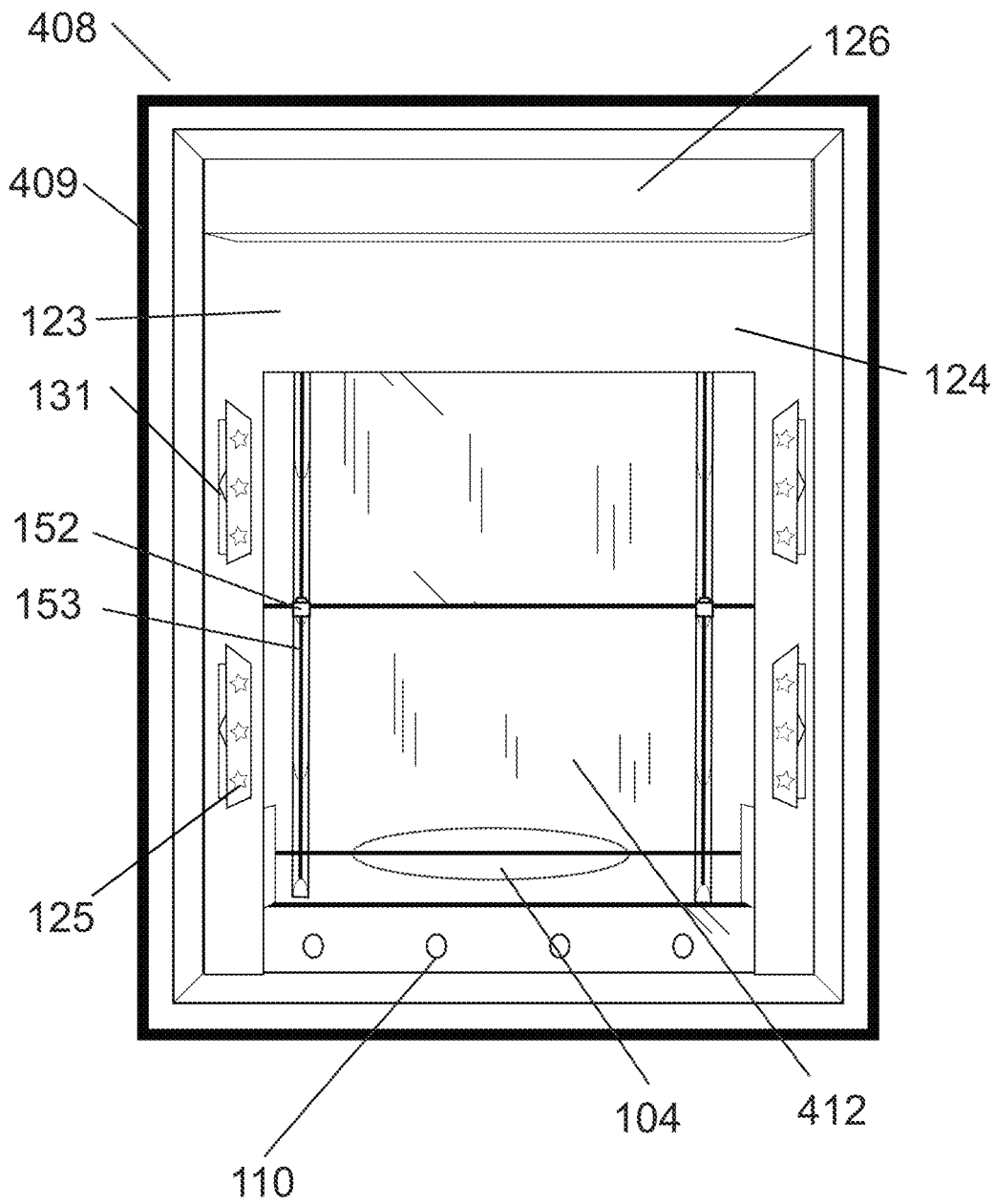

FIG. 27 reveals a rear closeup view of the restroom stall latch upper housing assembly.

Figure 28:
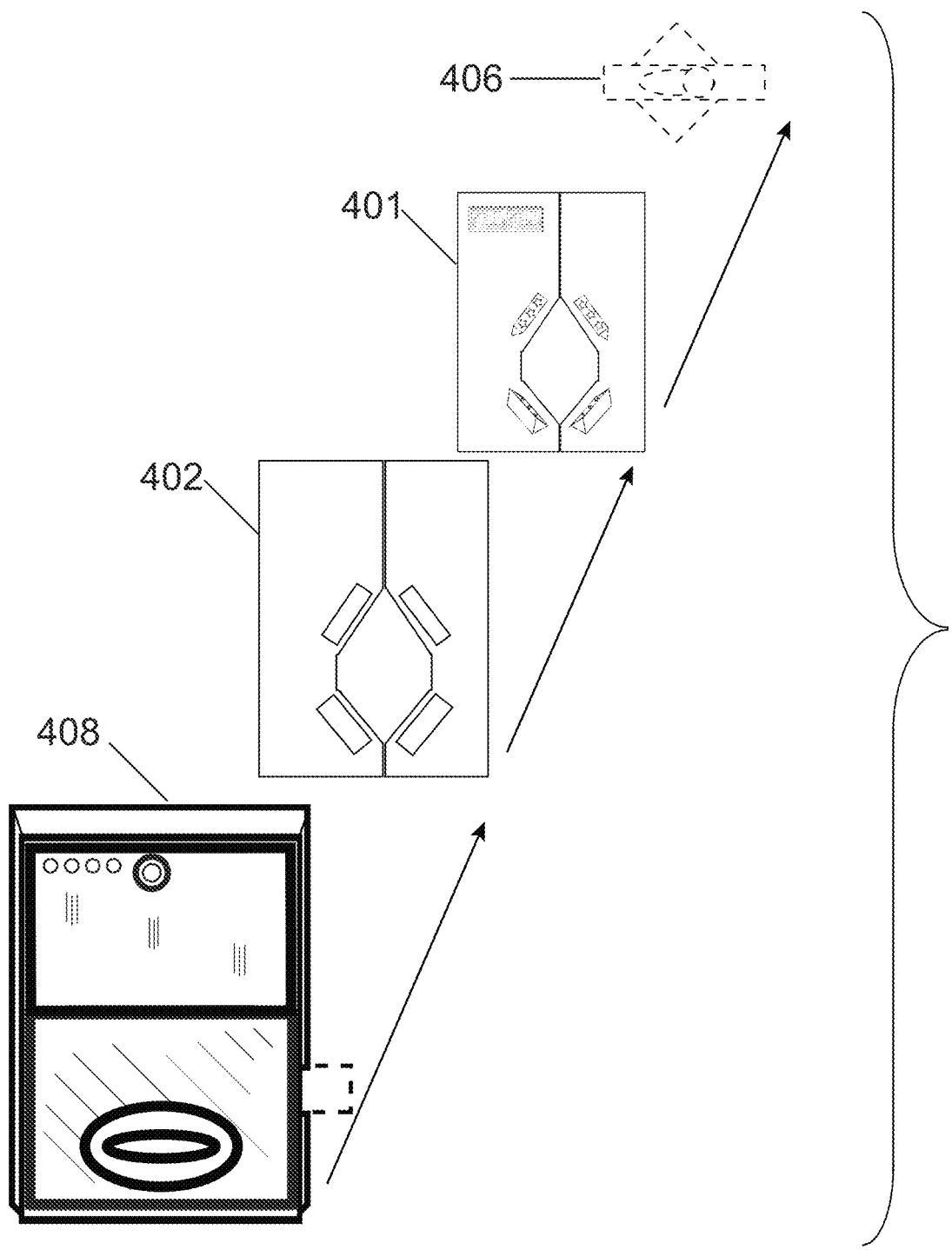

FIG. 28 displays a front exploded view of the restroom stall latch upper housing, baseplate cover, and baseplate.

Figure 29:
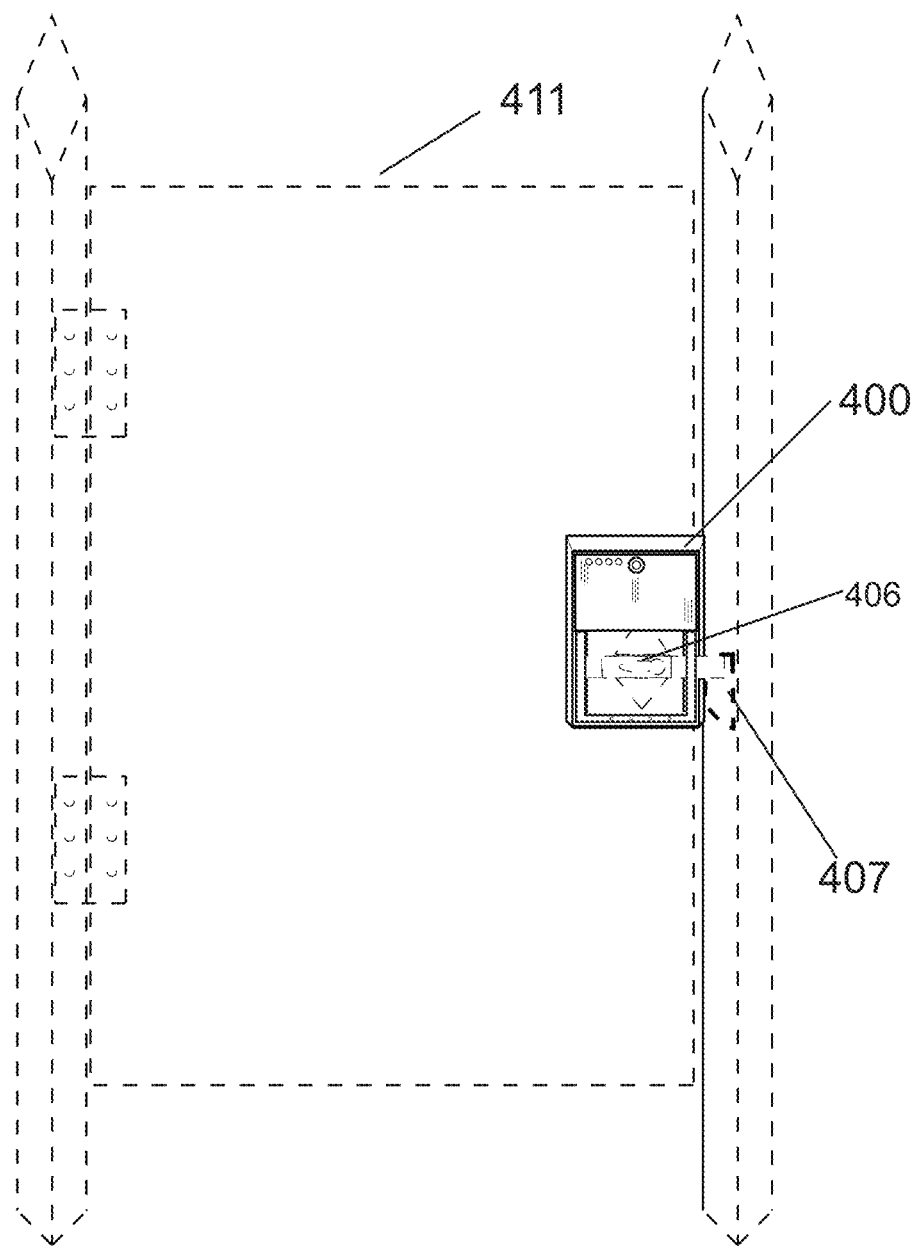

FIG. 29 presents a front view of a restroom stall latch germ decontamination chamber in the open position adjacent to a restroom stall latch and door.

Figure 30A:
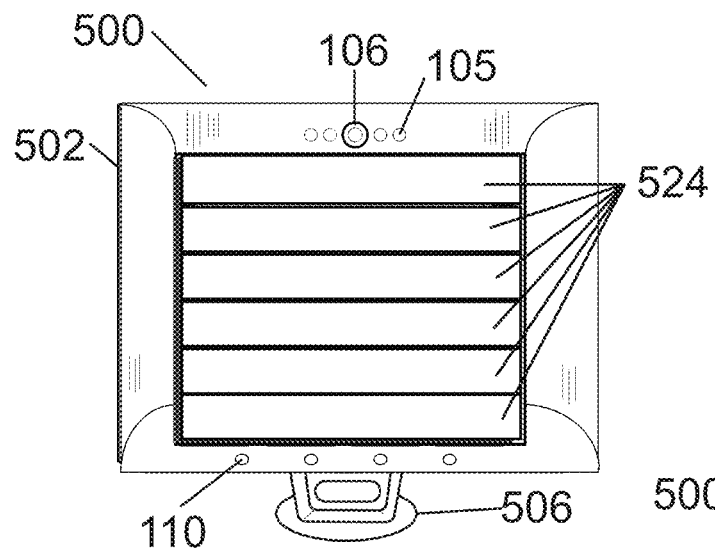

FIG. 30A illustrates a front view of a retail point-of-sale terminal ("POS") germ decontamination chamber (herein referred to as "POS chamber") and mounting stand.

Figure 30B:
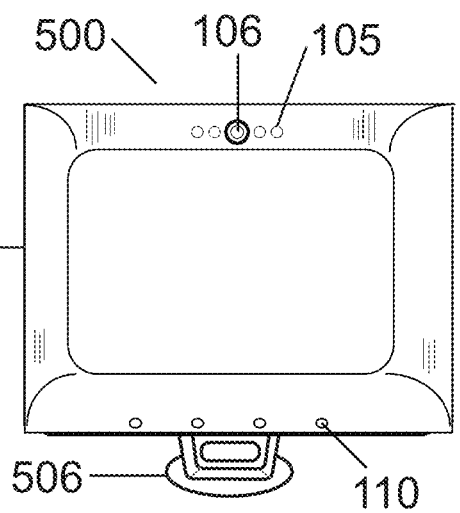

FIG. 30B presents a front view of an open POS chamber and mounting stand.

Figure 30C:
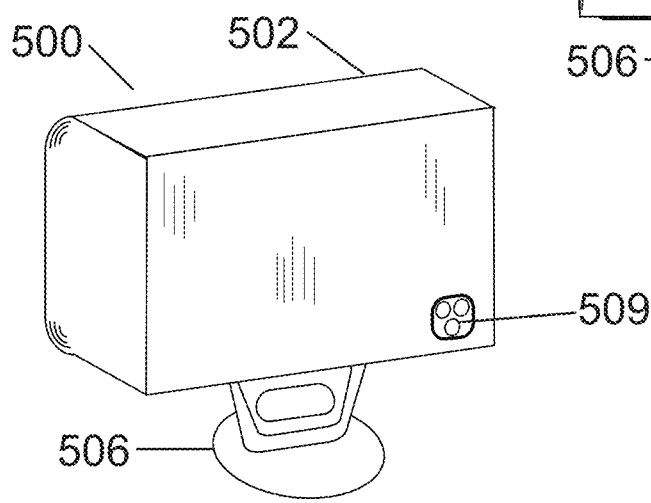

FIG. 30C illustrates a rear perspective view of a POS chamber and mounting stand.

Figure 31A:
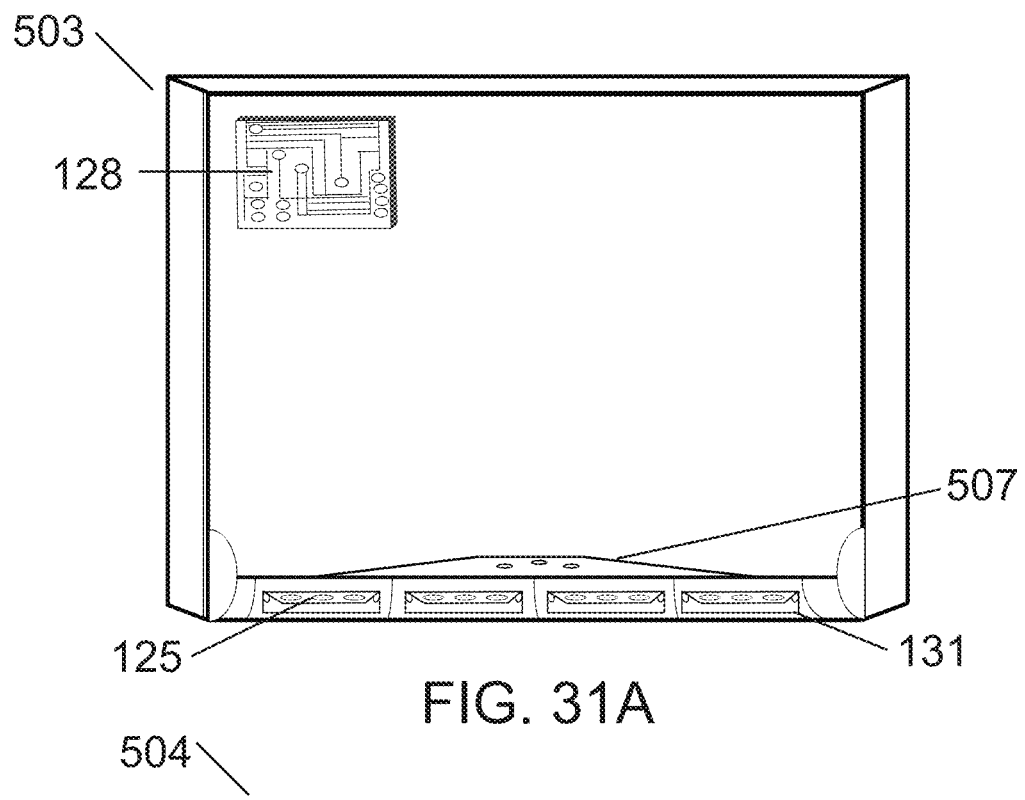

FIG. 31A depicts a front view of a POS baseplate with microcontroller and UV-C.

Figure 31B:
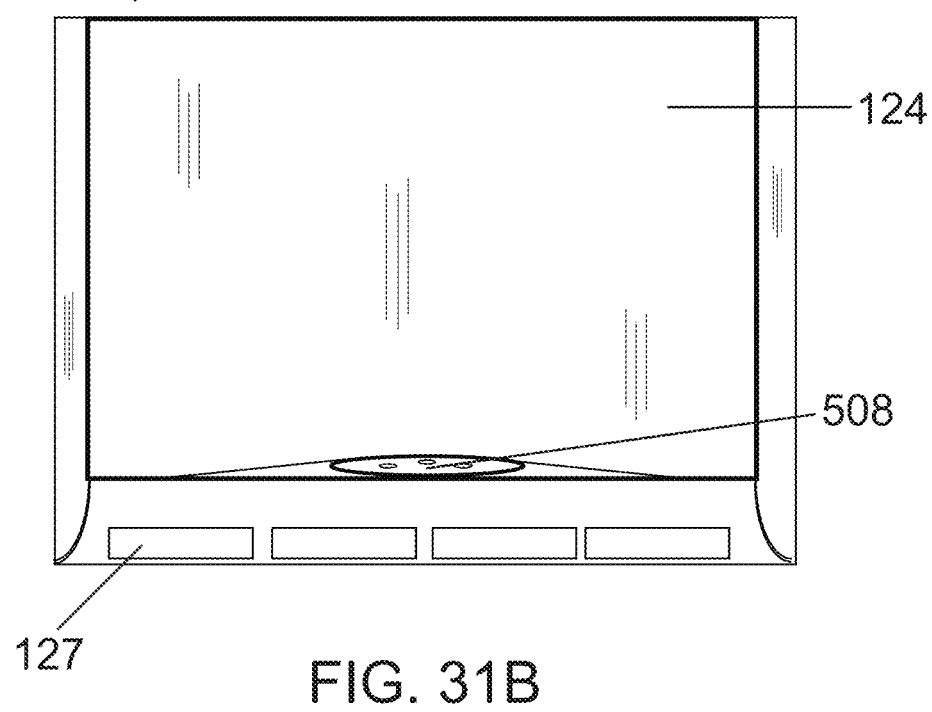

FIG. 31B shows a front view of a POS baseplate cover with UV-C cutouts.

Figure 32A:
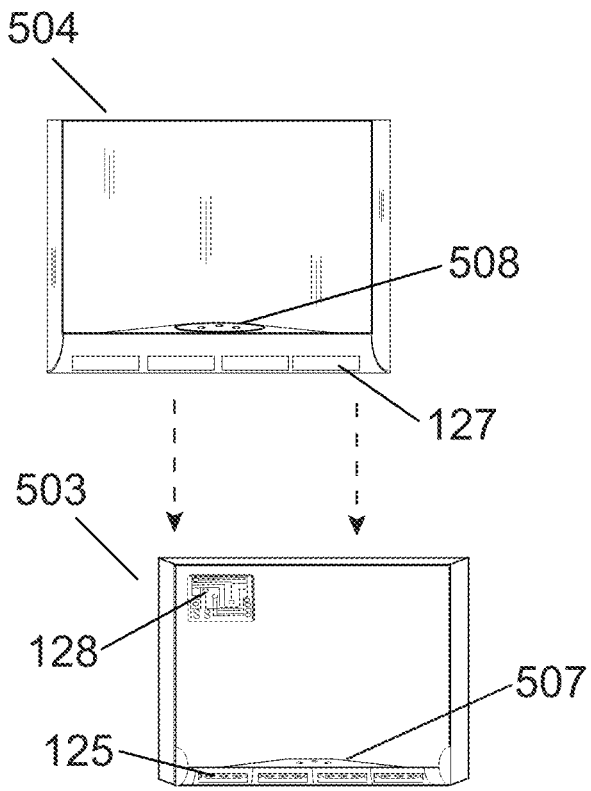

FIG. 32A portrays a front exploded view of a POS baseplate cover being projected into position over and adjacent to a POS baseplate and mounting stand.

Figure 32B:

FIG. 32B represents a front view of a POS baseplate assembly and mounting stand.

Figure 33A:
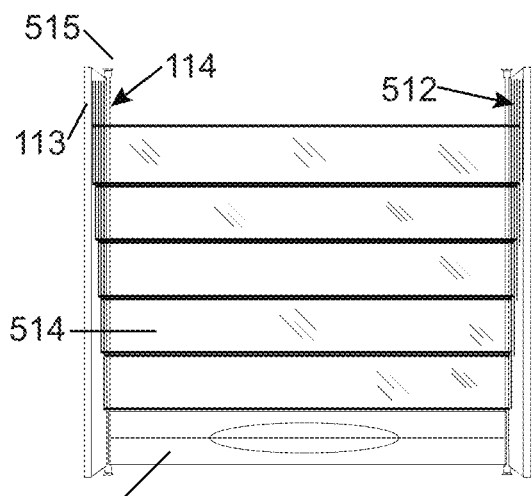

FIG. 33A exhibits a front closeup view of a POS chamber access panel assembly.

Figure 33B:
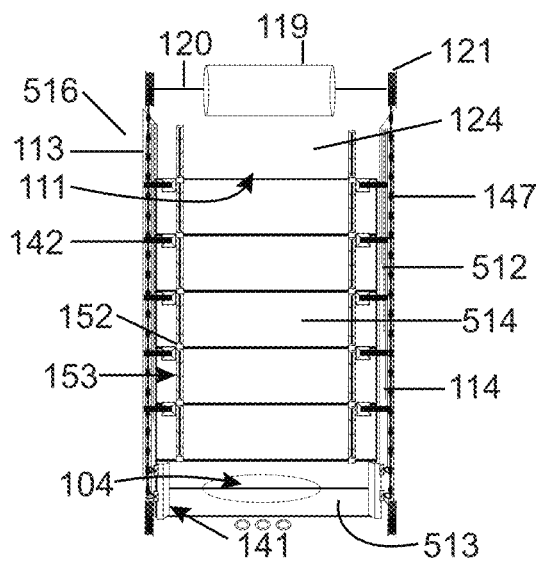

FIG. 33B reveals a rear view of a POS chamber drive assembly.

Figure 33C:
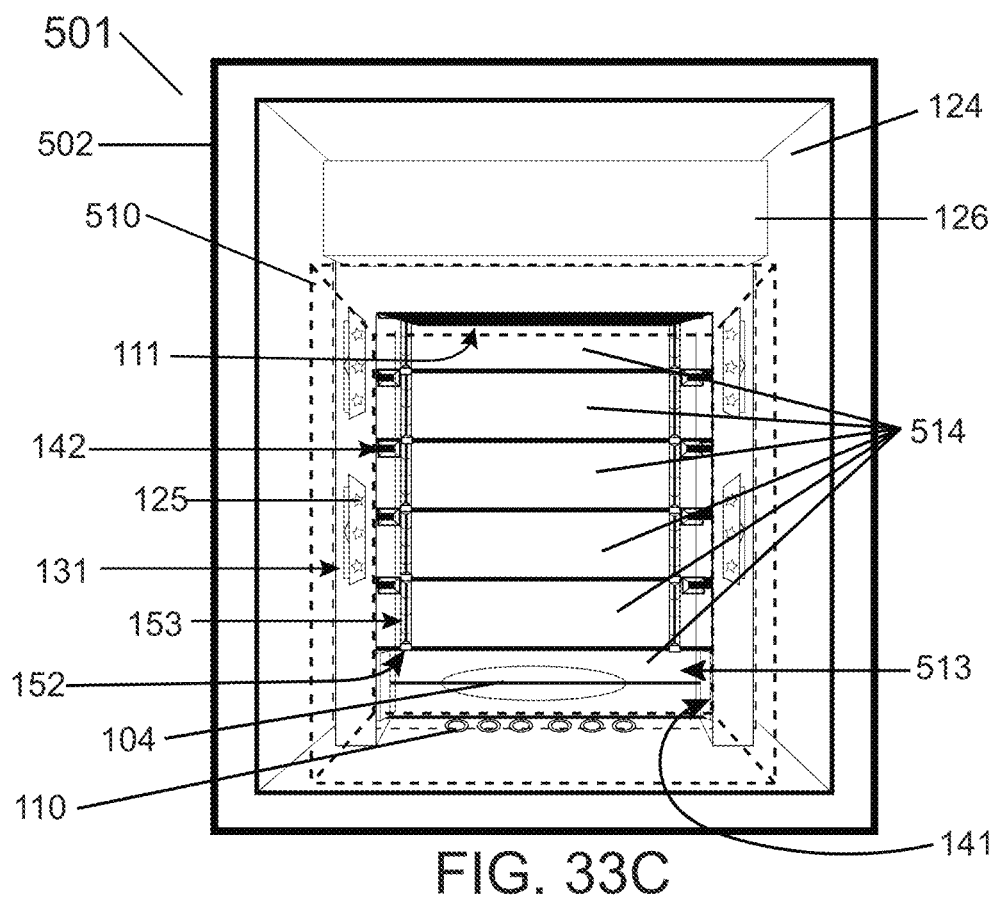

FIG. 33C displays a rear view of a POS chamber upper housing assembly.

Figure 34A:
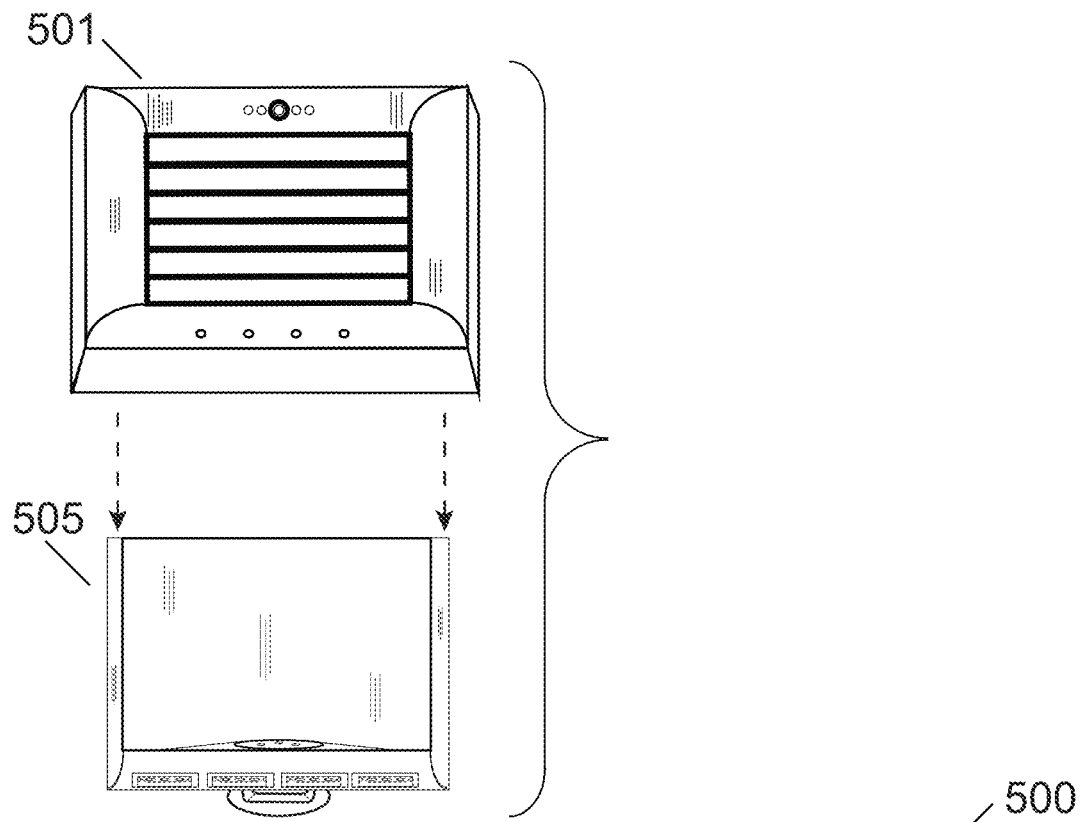

FIG. 34A exhibits a front exploded view of a POS chamber upper housing assembly projected into position upon the POS baseplate assembly and mounting stand.

Figure 34B:
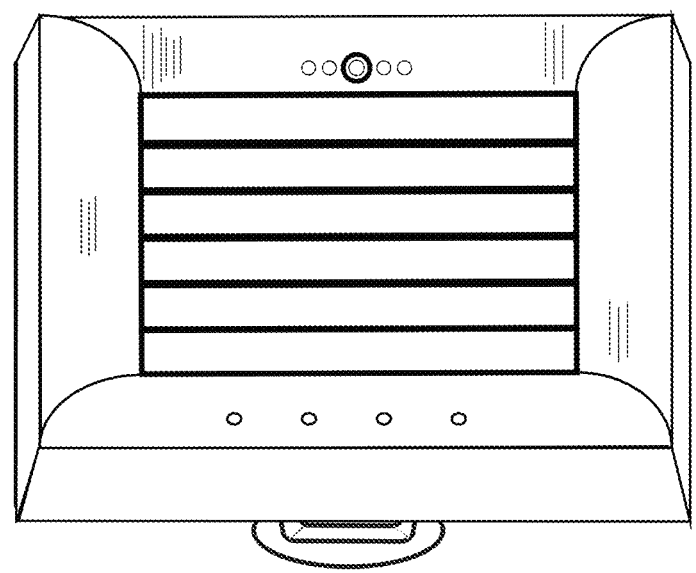

FIG. 34B depicts a front view of a closed POS chamber.

Figures 35A, 35B, 35C:
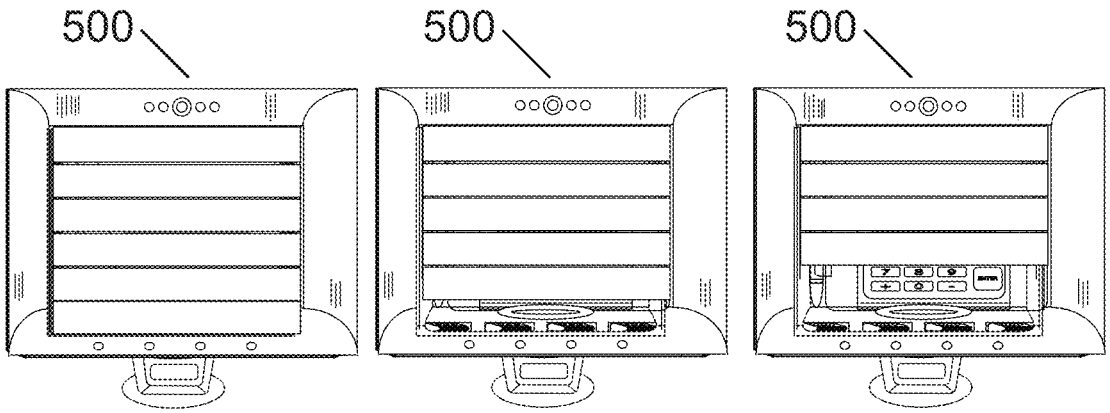

FIG. 35A reveals a front view of a POS chamber in the closed position.

FIG. 35B reveals a front view of a POS chamber with one access panel retracted.

FIG. 35C reveals a front view of a POS chamber with two access panels retracted.

Figures 35D, 35E:
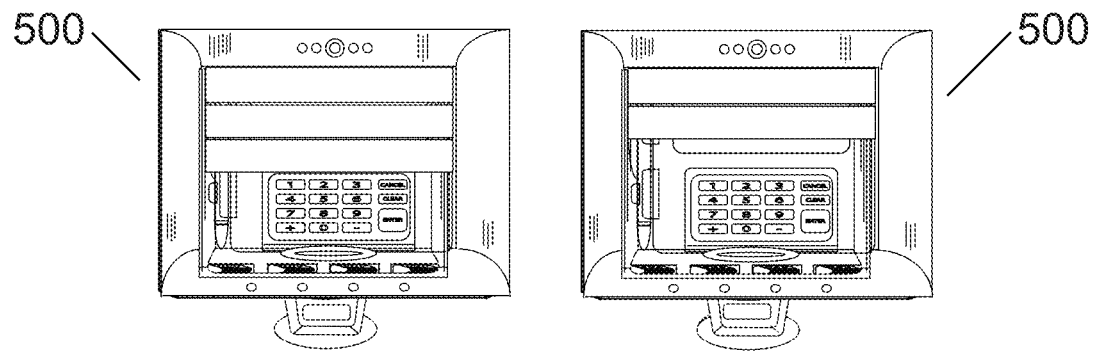

FIG. 35D reveals a front view of a POS chamber with three access panels.

FIG. 35E reveals a front view of a POS chamber with four access panels retracted.

Figures 35F, 35G:
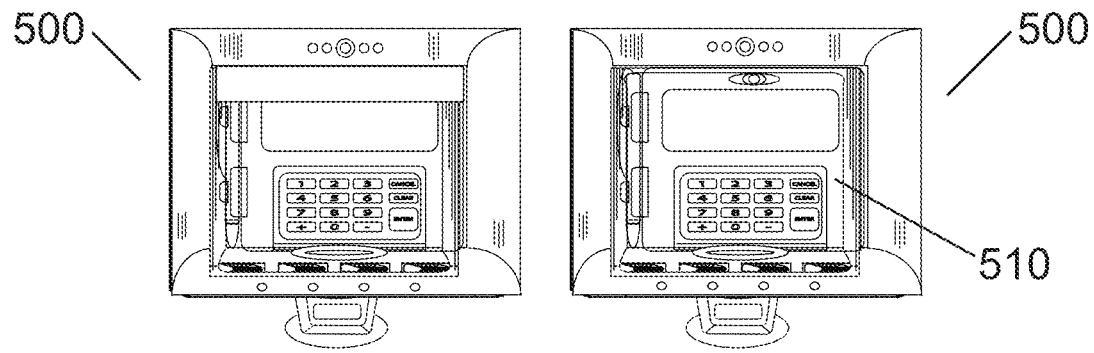

FIG. 35F reveals a front view of a POS chamber with five access panels retracted.

FIG. 35G reveals a front view of a POS chamber with six access panels retracted.

Figure 36:
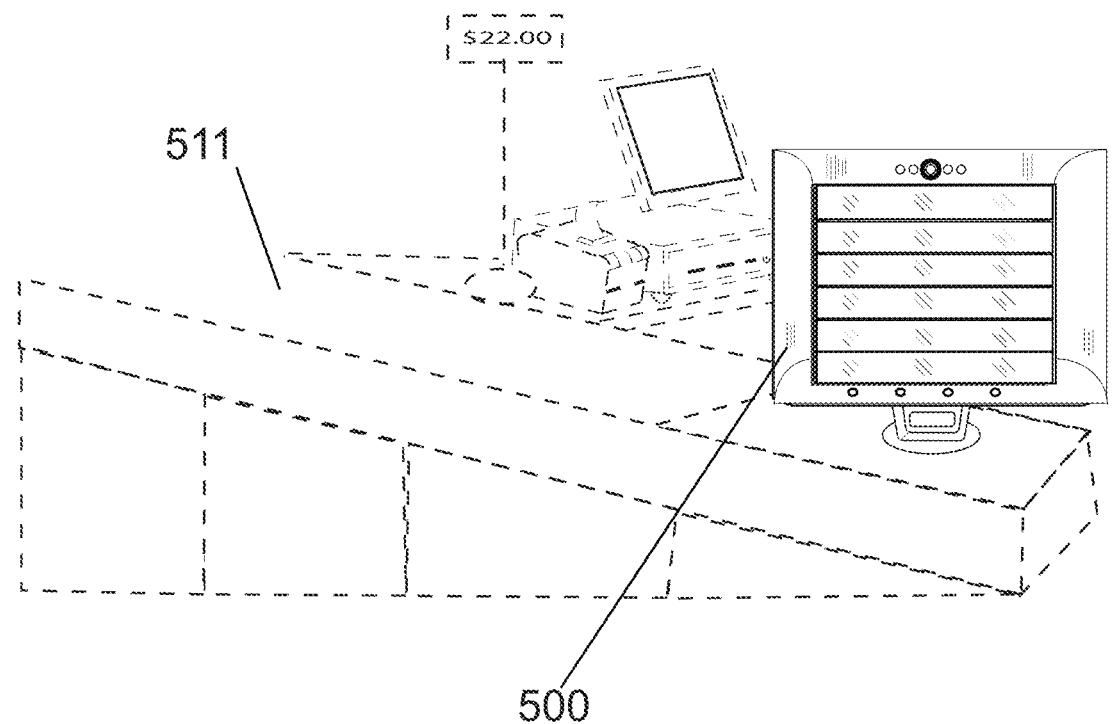

FIG. 36 illustrates a front perspective view of a POS chamber mounted at a retail checkout counter.

Figure 37A:
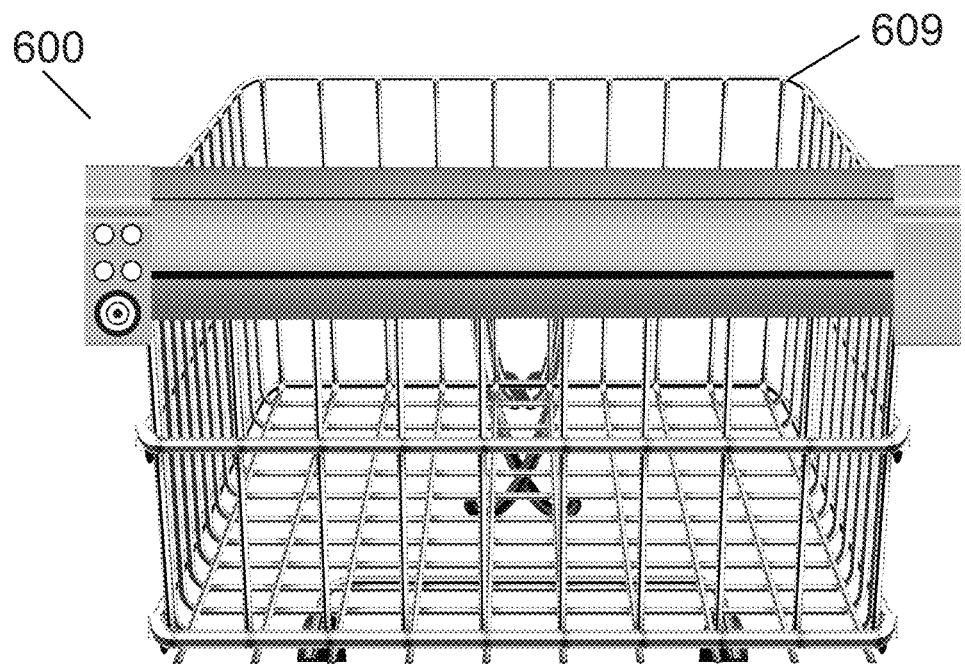

FIG. 37A depicts a front view of a shopping cart cylindrical germ decontamination chamber ("herein also referred to as "SC chamber") adjacent to a shopping cart.

Figure 37B:
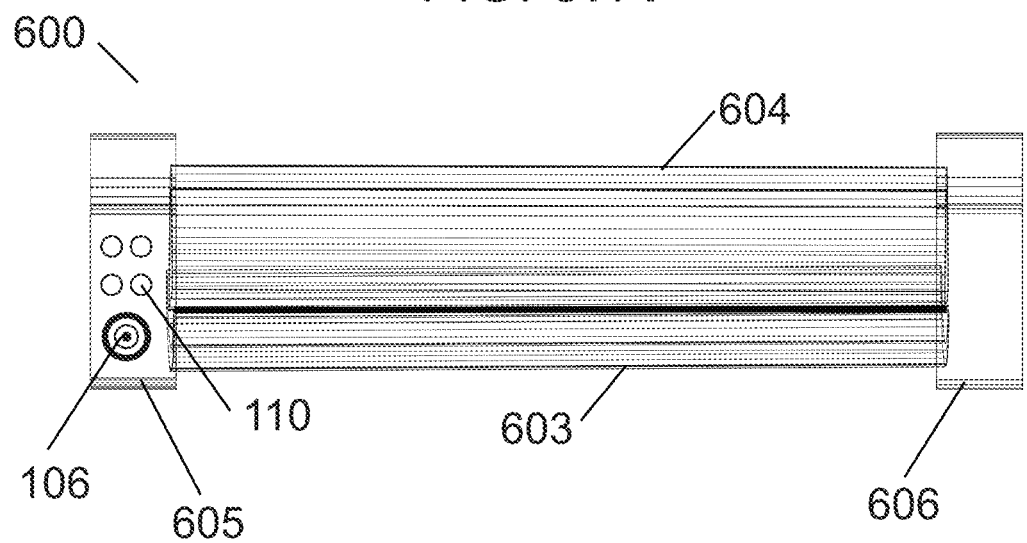

FIG. 37B shows a front view closeup of an SC chamber, access sensor, and status lights.

Figure 38A:
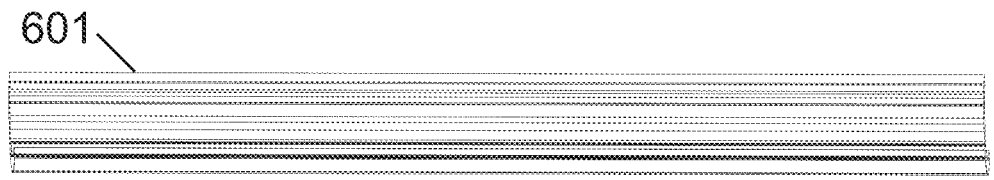

FIG. 38A portrays a front view of a SC chamber baseplate.

Figure 38B:
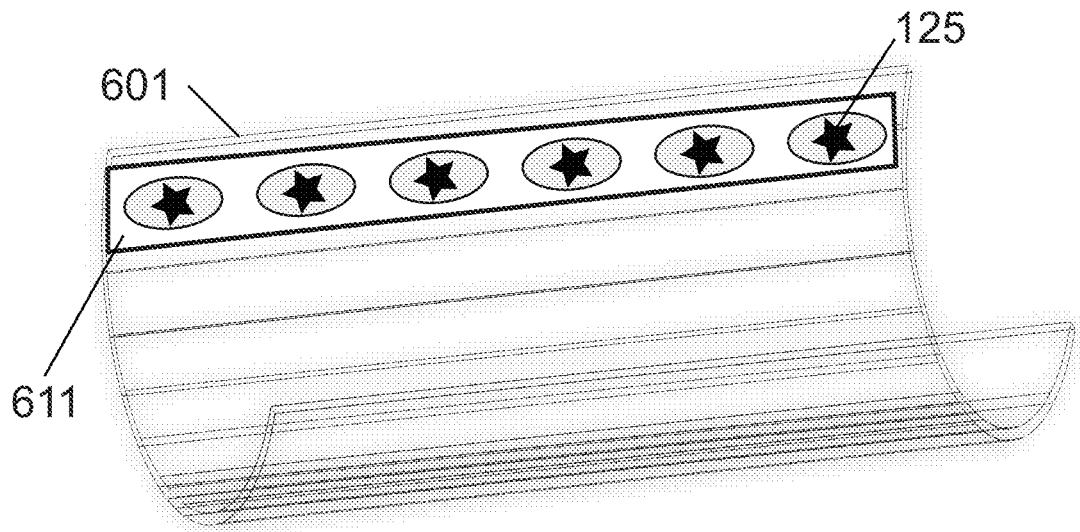

FIG. 38B represents a top perspective view of a SC chamber baseplate and UV-C.

Figure 39A:
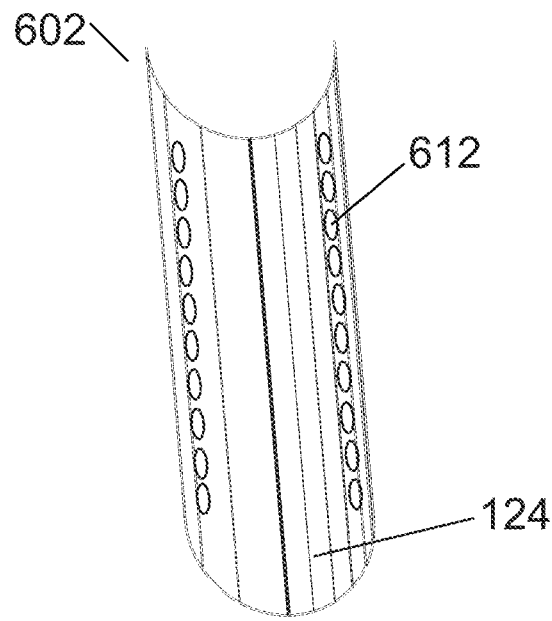

FIG. 39A exhibits an elevated side view of a SC chamber baseplate cover with UV-C cutouts.

Figure 39B:
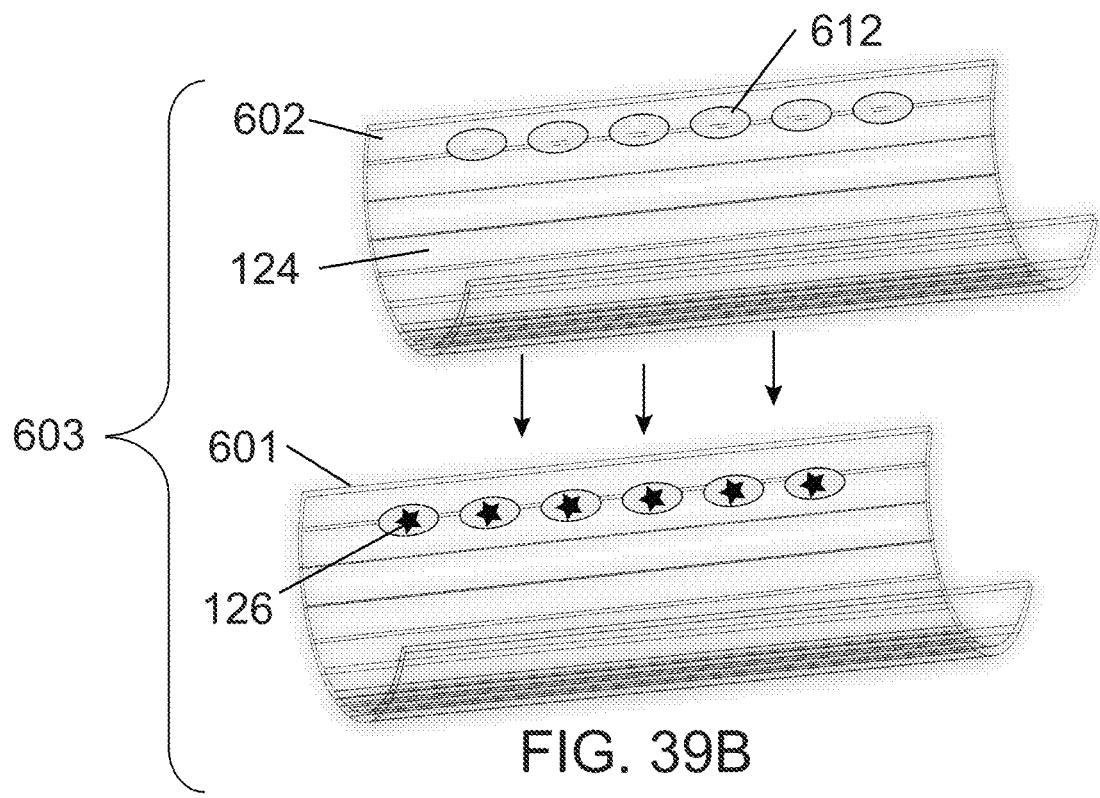

FIG. 39B displays an elevated front perspective closeup exploded view of a SC chamber baseplate cover projected into position over the SC chamber baseplate collectively forming the undercarriage assembly.

Figure 40A:
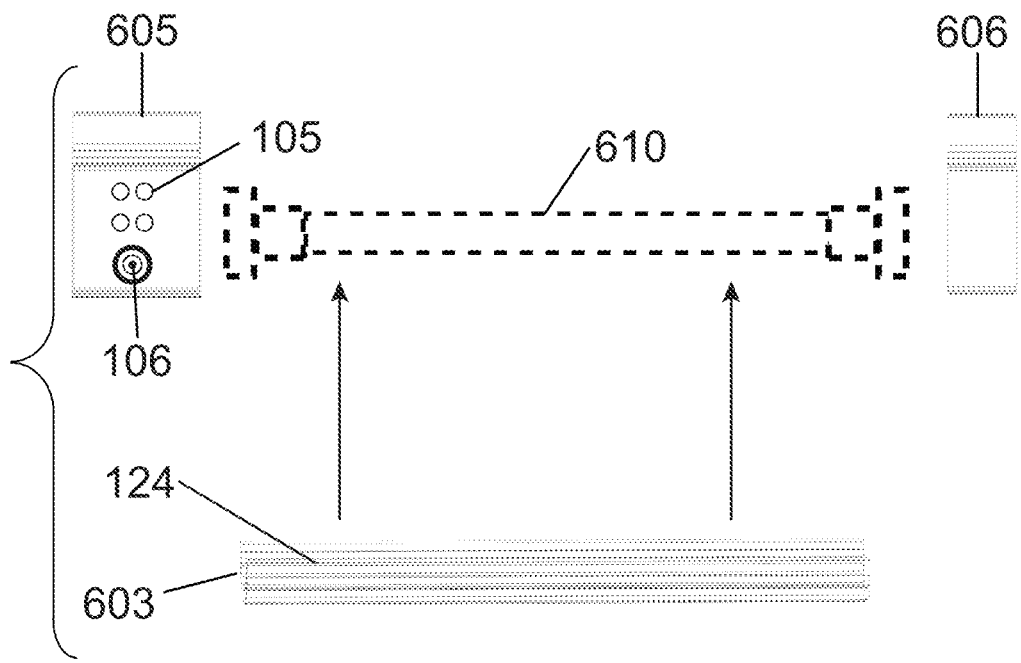

FIG. 40A presents a front exploded view of the undercarriage assembly projected adjacent to a shopping cart handle and left and right housing of the SC chamber.

Figure 40B:
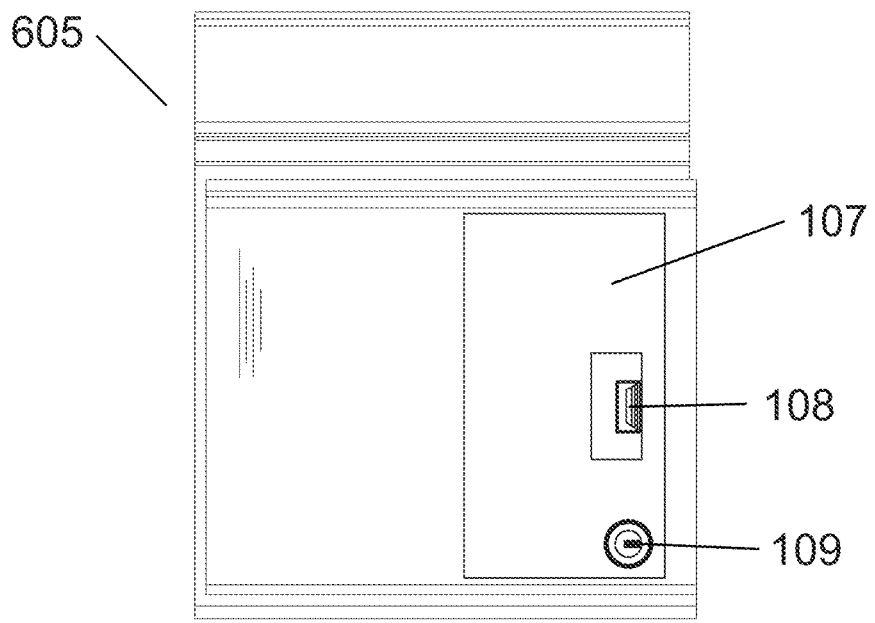

FIG. 40B depicts a side perspective view of an assembled left housing and battery access panel.

FIG. 41A illustrates an elevated side perspective exploded view of the components comprising the left housing of the SC chamber.

FIG. 41B exhibits a side closeup view of the left housing and battery access panel.

Figure 42A:
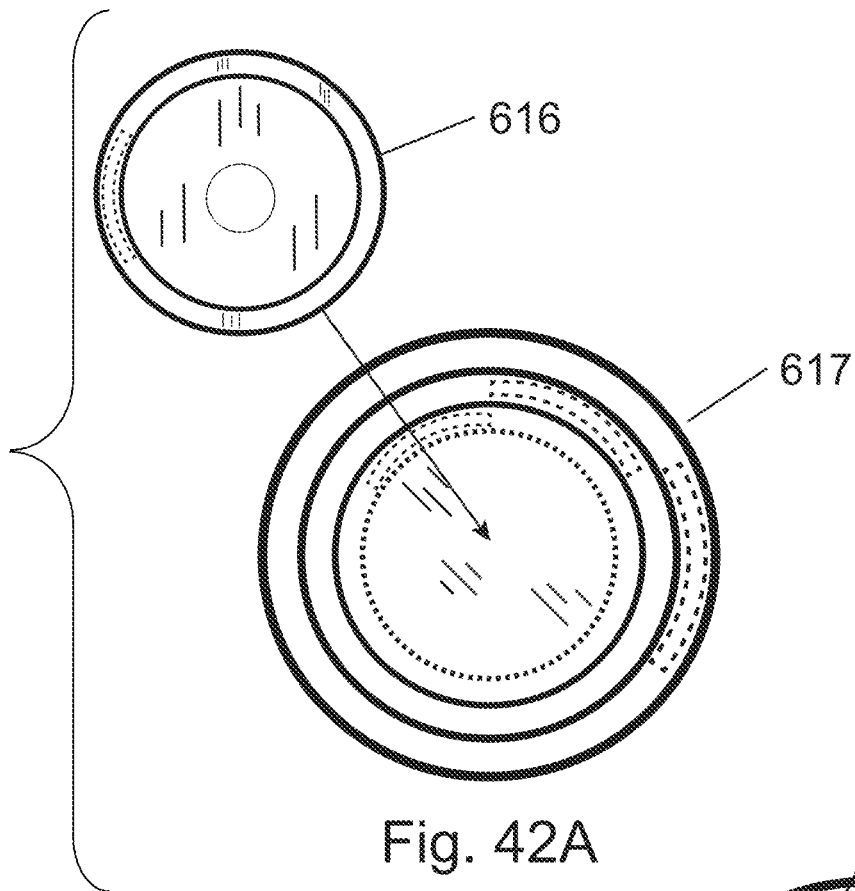

FIG. 42A shows a side perspective exploded view of the drive hub (herein also referred to as "hub") projected adjacent to the driven drum (herein also referred to as "drum") of the left housing.

Figure 42B:
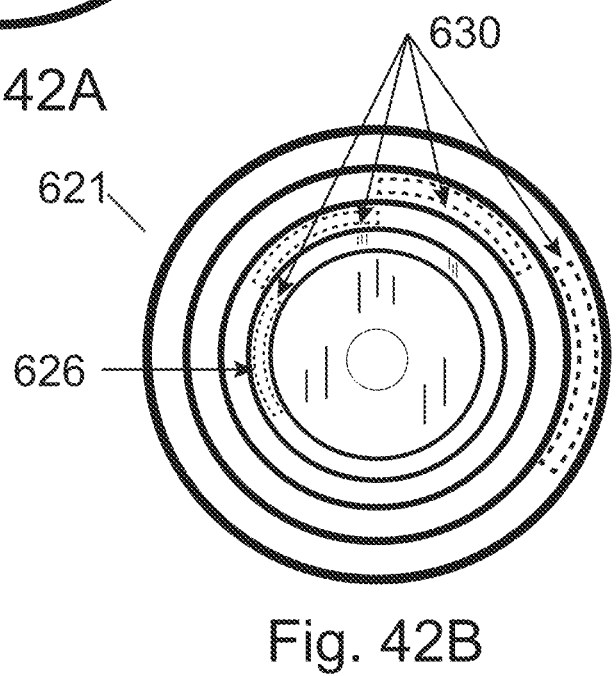

FIG. 42B portrays a side closeup view of the left hub and drum assembly (herein also referred to as "H&D assembly") in the closed position.

Figure 43A:
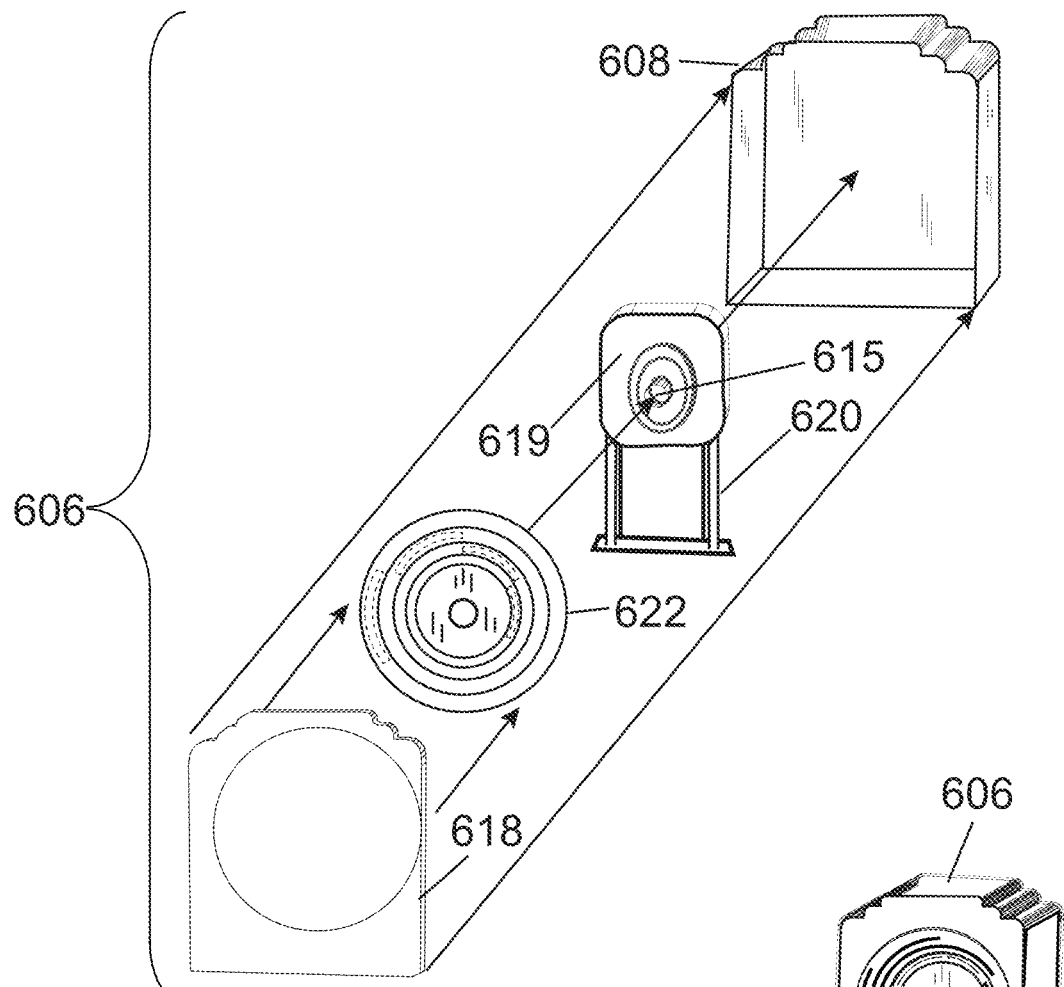

FIG. 43A depicts an elevated side perspective exploded view of the components comprising the right housing of the SC chamber.

Figure 43B:
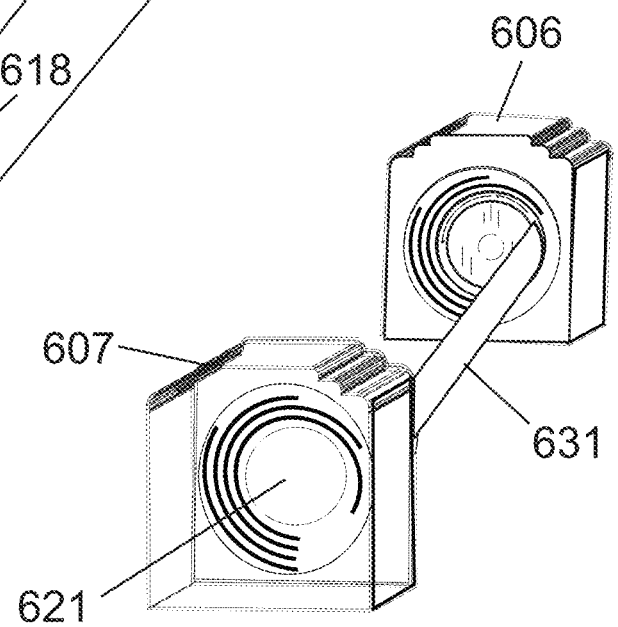

FIG. 43B presents a side perspective view of the oppositely disposed and parallel left housing and right housing adjacent to a cyl drive panel (herein also referred to as "cyl panel #1") in the closed position.

Figure 44A:
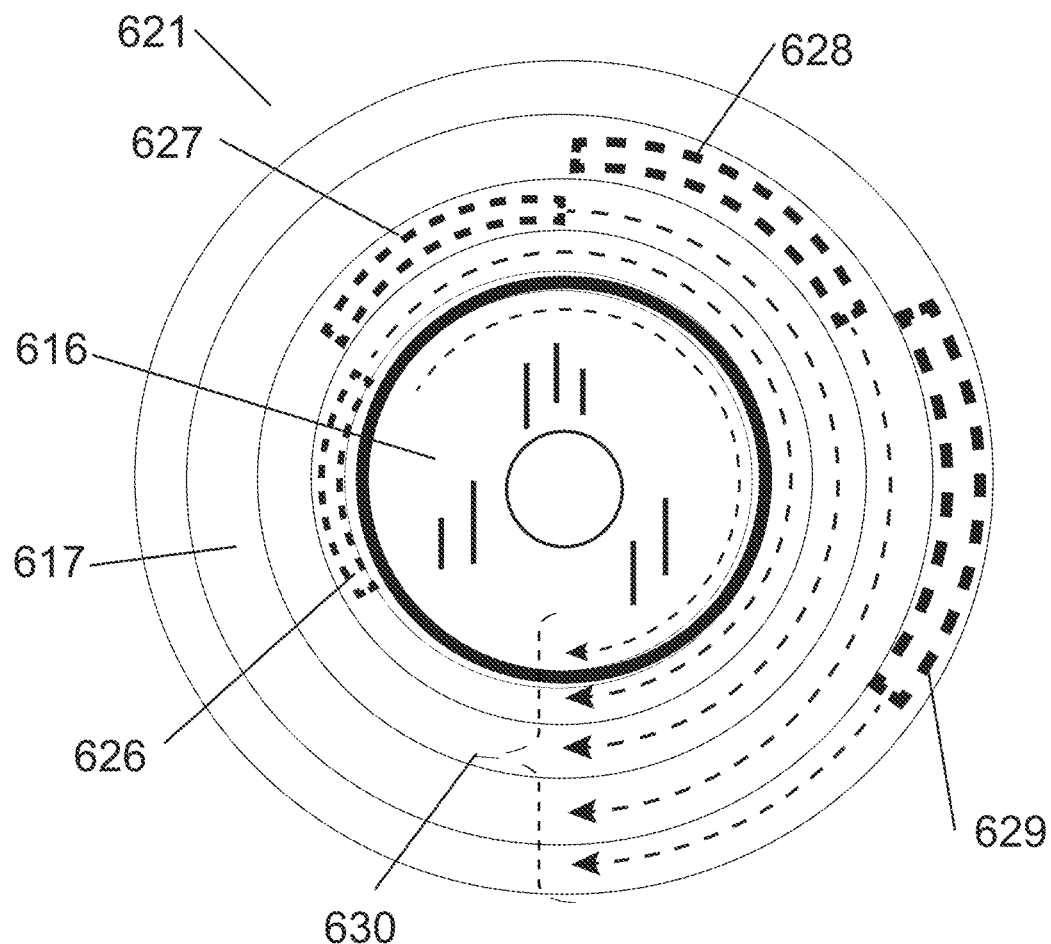

FIG. 44A illustrates a side closeup view of the left hub and drum assembly and cylindrical rail group (herein also referred to collectively as "cyl rails" or "rails") in the closed position with projection lines detailing the rotation of the drive hub and drum components during the retraction process.

Figure 44B:
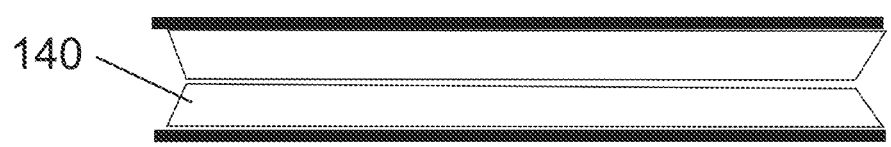

FIG. 44B depicts a side closeup view of the nylon glide.

FIG. 45A presents a top perspective view of a cylindrical access panel.

FIG. 45B illustrates a bottom perspective view of a cylindrical access panel.

FIG. 45C represents a bottom perspective exploded view projecting the interface of three access panels with cylindrical drive clips (herein also referred to as "cyl drive clips") and cylindrical channel guides (herein also referred to as "cyl channel guides").

Figure 46A:
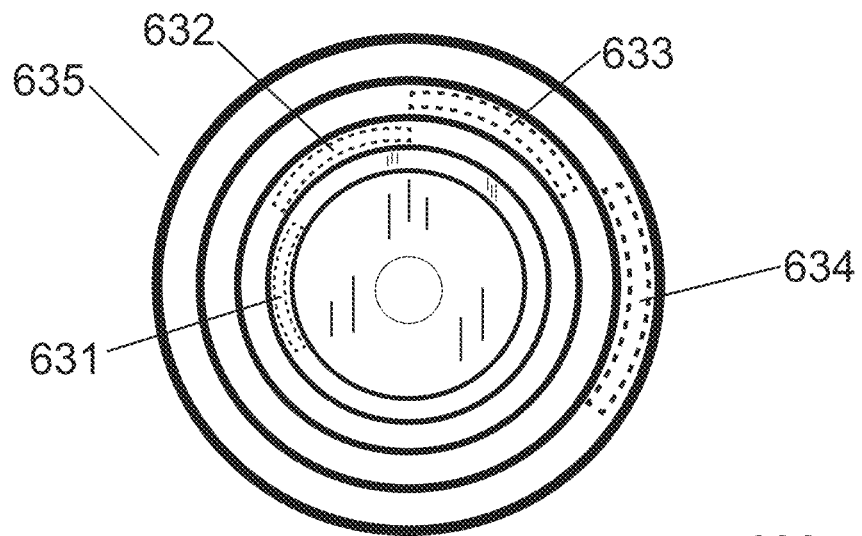

FIG. 46A shows a side closeup view of the left hub and drum assembly in hub position "0" (closed).

Figure 46B:
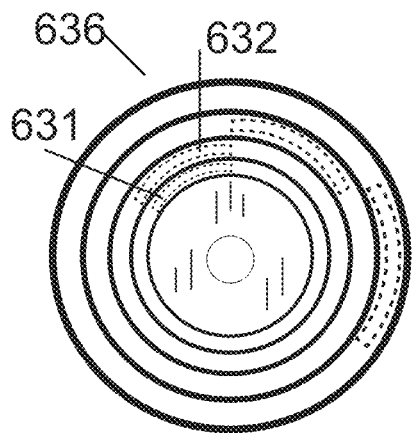

FIG. 46B shows a side closeup view of the left hub and drum assembly in hub position "1" (one panel retracted).

Figure 46C:
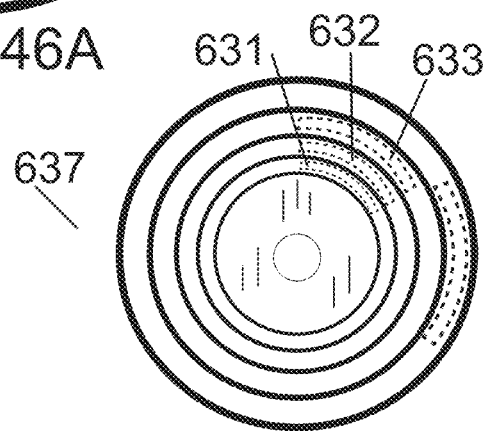

FIG. 46C shows a side closeup view of the left hub and drum assembly in hub position "2" (two panels retracted).

Figure 46D:
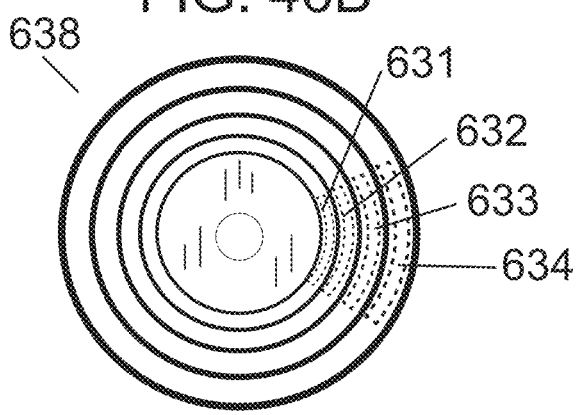

FIG. 46D shows a side closeup view of the left hub and drum assembly in hub position "3" (three panels retracted).

Figure 46E:
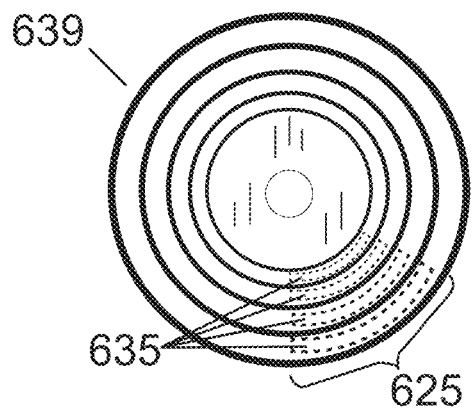

FIG. 46E shows a side closeup view of the left hub and drum assembly in hub position "4" (access panels open).

Figures 47A, 47B, 47C:
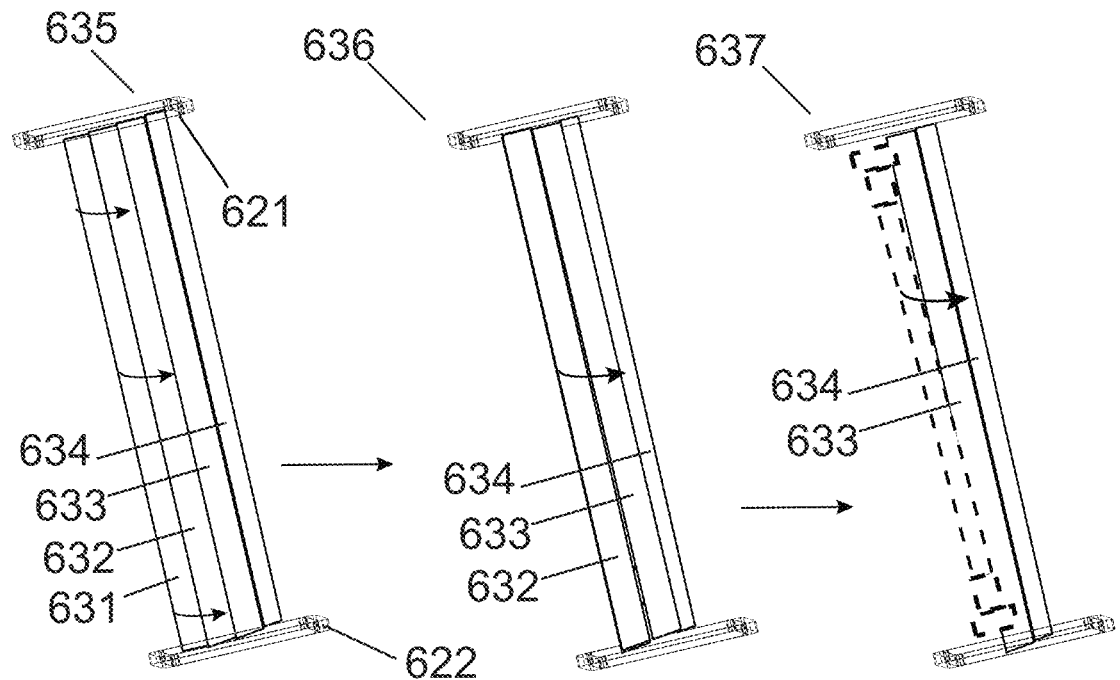

FIG. 47A displays an elevated top view of the panels of an SC chamber in a closed state (hub position "0").

FIG. 47B displays an elevated top view of the panels of an SC chamber with one access panel retracted (hub position "1").

FIG. 47C displays an elevated top view of the panels of an SC chamber with two access panels retracted (hub position "2").

Figures 47D, 47E:
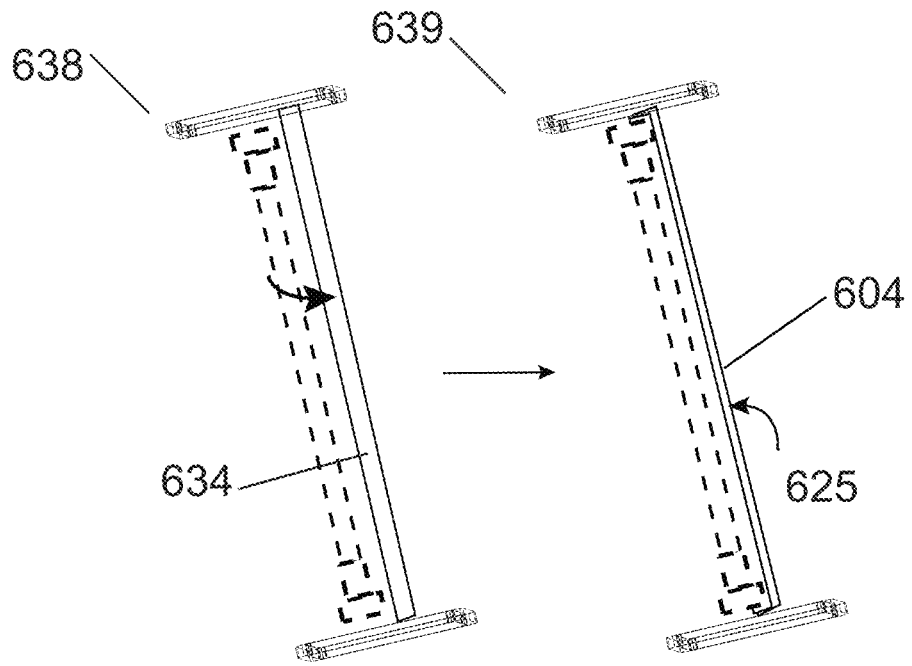

FIG. 47D displays an elevated top view of the panels of an SC chamber with three access panels retracted (hub position "3").

FIG. 47E displays an elevated top view of the panels of an SC chamber with all access panels retracted (hub position "4") providing access to the sterilized shopping cart handle.

Throughout the drawings and the detailed description, the same reference numerals can refer to the same elements. The drawings may not be to scale, and the relative size, proportions, and depiction of elements in the drawings may be exaggerated for clarity, illustration, and convenience.

DETAILED DESCRIPTION

The terminology used herein is for the purpose of describing particular embodiments only and is not intended to be limiting of the invention. As used herein, the term "and/or" includes all combinations of one or more of the associated listed items. As used herein, the singular forms "a," "an," and "the" are intended to include the plural forms as well as the singular forms unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification should be read with the understanding that such combinations are entirely within the scope of the invention.

New methods and devices to decontaminate germs from human touch point inanimate objects, hereafter referred to as "fomites", and to seal the fomite from airborne pathogens between use to prevent the spread of infectious diseases are discussed herein. For the purpose of the present invention, examples of fomites include but are not limited to door handles, restroom stall latches, deadbolts, gas pump handles, retail point-of-sale (POS) terminals, automatic teller machines, shopping cart handles, elevator control panels, public telephones, paper towel extraction levers, toilet handles and seats, and the like. In the following description, for the purposes of explanation, numerous specific details are set forth to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or descriptions below.

In accordance with an embodiment, a method of sterilizing and sealing a human touch point fomite is provided. A device comprising a solid exterior shell is adjacent with or attaches to the fomite and forms a chamber to seal the fomite from airborne pathogens. The shell comprises a cutout in the front and an open rear. The front cutout is optimally located in front of the touch point and is sealed with one or more retractable panels which, when retracted, provide a user access to the fomite. The rear of the exterior shell is sealed either by a baseplate or directly to the structure to which the fomite is attached. After each use, a germicidal process is completed to kill/inactivate the microorganisms; subsequently, the device remains sealed, only opened upon user-detection through sensor technology, to prevent airborne pathogens from attaching to the fomite between use.

In accordance with an embodiment, an apparatus (also referred to as "device" or "chamber") configured to decontaminate and seal human touch point fomites from germs is provided. The device comprises a solid exterior front shell which is positioned over the fomite and secured either adjacent with or attached to the fomite to form a sealed chamber. The exterior shell features an opening in front of the fomite, which is sealed by one or more retractable panels, and another in the rear which is fully or partially surrounded by a baseplate. The interior of the chamber is coated with a UV-C reflective material such as aluminum foil, PTFE, UV-reflective paint, or any similar substance proven to maximize UV reflectivity. The chamber interior also comprises one or a plurality of ultraviolet-C wavelength LED semiconductor chips (hereafter referred to as "UV-C", "UV-C source", or "chips"), optimally mounted at a fixed or adjustable angle to the baseplate, and/or upper housing assembly including the retractable panels to ensure proper coverage and the most effective placement, surround the fomite to kill adjacent germs within seconds after each interaction with a user through ultraviolet germicidal irradiation (herein also referred to as "UVGI"). In this embodiment, the UV-C is/are preferably delivering their dose at an optimal wavelength of 265 nm. The device remains sealed after the UVGI cycle to prevent airborne pathogens from contaminating the fomite between users. Upon detection of a user through sensor technology, the access panels retract to provide unimpeded access to the germ-free fomite, then are closed after use to perform the UVGI cycle and seal the fomite from airborne pathogens once again.

In accordance with certain embodiments, the device may be comprised of a single alternative UV-C wavelength in place of 265 nm, such as far UV-C ranging between 207-222 nm, to target a specific germ or germs which may be optimally inactivated at alternative wavelengths. In accordance with certain embodiments, the device may be comprised of a multi-wavelength UV-C array within the chamber to target varying classes of germs which are optimally inactivated at alternative wavelengths. For example, some protein-based germs are optimally killed at 220 nm instead of 265 nm while others may be more susceptible to wavelengths of 280 nm. In accordance with certain embodiments, the chamber of the device may be comprised of ozone-producing UV operating at a wavelength of 185 nm which can be deployed in conjunction with non-ozone-producing UV-C or as a stand-alone germicidal solution. In accordance with certain embodiments, the UV light source within the chamber could be LED, pulsed-xenon, low-pressure mercury, or any other suitable UV light delivery format. In accordance with certain embodiments, the device may be comprised with a single self-contained housing without a rear baseplate.

In accordance with certain embodiments, a germ decontamination system is also provided comprising any of the germ decontamination apparatuses described herein configured to be integrated into an apparatus or product comprising a fomite. For the purpose of the present invention, examples of an apparatus or product comprising a fomite include but are not limited to a door, a restroom stall, a deadbolt, a gas pump, a retail point of-sale (POS) terminal, an automatic teller machine, a shopping cart, an elevator, a public telephone, a paper towel dispenser, a computer keyboard, a toilet, and the like.

The present invention will now be described by referencing the appended figures representing preferred embodiments. FIGS. 1A-17E describe an embodiment of a germ decontamination chamber for use with a broad spectrum of human touch point fomites.

Figure 1A:
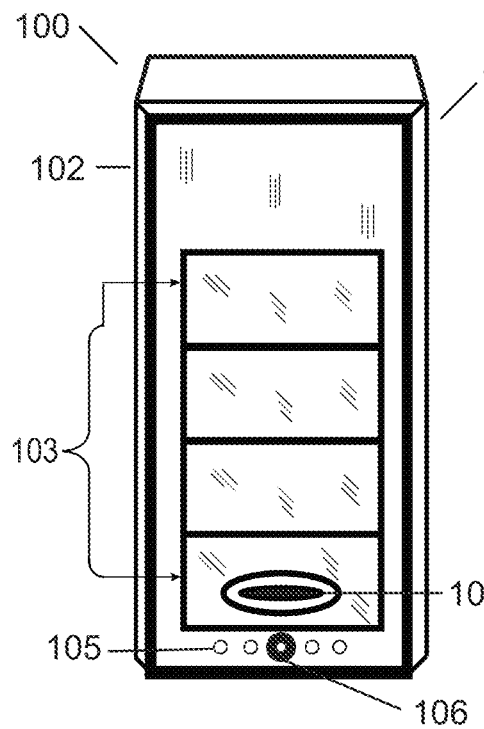
FIG. 1A presents an elevated front view of one example of a germ decontamination chamber for human touch point fomites according to various embodiments of the present invention.
Figure 1B:
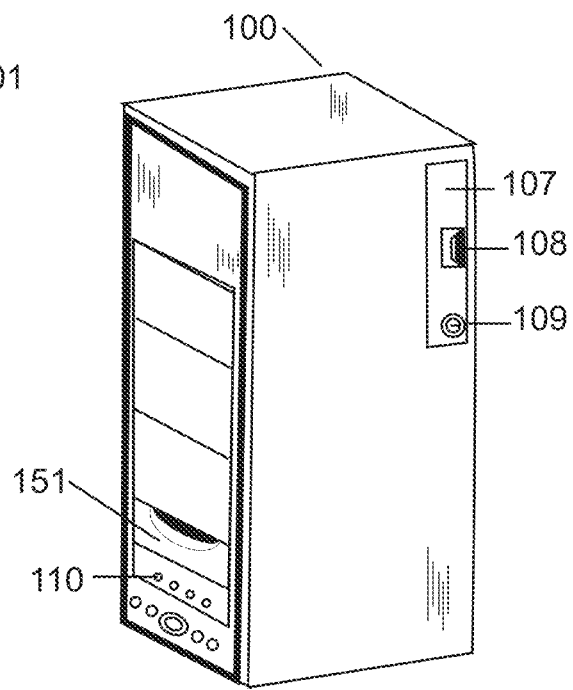
FIG. 1B depicts an elevated side perspective view of the right side of a germ decontamination chamber comprising the battery components and a partially retracted drive panel.
Figure 1C:
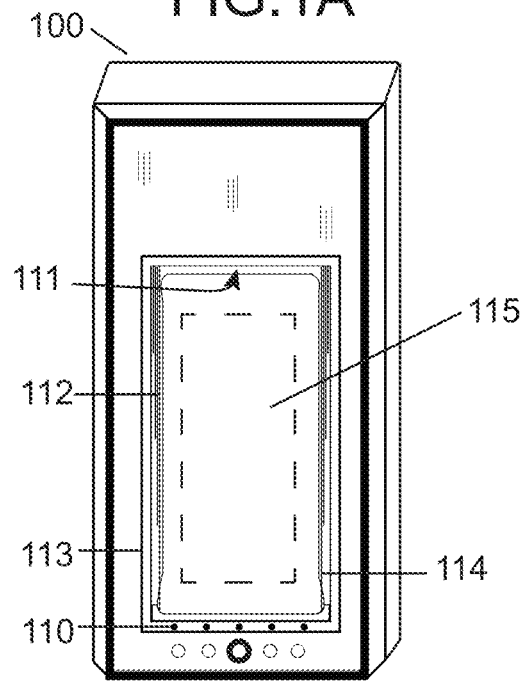
FIG. 1C illustrates an elevated front perspective view of the front interior including access panel rails and obstruction sensors.
Figure 1D:
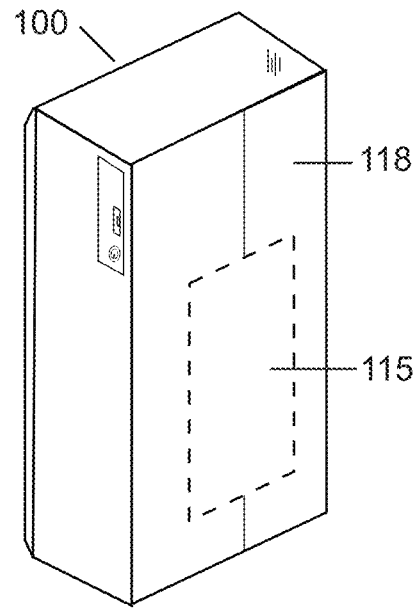
FIG. 1D shows an elevated rear perspective view of the baseplate mounted to a germ decontamination chamber.

FIGS. 1A-1D present a front view, side perspective view, front perspective view, and elevated rear perspective view, respectively, of the germ decontamination chamber (herein also referred to as "chamber" or "device") 100 for human touch point fomites 115. FIG. 1A presents a front view of the exterior of a germ decontamination chamber 100 and identifies the exterior elements of the upper housing assembly 101 (herein also referred to as "UHA"). The chassis 102 is the outer shell of the chamber 100 which comprises a center cutout to provide frontal access to the fomite 115 and an open rear area to allow it to be positioned over the fomite 115 (FIG. 1D) and adjacent to the baseplate assembly 118 at the rear of the chamber 100 (FIG. 1D). The chassis 102 can be constructed of plastic, aluminum, carbon fiber, fiberglass, or any other suitable material. Behind the cutout, the access panel group 103 comprising an aggregation of four access panels for the device 100 (herein also referred to as "access panels" or "panels") is positioned to seal the front of the chamber 100 during the ultraviolet germicidal irradiation (herein referred to as "UVGI" or "UVGI cycle") cycle and when access is not required to prevent re-contamination through airborne microorganisms.

FIG. 1A also depicts an embedded emergency handle 104 located in proximity to the bottom of the access panels 103 to raise and lower them in the event of power loss or mechanical malfunction. An access sensor 106 is located below the access panels 103 to identify the presence of a user and trigger the opening of the access panels 103. Two chamber status lights 105 are located on each side of the access sensor to visually report system readiness, i.e., power on, UVGI progress, malfunction, and battery status.

FIG. 1B, portrays a side perspective view of the chamber 100 with access panel #4 151 (herein also referred to as the "drive panel") partially retracted to reveal the obstruction sensors 110 as are also exhibited in FIG. 1C. The right side of the chamber is comprised of the battery access door 107, battery release latch 108 (herein also referred to as "battery latch"), and battery lock 109. In preferred embodiments, the battery 126 can be lithium nickel manganese cobalt oxide (Li-NMC), lithium ion ("Li-ION), or any other long-lasting type which will optimize the performance of the chamber. In certain embodiments, the device can be powered by AC connection, wireless, solar, or any other means which will provide sufficient power for which it to operate.

FIG. 1C depicts a front view of the chamber 100 with the access panels 103 raised into the panel bay 111 (not visible) revealing the peripheral components of the access panel assembly 139 (herein also referred to as "AP assembly") comprising the access panel frame 113 (herein also referred to as "AP frame"), embedded panel rails 112 (herein also referred to as "rails" or individually as "rail"), support bridge 114, and the fomite 115 as indicated by the rectangular broken lines. FIG. 1C additionally identifies the location of the obstruction sensors 110 which detect the presence of a user or foreign object during the closing of the access panels 103, prompting the chamber 100 to reverse the closing procedure and retract the access panels 103 into the panel bay 111. The rear of the chamber 100 is presented in the elevated view of FIG. 1D comprising the baseplate assembly 118 and an example of a fomite 115 demarcated by the rectangular broken lines.

Figure 2:
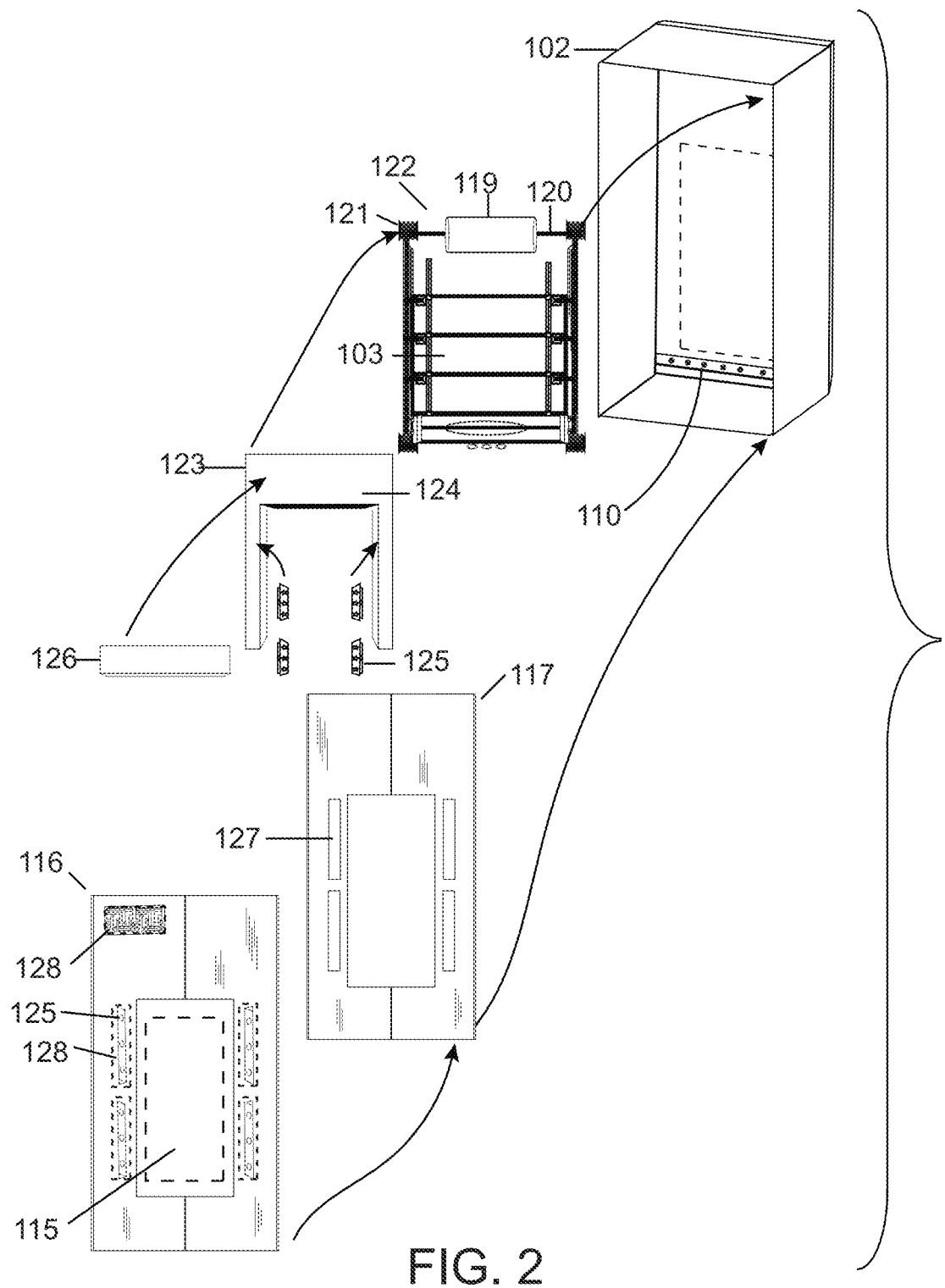
FIG. 2 portrays an elevated rear exploded view of the components comprised within the upper housing assembly and baseplate assembly.

Now referring to FIG. 2, an elevated rear perspective exploded view exhibits the chamber's 100 main components comprised within the upper housing assembly 101 and the baseplate assembly 118. Viewing from the upper right diagonally to the lower left, a rear view of the chassis 102 is exemplified. A drive assembly 122 comprising the drive motor 119, drive shaft 120 (herein also referred to as "shaft"), pulley 121, and access panels 103 is mounted to align the access panels 103 to the front center opening of the chassis 102. The u-shaped shroud 123 comprising a UV-reflective coating 124, is secured over the drive motor 119 and the shroud's legs 123 extend to cover the sides of the drive assembly 122. UV-C 125 is mounted adjacent to the vertical arms of the shroud, the position of which delivers a direct UVGI dose to the front and/or sides of the fomite 115. In certain embodiments, UV-C 125 may be mounted in alternate locations within the upper housing assembly 101 including on the rear of the access panels 103 facing the fomite 115 to deliver the optimal UVGI dose. The battery 126 is secured behind the top of the shroud 123 to complete the major components of the upper housing assembly 101. The baseplate cover 117 comprised of UV-C cutouts 127 attaches to the rear of the upper housing assembly 101 followed by the baseplate 116, comprised of a microcontroller 128 and UV-C 125, which is positioned adjacent to the fomite 115. The combined baseplate cover 117 and baseplate 116 form the baseplate assembly 118 as shown in FIG. 3D.

Figure 3A:
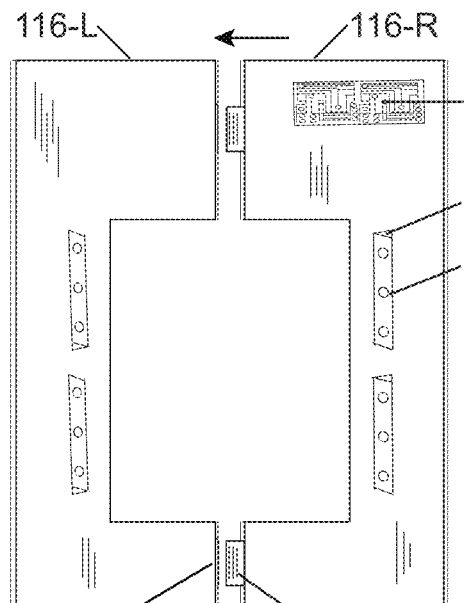
FIG. 3A shows a front view of the baseplate of a germ decontamination chamber comprising the microcontroller and the mounted UV-C source.
Figure 3B:
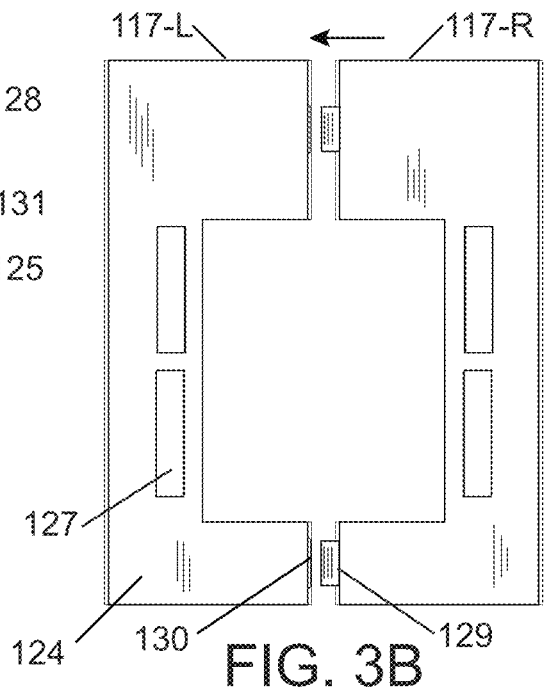
FIG. 3B portrays a front view of a baseplate cover.
Figure 3C:
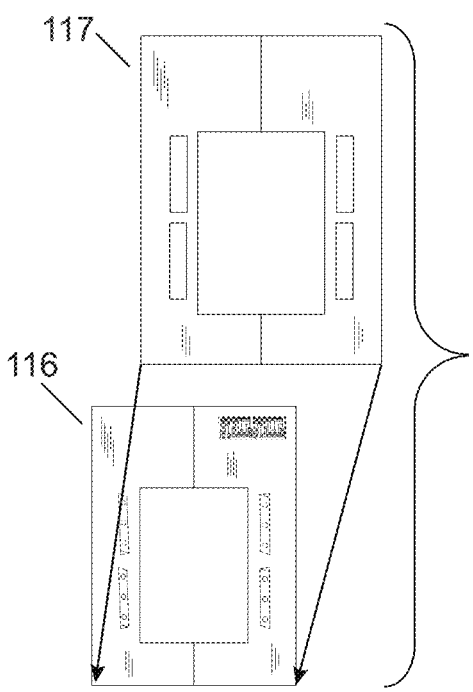
FIG. 3C represents an exploded front view of the placement of the baseplate cover over the baseplate.
Figure 3D:
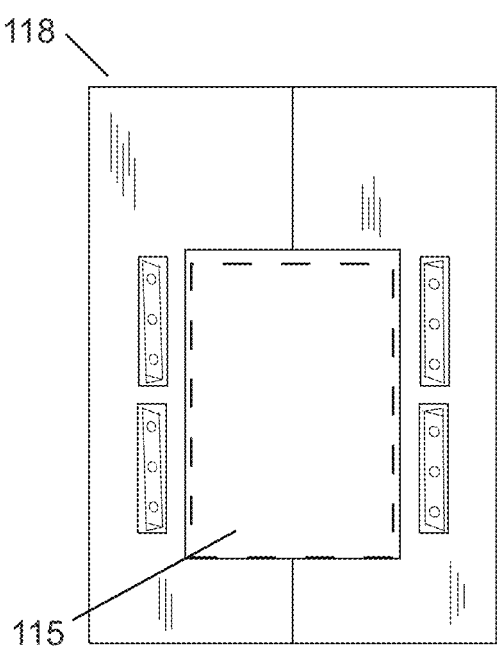
FIG. 3D exhibits a front view of the baseplate cover combined with the baseplate to form the baseplate assembly.

Now referring to FIGS. 3A-D, FIG. 3A and 3B depict a front view of the baseplate 116 and baseplate cover 117, respectively, each separated into two sides, L&R. The right side of the baseplate 116-R and baseplate cover 117-R each comprise top and bottom interlocking male tabs 129 which connect to the female tab receivers 130 on the left side (collectively referred to herein as "interlocking tabs") of the baseplate 116-L and baseplate cover 117-L. This allows the baseplate 116 and baseplate cover 117 to be mounted adjacent to the base of the fomite 115 as a single combined unit to form the baseplate assembly 118 as shown in FIG. 3D.

Returning to FIG. 3A, the baseplate 116 comprises a microcontroller 128 to manage the power, sensors, mechanical, and all programmatic functions of the chamber 100. In the preferred embodiment, the baseplate 116 also comprises one or more UV-C LED chip(s) 125 (herein also referred to as "UV-C", "UV-C source", or "chip(s)") which is/are embedded within or affixed to an adhesive strip which is secured to the adjustable UV-C mounting stand 131. The UV-C mounting stand 131 is then attached adjacent to the baseplate 116. The UV-C 125 affixed to the baseplate allows the wavelength to be directed toward the rear and sides of those fomites 115 which receive some or all human contact in those areas instead of the front, such as door handles 155 (FIG. 15B) which receive a small percentage of contact to the front or face. In an alternative embodiment, the UV-C mounting stand 131 is eliminated allowing the UV-C 125 to be affixed directly to the baseplate 116.

Continuing to reference the UV-C 125 in FIG. 3A, the preferred embodiment is for the UV-C LED's 125 to perform precisely at 265 nm, universally recognized as the optimal wavelength for ultraviolet sterilization. Although virtually all germs are proven to be inactivated by UV-C 125 at a wavelength of 265 nm, the optimal wavelength for some protein-based germs is 220 nm while others are most quickly inactivated closer to 280 nm. Therefore, an alternative embodiment calls for a multi-wavelength or multimodal UV-C 125 array deployed throughout the inside of the chamber 100 and delivered in a pulse-format to specifically target certain classes of germs.

As depicted in FIG. 3B, the baseplate cover 117 is coated with a UV-reflective material or substance 124 such as PTFE reflectors, paint, aluminum foil or any other material or coating proven to enhance UV reflectivity. The baseplate cover 117 has UV-C cutouts 127 which are positioned directly above the UV-C 125 on the baseplate 116. In the preferred embodiment, the UV-C cutouts 127 are not covered, however, in certain embodiments they may be covered with a suitable translucent material to hermetically seal the UV-C 125 as required by the application.

The baseplate cover 117 overlays the baseplate 116, as shown in the front exploded projection view of FIG. 3C, and they collectively form the baseplate assembly 118, as shown in FIG. 3D. The baseplate 116 and baseplate cover 117 can be constructed of plastic, metal, or any other suitable material. While this is the preferred embodiment, alternative embodiments could be deployed to achieve the desired result such as a one-piece baseplate 116 and cover with a hollow core to allow placement through the fomite 115, a baseplate 116 without a cover, a single integrated baseplate 116 and cover, or other embodiments not mentioned herein.

Figure 4:
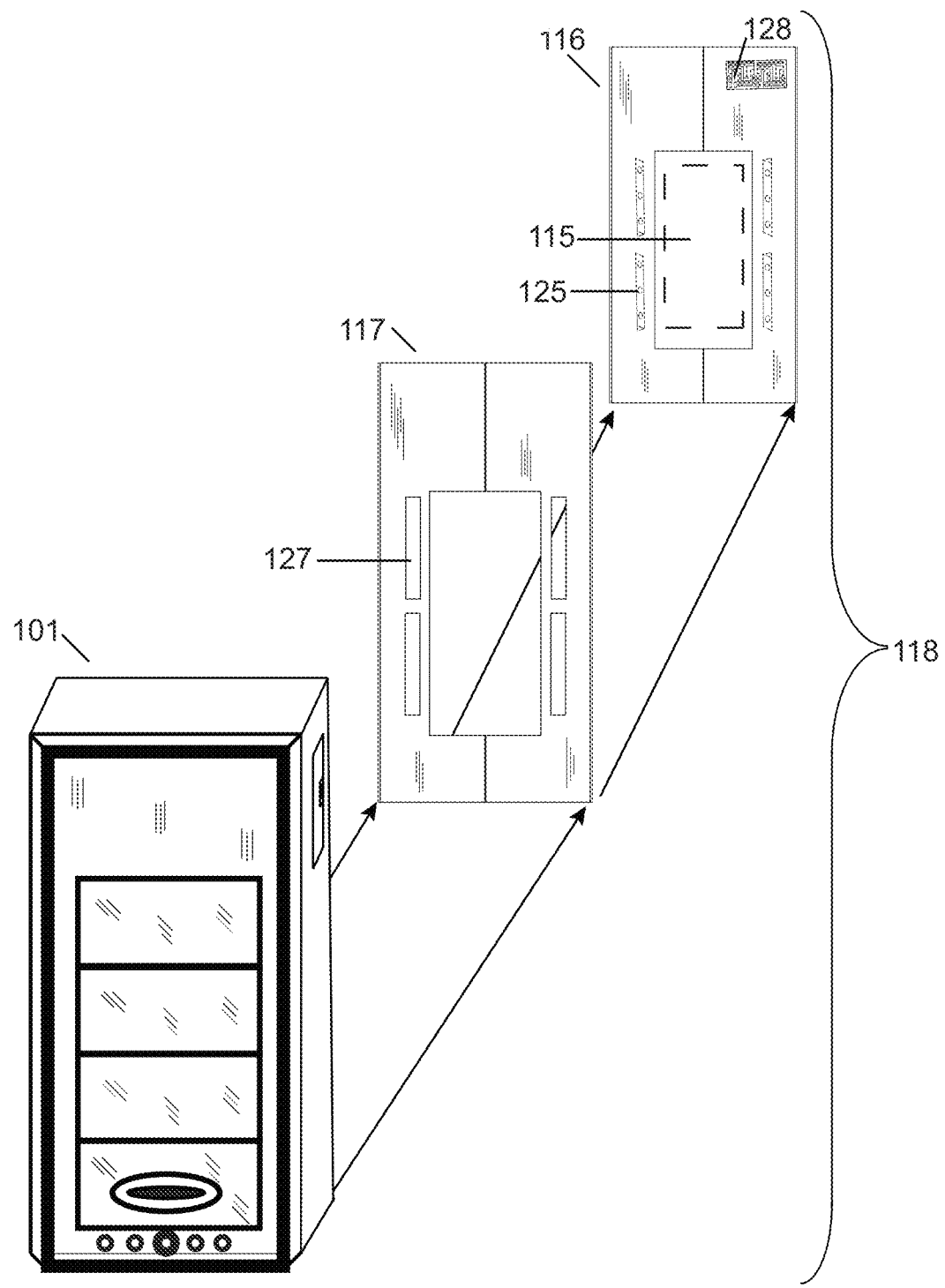
FIG. 4 exhibits an elevated front exploded view of the upper housing, baseplate cover, and baseplate.

Now referring to FIG. 4, an exploded front view of the upper housing assembly 101 ("UHA") projected upon the baseplate cover 117 and baseplate 116 is further detailed. The baseplate 116 with UV-C 125 and microcontroller 128 are mounted adjacent to a fomite 115 and the baseplate cover 117 with UV-C cutouts 127 attach to the baseplate 116 which collectively form the baseplate assembly 118 as depicted in FIG. 3D. The upper housing assembly 101 is then placed over the fomite 115 and secured to the baseplate assembly 118 to operationalize the chamber 100. In alternative embodiments, the upper housing 101 and baseplate assembly 118 are pre-assembled allowing the chamber 100 to be attached to the fomite 115 in one piece.

Figure 5:
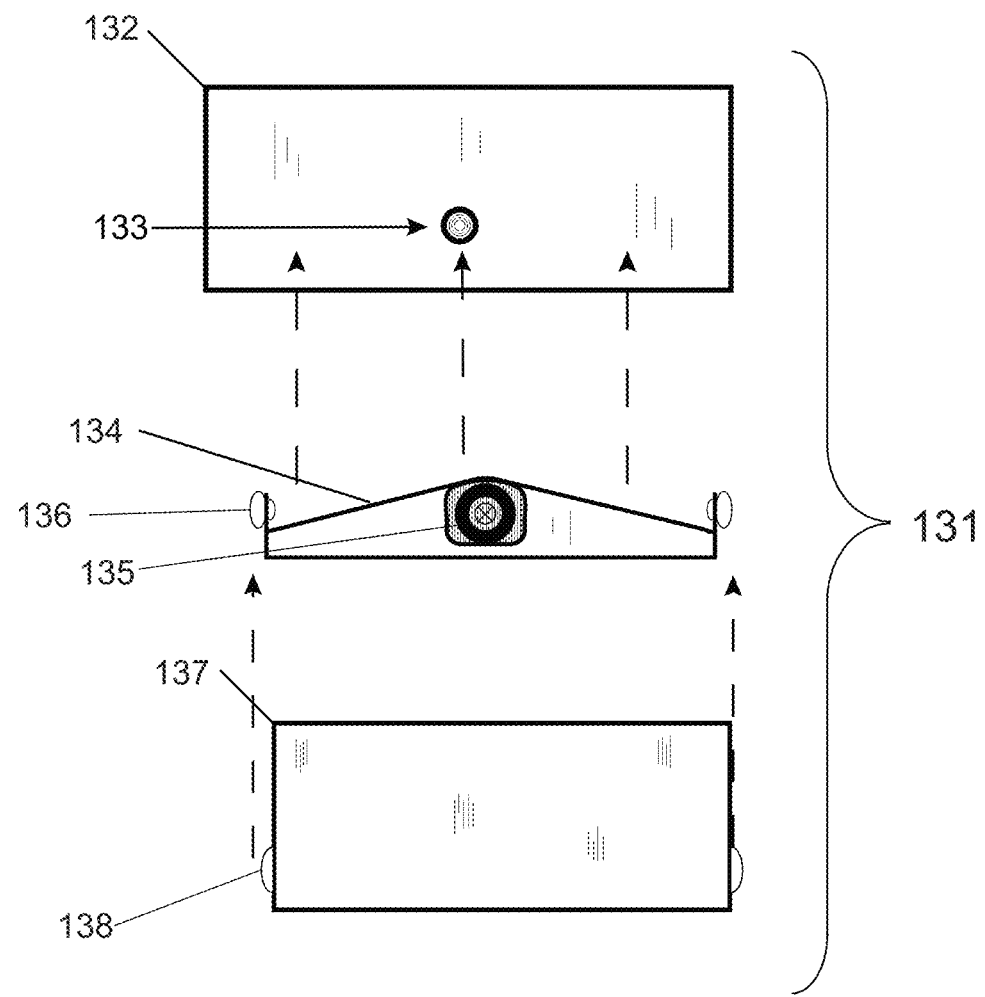
FIG. 5 reveals an exploded top view of the adjustable UV-C mounting stand components.

FIG. 5 exhibits a top exploded view of the UV-C mounting stand 131 comprising the mounting base 132, pivot plate 134, and the UV-C mounting tray 137 (herein also referred to as "UV-C tray", "tray", or "mounting tray"). As indicated by the broken line projection arrows, the pivot plate 134 connects to the mounting base 132 with the pivot plate screw and washer 135 being placed through the center of the pivot plate and into the threaded screw receiver 133 in the mounting base 132 allowing the pivot plate 134 to swivel horizontally. The UV-C tray 137 attaches to parallel and oppositely disposed pivot plate hinges 136 on each side of the pivot plate 134 using the mounting tray hinge screws 138 allowing the UV-C tray 137 to pivot forward and backward. With the UV-C mounting stand 131 affixed to the baseplate 116, the UV-C 125 can be positioned to deliver the UV-C dose at the optimal direction and angle to most efficiently perform its UVGI function.

Figure 6A:
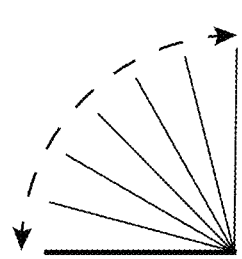
FIG. 6A displays a side view of pivot angles ranging from 15°-90° created by the UV-C mounting stand.
Figure 6B:
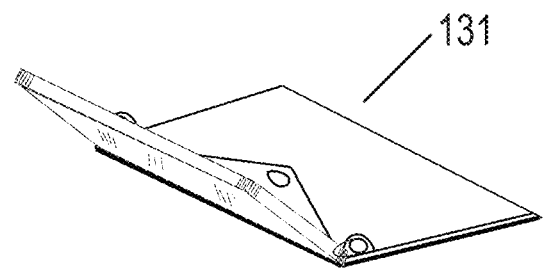
FIG. 6B illustrates a side perspective view of the UV-C mounting stand tilted at a 30° forward angle.
Figure 6C:
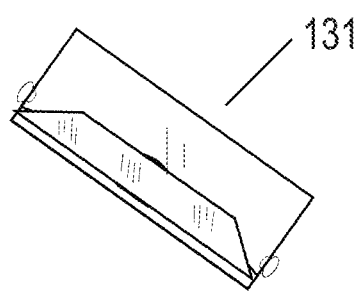
FIG. 6C depicts a top view of the UV-C stand tilted at a 75° angle.
Figure 6D:
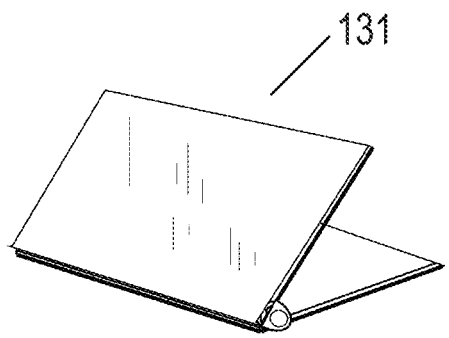
FIG. 6D shows a front perspective view of the UV-C mounting stand tilted at a 45° angle.
Figure 6E:
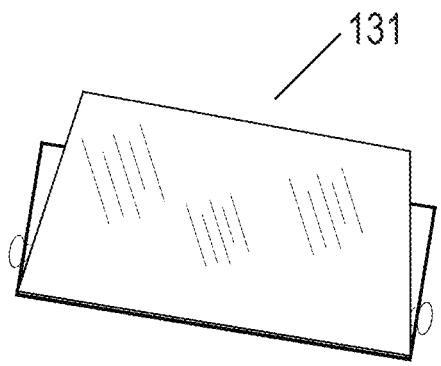
FIG. 6E portrays an elevated front view of the UV-C mounting stand tilted at a 15° angle.
Figure 6F:
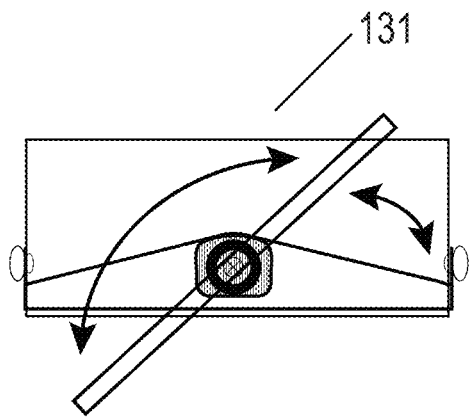
FIG. 6F presents a top view of the swivel action created by the UV-C mounting stand.

FIGS. 6A-F show the directional and angular flexibility provided by the UV-C mounting stand 131. FIG. 6A reveals a side view of pivot angles ranging from 15°-90° in 15° increments. FIG. 6B shows a front perspective view of a 30° forward angle, FIG. 6C displays a top view of a 75° tilt angle, FIG. 6D presents a front perspective view of a 45° tilt angle, FIG. 6E illustrates a front perspective view of a 15° tilt angle, and FIG. 6F depicts a top view of the swivel range of the mounting stand 131.

Figure 7:
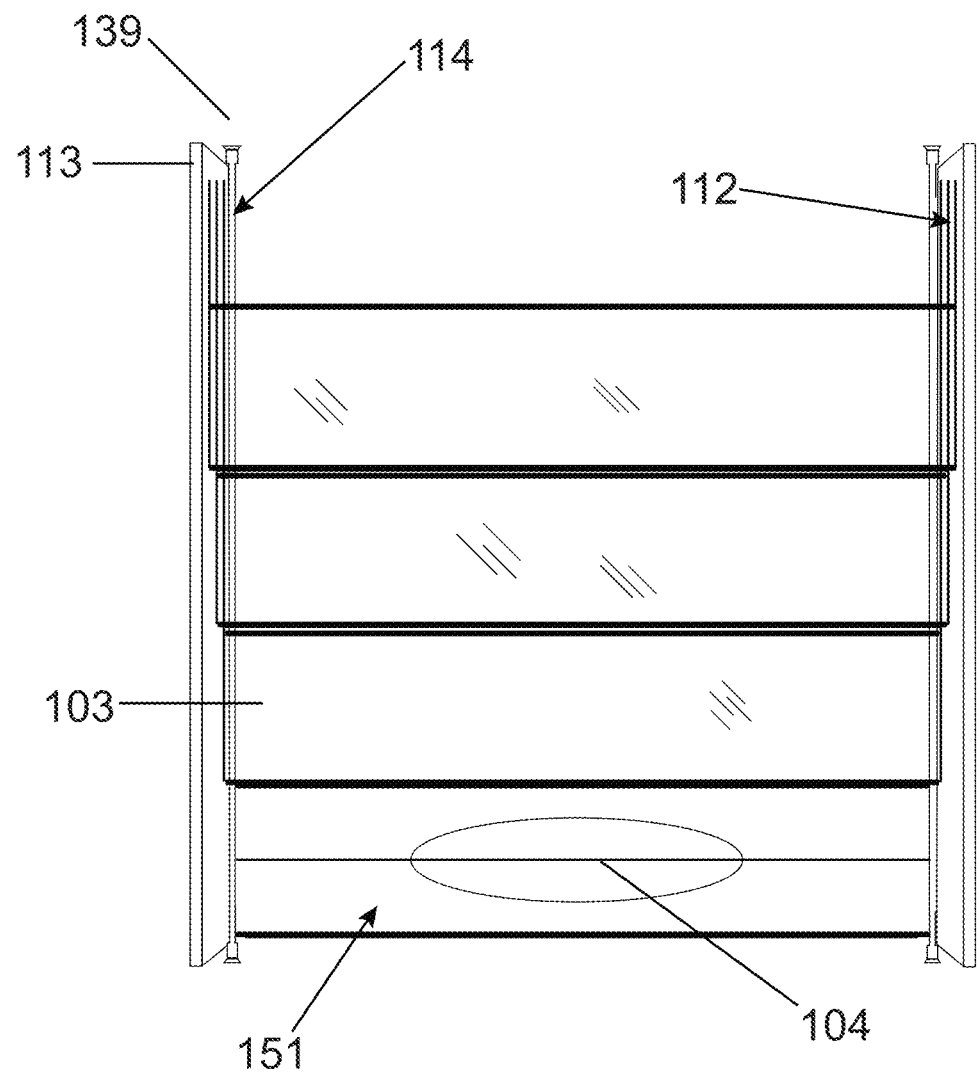
FIG. 7 depicts a front closeup view of the access panel assembly.

Now referring to FIG. 7, a front closeup view of the access panel assembly 139 (herein also referred to as "AP assembly") is depicted. The AP assembly 139 comprises the access panel group (herein also referred to as "access panels") 103 adjacent to the access panel frame 113 (herein also referred to as "AP frame"), panel rails 112, and support bridge 114 positioned parallel and oppositely disposed to form a left and right side of the AP assembly 139.

Figure 8A:
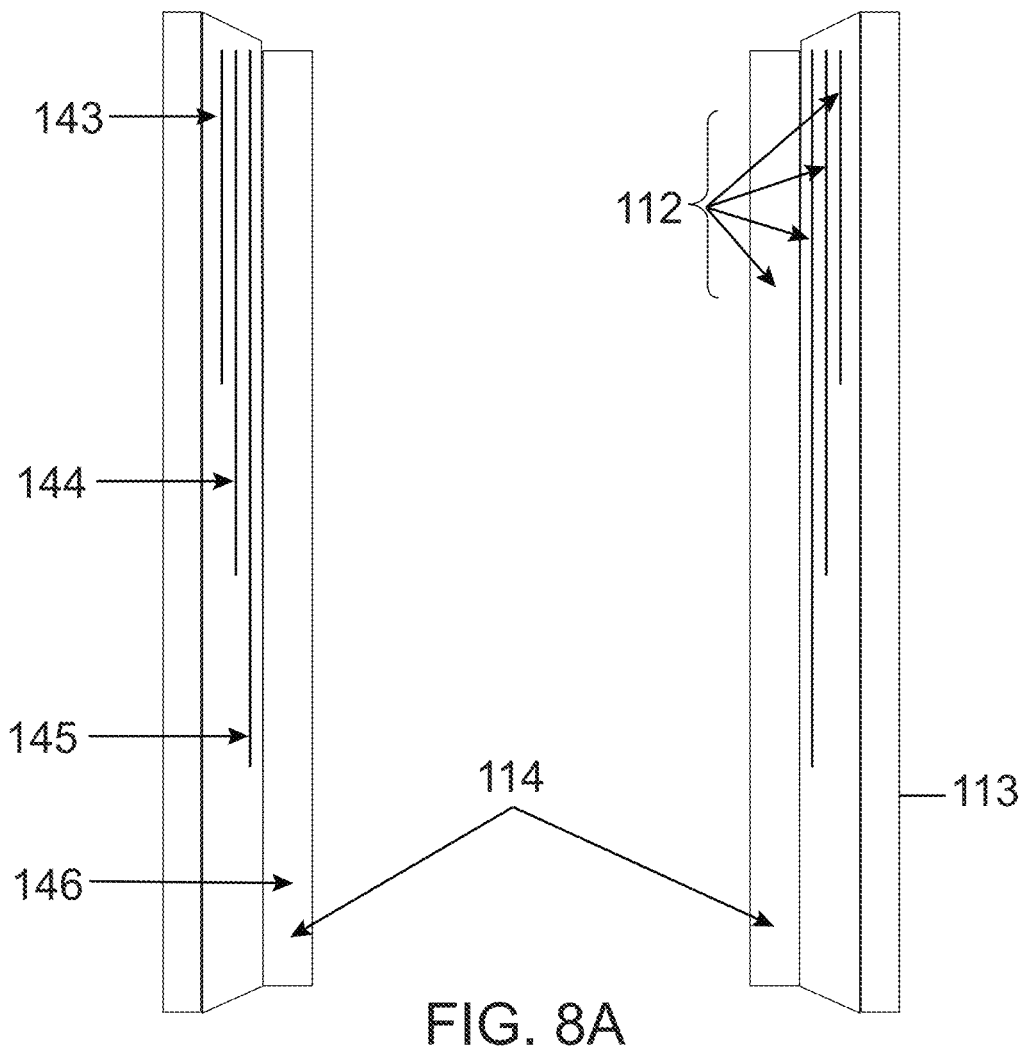
FIG. 8A represents a top view of an access panel frame with embedded rails.
Figure 8B:
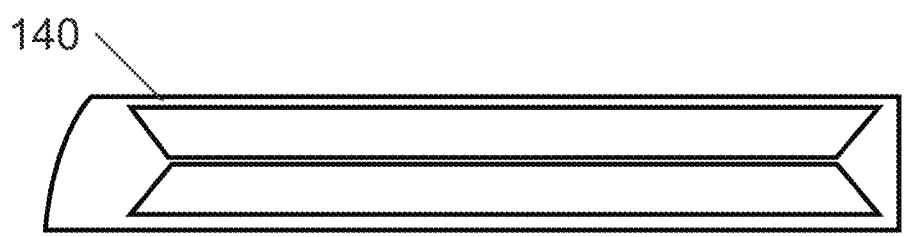
FIG. 8B exhibits a side closeup view of the nylon glide within a panel rail.

FIG. 8A shows a top view of the parallel and oppositely disposed access panel frame 113, panel rails 112, and support bridge 114 on the left and right side. Referring to the access panel frame 113, there are 3 embedded panel rails 112 exhibited, each lined with a nylon glide 140 as illustrated in FIG. 8B to improve the sliding action and reduce friction during movement of the access panels 103. The 4th rail in this four-panel embodiment is the opening created between the base of the access panel frame 113 identified as the support bridge 114 and the bottom edge of the 3rd embedded panel rail.

In addition to the panel rails 112 being identified as a component group, each individual panel rail is identified in FIG. 8A individually ranging from rail #1-4 in this four-panel embodiment. Reviewing the left side of the illustration from the top rail to the bottom (illustrated as left to right), rail #1 143 in this four-panel configuration travels from its panel bay 111 position to shield the first 25% of the chamber 100 opening. Rail #2 144 shields the 25-50% portion of the chamber 100 opening. Rail #3 145 shields the 50-75% portion of the opening. Rail #4 145 (herein also referred to as the "drive rail") is the opening created between the base of the access panel frame 113 identified as the support bridge 114 and the bottom edge of panel rail #3 145 and shields the 75-100% (bottom) of the chamber 100 opening to finalize the closure and sealing of the chamber 100.

FIGS. 9A and 9B show a top and side view respectively of the drive clip 141. A drive clip 141 attaches to (or optionally is molded within) the outer right and left portion of the drive panel 151 and its circular forks attach to the drive chain 147 which moves the drive panel 151 in each direction. The flat base of the drive clip 141 travels on the protruding edge of the AP frame 113 referred to herein as the support bridge 114, abutting against the panel support arms 142 during retraction to insure each of the panels 103 maintain synchronization and stability.

FIGS. 9C and 9D present an elevated side view and side closeup view respectively of the support arm 142 which attaches to (or optionally molded within) the outer left and right sides of each individual access panel within the AP group 103. The base of the support arm 142 moves laterally along the support bridge 114 to stabilize and maintain synchronization of the access panels 103. During retraction, the support arms 142 are pushed by the drive clip as they are moved, stacked, and parked in the panel bay 111.

Figure 10A:
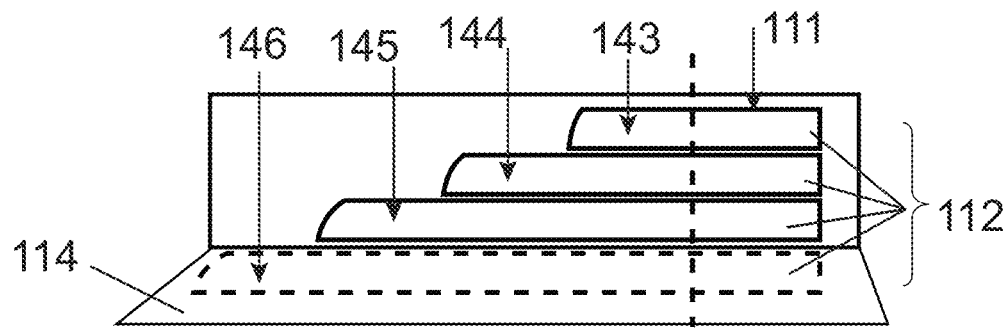
FIG. 10A depicts a side sectional view of the left access panel frame, panel rails, and drive rail.
Figure 10B:
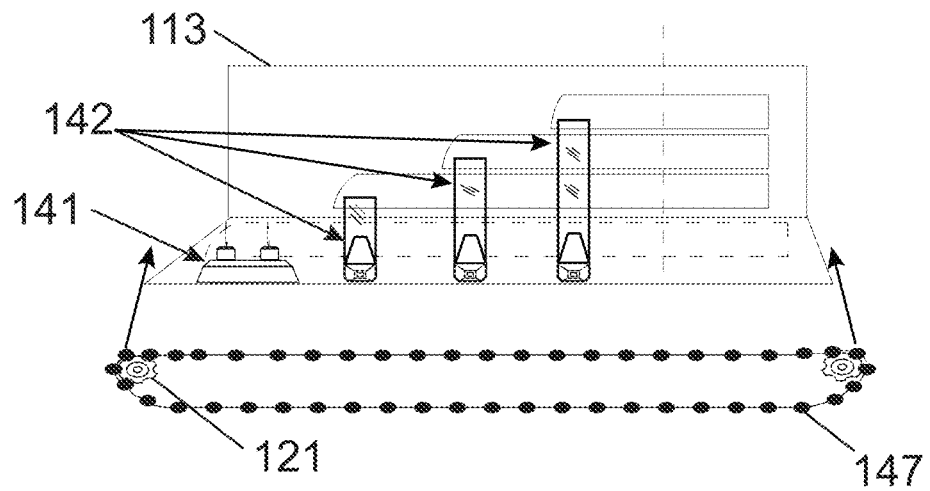
FIG. 10B shows the side sectional view depicted in 8A adding the drive clip, support arms, and an exploded view of the pulley and chain.
Figure 10C:
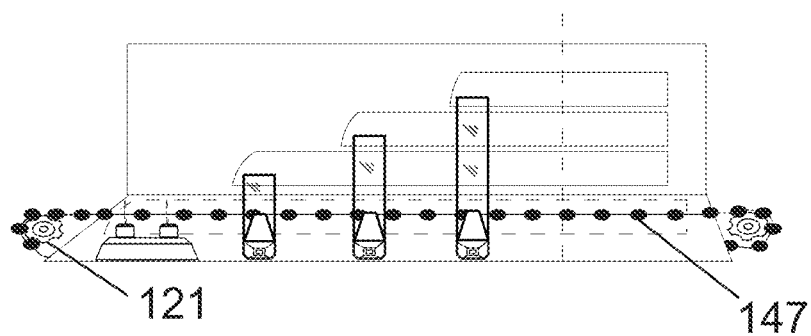
FIG. 10C portrays the side sectional view shown in 8B amended to show the pulley and chain in its operational position.
Figure 11:
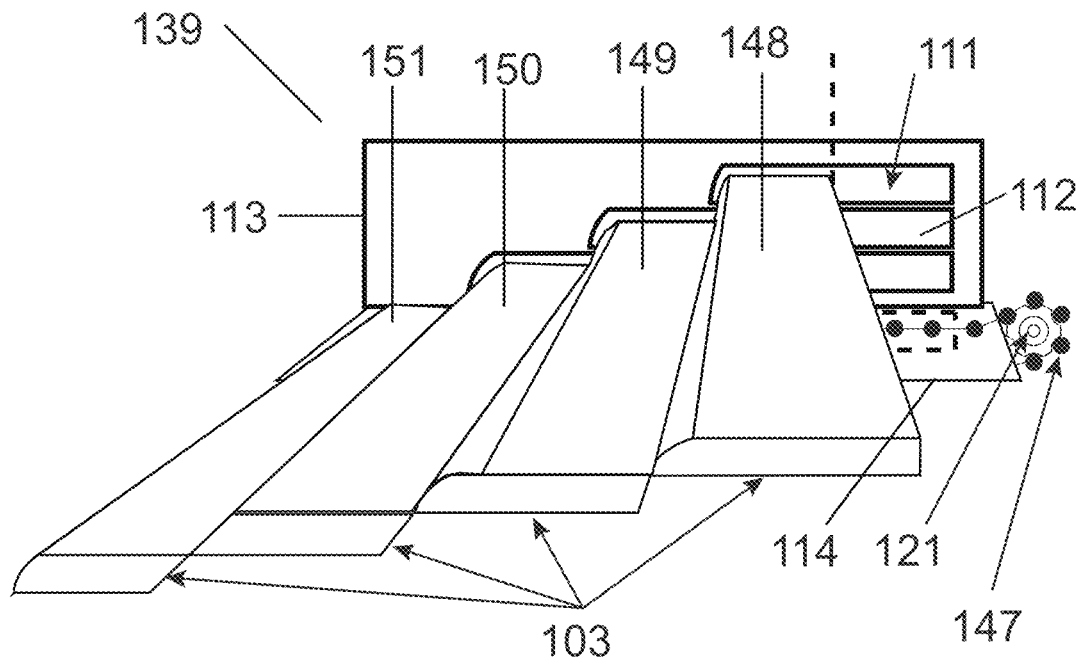
FIG. 11 represents a side sectional view of the access panels connected to their respective rails in the closed position and identifies the location of the panel bay when the access panels are retracted.

FIGS. 10A-10C exhibit a side sectional view of the left side access panel frame 113, panel rails 112, and support bridge 114 (supported by a depiction of the attached panels 103 in FIG. 11). FIG. 10A, as also referenced in the top view from FIG. 8A, identifies rail #1 143 as the top rail and serves as the side support for access panel #1 148 (FIG. 11) which is responsible for sealing the top 25% of the chamber 100 when the panels 103 are fully closed. Rail #2 144 is adjacent to access panel #2 149 (FIG. 11) and seals from 25-50%, rail #3 145 is adjacent to access panel #3 150 (FIG. 11) and seals from 50-75%, and rail #4 146 (the drive rail) is adjacent to access panel #4 151 (herein also referred to as the "drive panel") (FIG. 11) seals from 75-100% of the chamber 100 opening. FIG. 10B extends the detail from 10A by adding a transparent view of the support arms 142 and drive clip 141 extending from their respective panel to the support bridge 114. Additionally, FIG. 10B shows an exploded projection of the pulley 121 and drive chain position 147 relative to the access panel frame 113. FIG. 10C finalizes this view by placing the pulley 121 and drive chain 147 into position for this embodiment. This view is mirrored on the right side of the chamber.

FIG. 11 depicts a side sectional closeup view of the access panel assembly 139 comprising the AP frame 113, support bridge 114, rails 112, and access panels 103 with the access panels 103 in the closed position and each panel connected to their individually dedicated panel rails 112 (previously revealed in FIG. 10A). Viewing the illustration of FIG. 11 from right to left, panel #1 148 is sealing the top 25% of the front of the chamber 100 followed by panel #2 149, panel #3 150, and panel #4 151 (herein also referred to as "drive panel") which seal the remainder of the chamber 100 in 25% increments in this four-panel embodiment. When retracted, the panels 103 are stacked upon each other and "parked" in the panel bay 111 to reduce the footprint of the chamber 100 outside of the fomite 115 coverage area as clearly illustrated in FIG. 12E. In this embodiment, the pulley 121 is located at each end of the AP frame 113 and the drive chain 147 is looped around the top and bottom of the support bridge 114.

Figures 12A, 12B:
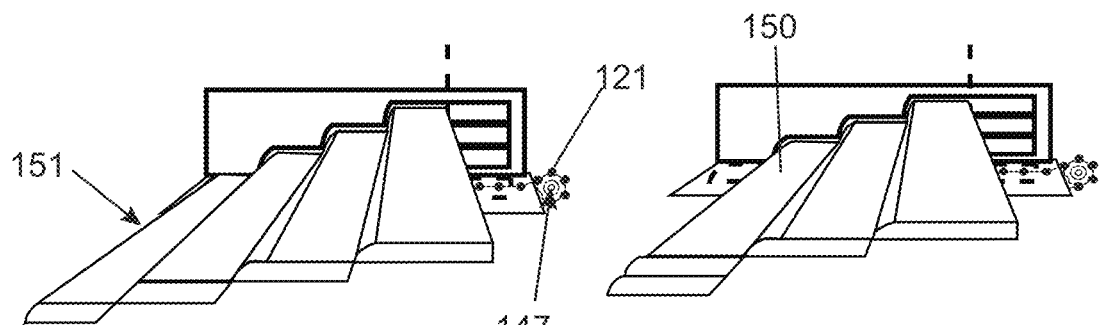
FIG. 12A exhibits a side sectional view of the access panel group in the closed position.
FIG. 12B exhibits a side sectional view of the access panel group 25% retracted.
Figures 12C, 12D:
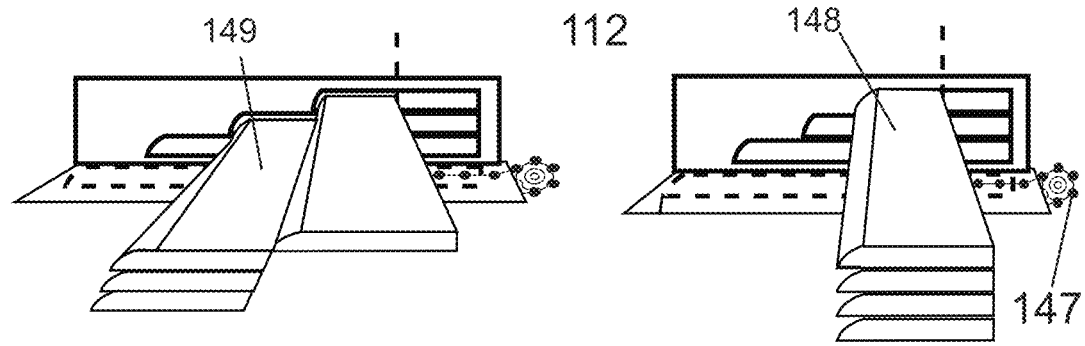
FIG. 12C exhibits a side sectional view of the access panel group 50% retracted.
FIG. 12D exhibits a side sectional view of the access panel group 75% retracted.
Figure 12E:
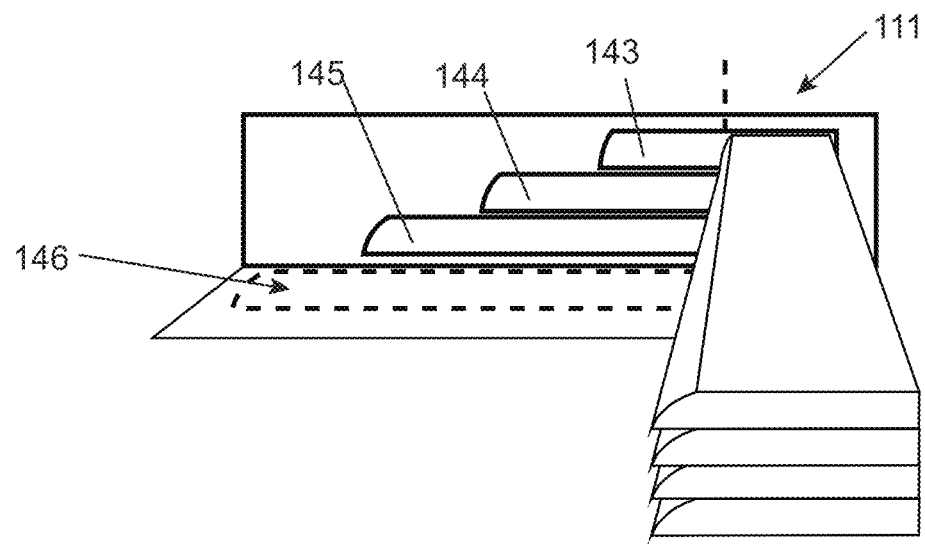
FIG. 12E exhibits a side sectional view of the access panel group fully retracted and parked in the panel bay.

Now referring to the operation of the AP assembly 139 in more detail, FIGS. 12A-E reveals side sectional closeup views of the 5-stages of panel retraction in a four-panel embodiment. FIG. 12A depicts the access panels 103 in the closed position. Panel #4 151 (the drive panel) is positioned at the bottom of the access panels 103 and as it is retracted, it begins to push access panel #3 150 as depicted in FIG. 12B. As panel #3 150 continues to be retracted by the drive panel 151, it captures panel #2 149 as presented in FIG. 12C. The drive panel 151, access panel #3 150, and access panel #2 149 continue to retract in synchronization as they interface with panel #1 148, shown in FIG. 12D where all access panels 103 are stacked upon each other. The chain 147 illustrated in FIG. 12D continues to retract the drive panel 151, causing panel #2 149 to capture panel #1 148 until they are all seated within their respective rail 143, 144, 145, 146 in the panel bay 111 (the panel bay area is demarcated by the broken vertical line in FIGS. 12A-E) as shown in FIG. 12E.

Figure 13:
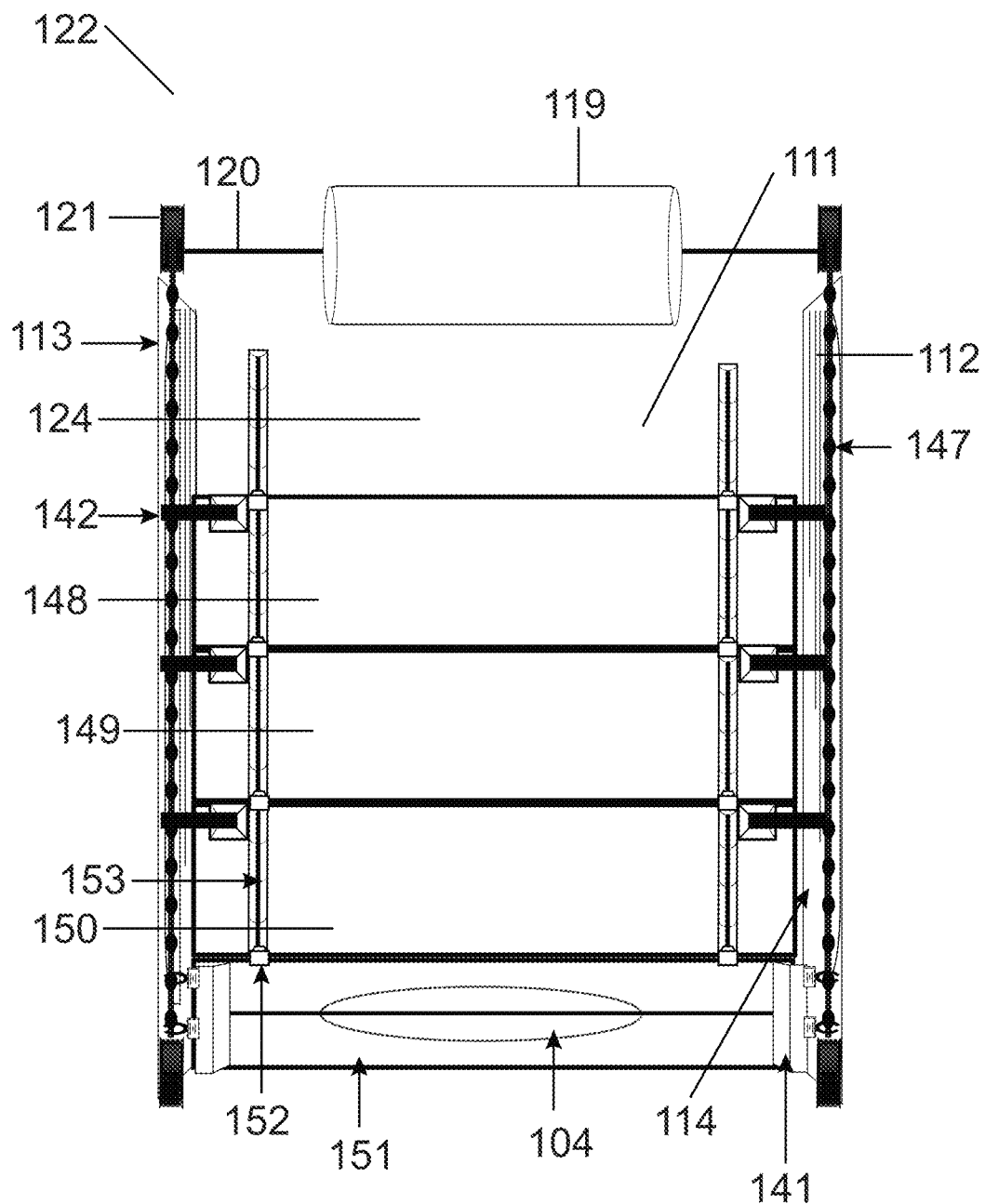
FIG. 13 shows a rear closeup view of the drive assembly.

FIG. 13 presents a rear closeup view of the drive assembly 122 comprising the drive motor 119, drive shaft 120, pulley 121, chain 147, access panel frame 113, rails 112, support bridge 114, access panels 103 comprising AP #1-4 148, 149, 150, 151 (referred to individually in this depiction), support arms 142, drive panel 151, drive clip 141, channel guide 153, guide clip 152, panel bay 111, and UV-reflective coating 124. Upon actuation of the drive motor 119, the drive shaft 120 and pulley 121 begin to move the chain 147 and attached drive clip 141 which in turn begins movement of the drive panel 151. Two oppositely disposed guide clips 152 are attached (or embedded into) to the horizontal leading edge of the drive panel 151 and each subsequent access panel 103 with the protruding front edge of the guide clips 152 fitted into the adjacent channel guide 153. During retraction, the two guide clips 152 on the drive panel 151 move vertically within the channel guides 153 of access panel #3 150 and begin to push it toward access panel #2 149. The guide clip 152 on access panel #3 150 and each subsequent access panel travel within their adjacent channel guide 153 to push the adjacent panel in the appropriate direction until the access panels 103 are parked within the panel bay 111. The access panels 103 are stabilized and synchronized during movement by the support arms 142 and base of the drive clip 141 which slide along and are buttressed by the support bridge 114. In alternative embodiments, the drive assembly 122 could be comprised of any mechanism capable of raising and lowering the access panels including but not limited to belts, springs, magnets, and hydraulic, pneumatic, or electrical linear actuators.

Figure 14:
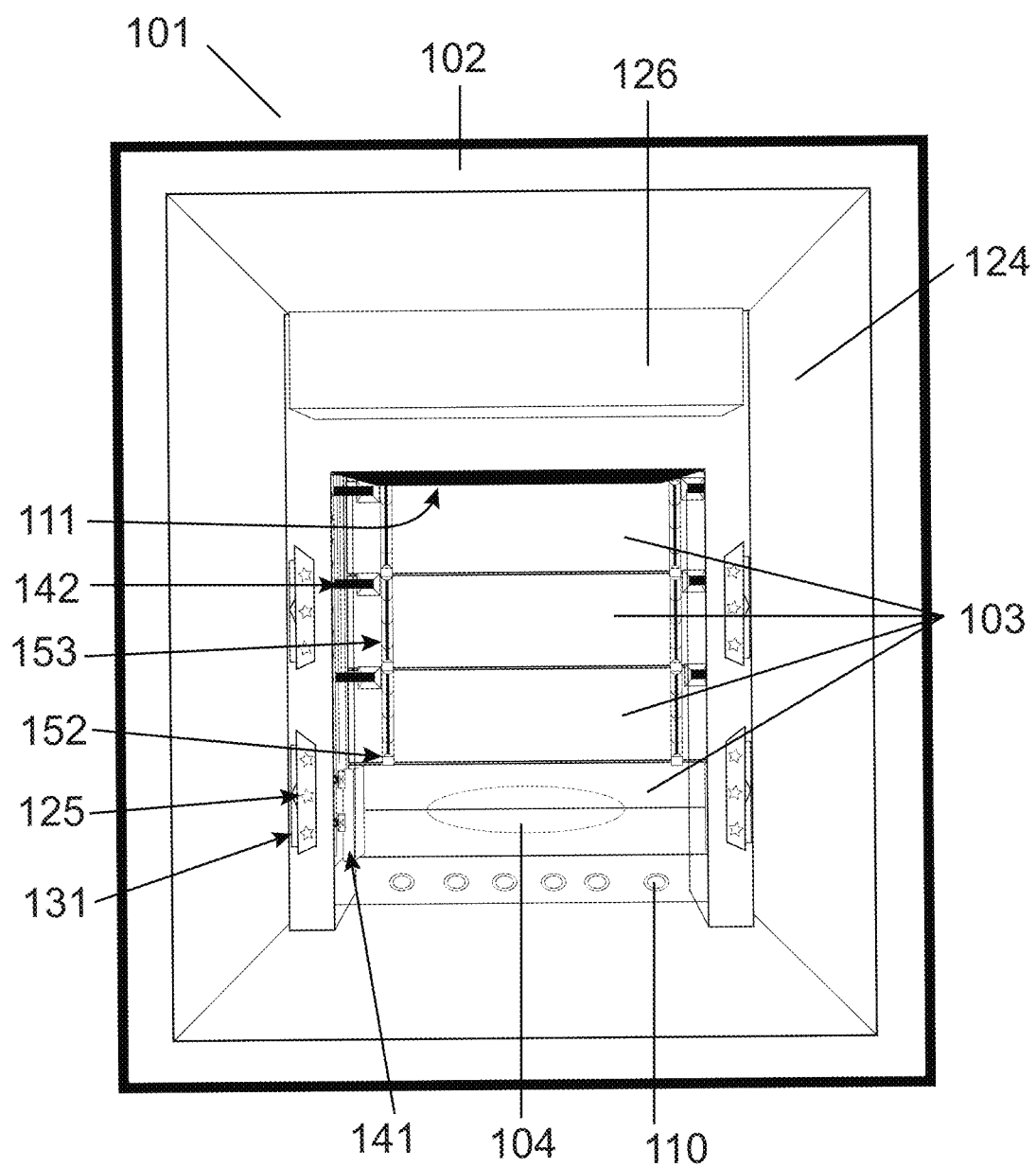
FIG. 14 represents a rear closeup view of the upper housing assembly.

FIG. 14 reveals a rear closeup view of the interior of the upper housing assembly 101. Illustrated components in this view comprise the chassis 102, battery 126, panel bay 111, UV-C 125, UV-C mounting stand 131, support arm(s) 142, channel guide 153, guide clip 152, drive clip 141, emergency handle 104, obstruction sensors 110, access panels 103, and UV-reflective surface 124 (not visible).

Figure 15A:
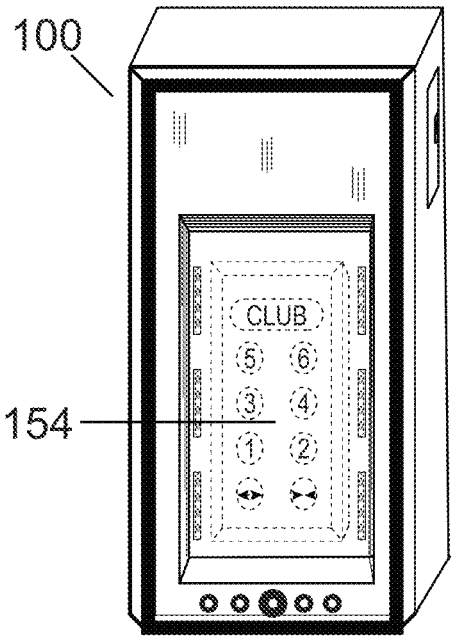
FIG. 15A reveals a front interior view of an open germ decontamination chamber adjacent to an elevator control panel.
Figure 15B:
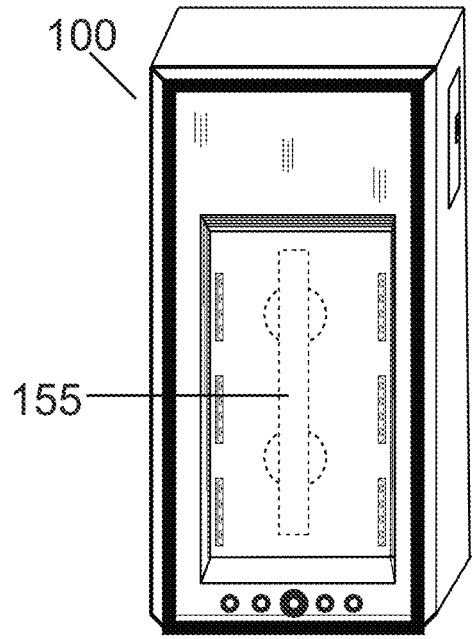
FIG. 15B displays a front interior view of an open germ decontamination chamber adjacent to a door handle.
Figure 15C:
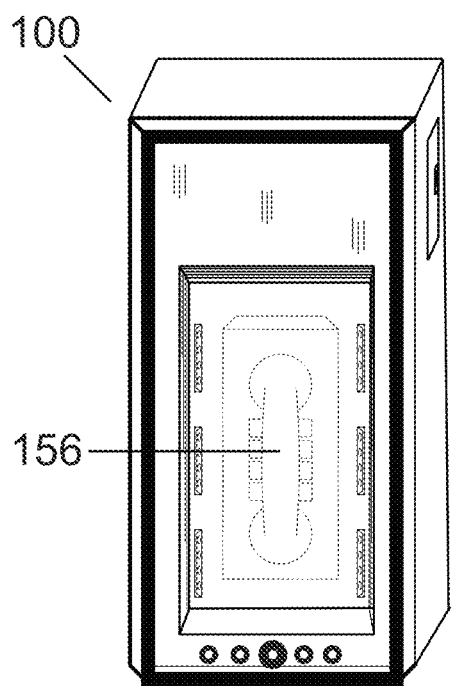
FIG. 15C presents a front interior view of an open germ decontamination chamber adjacent to a wall-mounted courtesy telephone.
Figure 15D:
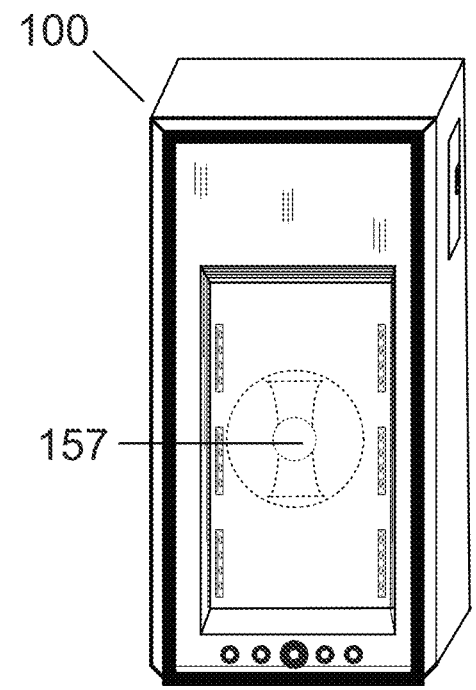
FIG. 15D illustrates a front interior view of an open germ decontamination chamber adjacent to a restroom stall deadbolt.

FIGS. 15A-D represent a front perspective view of a germ decontamination chamber 100 with the access panels 103 retracted revealing examples showing the positioning of different fomites 115 within the chamber. FIG. 15A depicts a germ decontamination chamber 100 adjacent to an elevator control panel 154. FIG. 15B exhibits a chamber 100 adjacent to an interior vertical bar-style door handle 155 such as those used in theaters and auditoriums. FIG. 15C shows a chamber 100 adjacent to a wall mounted courtesy telephone 156 such as those at airports and hotels. FIG. 15D presents a chamber 100 adjacent to a restroom stall deadbolt handle 157.

Figure 16:
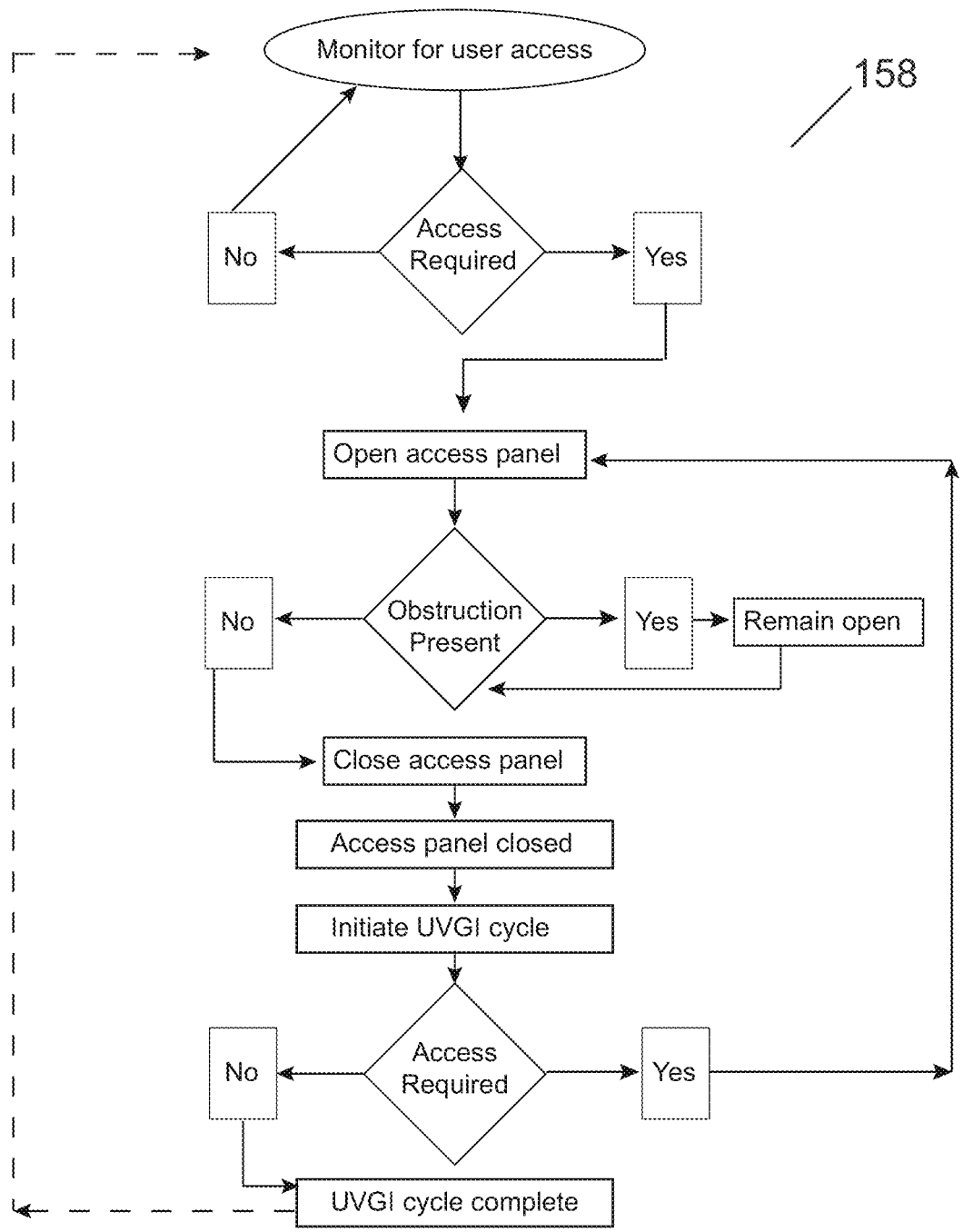
FIG. 16 depicts a process flow diagram for the germ decontamination chamber.

FIG. 16 reveals a flow diagram 158 illustrating one version of the operation of the germ decontamination chamber 100 for use with human touch point fomites 115. In standby mode, an access sensor 106 monitors for the presence of a user, the definition of which varies depending on the application. In certain embodiments, a user may be defined as any person within a defined distance of the chamber 100 i.e. six feet, while in certain other embodiments a user may be defined as someone who has placed their hand within a defined range of the sensor 106 i.e. six inches, while in yet even other embodiments, a user may be defined as someone within range of the chamber 100 possessing a mobile app, key fob, or other similar method or apparatus which is defined as an authorized user by the chamber 100. When a user has been detected, the access panels 103 are retracted and remain open either for a programmed period, until the sensor 106 no longer detects any obstructions, or a combination of both. When the closing criteria has been met, the access panels 103 begin to close and are only stopped in the event of an obstruction or newly defined user in which case the access panels 103 will begin to retract once again. After the device 100 is sealed, a UVGI cycle is initiated. If a user is detected while a cycle is in progress, the cycle stops and the access panels 103 are opened. Once the UVGI cycle is completed, the access panels 103 remain closed to prevent recontamination by airborne pathogens and the device 100 remains in a standby state until the presence of a user is detected.

FIGS. 17A-E reveal a front perspective view of a germ decontamination chamber 100 illustrating the 5-stages of panel retraction using an elevator control panel 154 (shown in FIG. 17E) as the fomite 115 example. FIG. 17A shows a closed and sealed chamber 100, FIG. 17B presents a chamber 100 with panel #4 151 (drive panel) retracted behind access panel #3 150, FIG. 17C portrays a chamber 100 50% open, FIG. 17D represents a chamber 100 75% open, and FIG. 17E presents an open chamber 100 revealing a sterilized and germ-free elevator control panel 154.

Referring now to an alternative embodiment, FIGS. 18A-20B illustrate a commercial door handle and lock germ decontamination chamber 200 (herein also referred to as "DHL chamber"). This embodiment is unchanged from the invention of FIG. 1A (the germ decontamination chamber) apart from the configuration of the baseplate 116 and baseplate cover 117; therefore, the present depiction is limited to the changes and the resulting embodiment of the invention.

As depicted in the front views of FIGS. 18A-D, the door handle and lock baseplate assembly 203 (herein also referred to as "DHL baseplate assembly") in this embodiment has form fitted cutouts to conform to the contours of the fomite 115, in this case the commercial door handle and lock 204. FIG. 18A depicts the left and right sides of the two-piece door handle and lock baseplate 201_L, 201-R (herein also referred to as "DHL baseplate") comprising the microcontroller 128, UV-C 125, and UV-C mounting stand 131 preparing to be fitted adjacent to the base of the handle & lock 203 using the male 129 and female 130 interlocking tabs. The resulting one-piece DHL baseplate 201 is shown in FIG. 18B. FIG. 18C shows the detached left and right sides of the fitted door handle and lock baseplate cover 202-L, 202-R (herein also referred to as "DHL baseplate cover") comprising a UV-reflective coating 124 and UV-C cutouts 127 preparing to be fitted over the DHL baseplate 201, and FIG. 18D presents the resulting DHL baseplate assembly 203 with UV-reflective coating 124 fitted adjacent to the door handle and lock 204.

FIG. 19A represents a distant front perspective view of a commercial door 205, handle, and lock 204 with the adjacent fitted DHL baseplate assembly 203 illustrated from FIG. 18D along with an exploded front view of the upper housing assembly 101 projected into position adjacent to the DHL baseplate assembly 203. FIG. 19B presents a front perspective view of the DHL germ decontamination chamber 200 mounted to the commercial door 205 with access panels 103 open revealing the adjacent door handle and lock 204.

Referring now to another embodiment, FIGS. 20A-21C illustrate a gas pump handle germ decontamination chamber (herein also referred to as "GP chamber"). This embodiment is unchanged from the embodiment of the invention of FIG. 1A (the germ decontamination chamber) apart from the configuration of the baseplate 116 and baseplate cover 117, therefore this depiction is limited to the changes and an illustration of the resulting embodiment of the invention.

As depicted in the front views of FIGS. 20A-D, the gas pump baseplate assembly 303 (herein also referred to as "GP baseplate assembly") in this embodiment has form fitted cutouts to conform to the contours of the fomite 115, in this case the gas pump handle 304 (herein also referred to as "GP handle" or "gas pump"). FIG. 20A depicts the left and right sides of the two-piece gas pump baseplate 301_L, 301-R (herein also referred to as "GP baseplate") comprising the microcontroller 128, UV-C 125, and UV-C mounting stand 131 preparing to be fitted adjacent to the base of the gas pump handle 304 and retractable hose well 305 using the male 129 and female 130 interlocking tabs. The resulting one-piece GP baseplate 301 is shown in FIG. 20B adjacent to the GP handle 304 and retractable hose well 305. FIG. 20C shows the detached left and right sides of the fitted gas pump baseplate cover 302-L, 302-R (herein also referred to as "GP baseplate cover") comprising a UV-reflective coating 124 and UV-C cutouts 127 preparing to be fitted over the GP baseplate 301, and FIG. 20D presents the resulting GP baseplate assembly 303 with UV-reflective coating 124 fitted adjacent to the GP handle 304 and retractable hose well 305.

FIG. 21A represents a distant front perspective view of a gas pump handle 304 and retractable hose well 305 with the adjacent fitted GP baseplate assembly 303 with UV-reflective coating 124 illustrated from FIG. 20D along with an exploded front view of the upper housing assembly 101 projected into position adjacent to the gas pump handle 304. FIG. 21B presents a front perspective view of the GP germ decontamination chamber 300 with panels 103 open revealing the adjacent gas pump handle 304 and retractable hose well 305. FIG. 21C presents an example of a gas pump handle germ decontamination chamber 300 in the closed position adjacent to a gas pump handle 304 within the context of a gas station service island 306.

Referring now to another embodiment of the invention, FIG. 22A-D presents a front closed, side perspective, front open, and top perspective view, respectively, of a single-panel germ decontamination chamber in the embodiment of a restroom stall latch germ decontamination chamber 400 (herein also referred to as "RS chamber"). As shown in FIG. 22A, the front of the RS chamber comprises a restroom stall drive panel 412 (access panel) (herein also referred to as "RS drive panel"), an emergency handle 104, access sensor 106, and four system status lights 105 to the left side of the access sensor 106 with the stall latch 406 protruding from the side.

As depicted in FIG. 22B, the elevated side perspective view shows the latch gateway 404 on the side of the RS chamber 400 along with an exploded view of the brush shield 405 being projected into position adjacent to the latch gateway 404. The brush shield 405 frames the latch gateway 404 and is comprised of multiple layers of dense yet flexible fiber to seal the latch gateway 404 while allowing the stall latch 406 (herein also referred to as "latch") to have freedom of lateral movement. The interior-facing fibers of the brush shield 405 are layered with a UV-reflective coating 124 to promote UV reflectivity while the outer-facing layers are dense enough to prevent light from escaping the interior of the RS chamber 400. In certain other embodiments, the brush shield 405 could be constructed with any material or substance that allows the latch 406 to be laterally moved while continuing to seal the latch gateway 404. In certain other embodiments, the RS chamber 400 might not include a brush shield 405.

FIG. 22C portrays a front view of the RS chamber 400 with the drive panel 412 retracted into the panel bay 111 to provide user access to the latch 406 and identifies the obstruction sensors 110 located in proximity to the bottom of the RS chamber 400. An elevated top perspective view of the RS chamber 400 is seen in FIG. 22D displaying the battery access door 107, battery release latch 108 (herein also referred to as "battery latch"), and battery lock 109 (herein also referred to as "security lock").

As depicted in the front views of FIGS. 23A-D, the restroom stall latch baseplate assembly 403 (herein also referred to as "RS baseplate assembly") has form fitted cutouts to conform to the contours of the fomite 115, in this case the restroom stall latch 406 (herein also referred to as "stall latch"). FIG. 23A depicts the left and right sides of the two-piece restroom stall latch baseplate 401 (herein also referred to as "RS baseplate") comprised of microcontroller 128, UV-C 125, and UV-C mounting stand 131 preparing to be fitted adjacent to the base of the stall latch 406 using the male 129 and female 130 interlocking tabs. The resulting one-piece RS baseplate 401 is shown in FIG. 23B. FIG. 23C presents the left and right sides of the two-piece restroom stall latch baseplate cover 402 (herein also referred to as "RS baseplate cover") comprising UV-C cutouts 127 and UV-reflective coating 124 projecting to be fitted over the RS baseplate 401 and adjacent to the stall latch 406, and FIG. 23D presents the resulting RS baseplate assembly 403 with UV-reflective coating 124 fitted to the stall latch 406.

Now referring to FIG. 24, a front closeup view of the restroom stall latch access panel assembly 413 (herein also referred to as "RS access panel assembly") is exhibited. The RS access panel assembly 413 comprises an access panel frame 113, support bridge 114, and RS drive panel 412 as contrasted with previous multi-panel embodiments which also include rails for the secondary panels. The functionality remains the same as in previous embodiments. The access sensor 106, status lights 105, obstruction sensors 110, and emergency handle 104 are also illustrated.

FIG. 25 shows a rear closeup view of the restroom stall latch drive assembly 410 (herein also referred to as "RS drive assembly") comprising the drive motor 119, drive shaft 120, pulley 121, drive chain 147, access panel frame 113, support bridge 114, drive clip 141, channel guide 153, guide clip 152, obstruction sensors 110, RS drive panel 412, and emergency handle 104. The functionality is the same as the invention of 1A.

FIG. 26 depicts an exploded rear perspective view of the restroom stall latch upper housing assembly 408 (herein also referred to as "RS UHA") comprising the restroom stall chassis 409 (herein also referred to as "RS chassis") comprising UV reflective coating 124, RS drive assembly 410 comprising UV-reflective coating 124, shroud 123 comprising UV-reflective coating, UV-C 125, and battery 126 comprising UV-reflective coating 124. The functionality remains congruent with the invention of FIG. 1A; however, the physical structure differs due to being a single panel embodiment which eliminates the additional panels, panel rails, and related supporting components.

FIG. 27 presents a rear view of an assembled RS UHA 408 with visible components comprising the RS chassis 409, shroud 123, battery 126, UV-C 125, UV reflective coating 124, RS drive panel 412, channel guides 153, guide clips 152, obstruction sensors 110, and emergency handle 104.

FIG. 28 reveals a front exploded front view of the RS baseplate 401, RS baseplate cover 402, and RS UHA 408 projected into position adjacent to a restroom stall latch 406.

FIG. 29 presents a front perspective view of a restroom stall door 411, stall latch 406, and stall latch receiver 407 with an adjacent RS chamber 400 with the RS drive panel 412 open to allow access to the latch 406.

Now referring to an additional embodiment of the invention, FIGS. 30A-36 present a free-standing point-of-sale (POS) terminal germ decontamination chamber 500 (herein also referred to as "POS chamber") for use at retail checkout counters 508 and the like.

FIGS. 30A-C portray a front closed view, front open view, and rear perspective view, respectively of a POS chamber adjacent to a POS mounting stand. The stand can be permanently affixed to a fixture such as a table or counter through fasteners or adhesives or alternatively can be unmounted and moved when necessary depending on the application and environment. In this embodiment, the front of the POS chamber comprises the chassis 502, access sensor 106, status lights 105, obstruction sensors 110, a POS stand 506, and a six-panel access panel group (herein also referred to as the "access panels") 524 to minimize the vertical footprint of the device as illustrated in FIG. 30A-B. The rear perspective view of FIG. 30C reveals the direct AC electrical power connection 509 for the POS chamber. Alternative embodiments could comprise a battery 126 power source for environments where an AC connection is unavailable. The POS chamber can be constructed of plastic, metal, or any other suitable material.

Now referring to FIGS. 31A-B, FIG. 31A reveals a front view of the POS baseplate 503 comprising the baseplate 503, microcontroller 128, embedded POS mounting plate surface 507, UV-C 125, and UV-C mounting stand 131. The depth of the POS baseplate 503 allows placement of the POS terminal 510 (FIG. 35G) and an upwardly sloped lower edge with UV-C 125 and UV-C mounting stand 131 mounted to its surface allowing the light to project to the face of the POS terminal 510 (FIG. 35G). In an alternative embodiment, the UV-C 125 can be placed directly on the surface of the baseplate 503 without the UV-C mounting stand 131. In another alternative embodiment, the UV-C 125 can be positioned on the rear of the access panels 524. FIG. 31B displays a front view of the POS baseplate cover 504 comprising UV-C cutouts 127, UV-reflective surface 124, and a POS stand mounting plate 508.

FIG. 32A depicts a front exploded view of the POS baseplate cover 504 comprising UV-C cutouts 127 and mounting stand plate 508 being projected into position on top of and adjacent to the POS baseplate 503 comprising microcontroller 128, UV-C 125, and embedded POS mounting plate surface 507. As illustrated in FIG. 32B, the combined POS baseplate 503 and POS baseplate cover 504 form the POS baseplate assembly 505. The POS mounting stand plate 508 attaches to the POS stand 506 as revealed in FIG. 32B. In an alternative embodiment, the POS baseplate assembly 505 can function as a stand-alone assembly without the use of a POS stand 506 or external mounting apparatus.

FIG. 33A reveals a front view of the POS access panel assembly 515 (herein also referred to as "POS AP assembly") comprising parallel and oppositely disposed access panel frames 113 (herein also referred to as "AP frame(s)"), POS panel rails 512 (herein also referred to as "POS rails"), and support bridges 114 to form a left and right side of the POS AP assembly 515 and framing the POS access panel group 514 (herein also referred to as "POS access panels" or "access panels") which comprises all access panels including the individually defined POS drive panel 513. The POS AP assembly 515 comprises relatively equivalent components and shares the same functional operation as the invention of FIG. 1A and the description provided for the access panel assembly 139 illustrated in FIG. 7 apart from the number of access panels 514 (six versus four) and the number of rails 515 to support the access panels 514 (five versus three).

FIG. 33B shows a rear closeup view of the POS drive assembly 516 comprising the drive motor 119, drive shaft 120, pulley 121, chain 147, access panel frame 113, POS rails 512, support bridge 114, POS access panels 514, support arms 142, POS drive panel 513, drive clip 141, channel guide 153, guide clip 152, panel bay 111, emergency handle 104, and UV-reflective coating 124.

Still referring to the POS drive assembly 516 presented in FIG. 33B, upon actuation of the drive motor 119, the drive shaft 120 and pulley 121 begin to move the chain 147 and attached drive clip 141 which in turn begins movement of the POS drive panel 513. Two oppositely disposed guide clips 152 are attached (or embedded into) to the horizontal leading edge of the POS drive panel 513 and each subsequent POS access panel 514 with the protruding front edge of the guide clips 152 fitted into the adjacent channel guide 153. During retraction, the two guide clips 152 on the drive panel 513 move vertically within the channel guides 153 of the adjacent POS access panel 514 and begin to push it toward the next adjacent POS access panel 514. The guide clip 152 on each POS access panel 514 travel within their adjacent channel guide 153 to push the adjacent access panel 514 in the appropriate direction until the POS access panels 514 are parked within the panel bay 111. The POS access panels 514 are stabilized and synchronized during movement by the support arms 142 and base of the drive clips 141 which slide along and are buttressed by the support bridge 114. The POS drive assembly 516 illustrated in FIG. 33B comprises relatively equivalent components and shares the same functional operation as the invention of FIG. 1A and detailed description of FIG. 13 aside from the number of access panels 514, rails 512, and their supporting components.

FIG. 33C displays a rear closeup view of the POS upper housing assembly 501 (herein also referred to as "POS UHA") including the adjacent POS terminal 510 as indicated by the rectangular broken lines. Illustrated components in this view comprise the POS chassis 502, optional battery 126, panel bay 111, UV-C 125, UV-C mounting stand 131, support arm(s) 142, channel guide 153, guide clip 152, drive clip 141, emergency handle 104, obstruction sensors 110, POS access panels 514 (including the drive panel 513), and UV-reflective surface 124 (not visible). The POS UHA 501 illustrated in FIG. 33C comprises relatively equivalent components and shares the same functional operation as the invention of FIG. 1A and detailed description of FIG. 14 aside from the number of access panels 514, rails 512, and their supporting components.

FIG. 34A illustrates a front exploded view of the POS UHA 501 being projected into position on top of and adjacent to the POS baseplate assembly 505 with the resulting front perspective view of the POS chamber 500 being presented in FIG. 34B.

FIGS. 35A-G present a front view of the seven access panel positions of the POS chamber 500 beginning with being closed and sealed in FIG. 35A and concluding with the POS terminal 510 being fully accessible in FIG. 35G.

FIG. 36 reveals a front perspective example of the POS chamber 500 adjacent to a retail checkout counter 511.

Now referring to an additional embodiment of the invention, FIGS. 37A-47E show a cylindrical germ eradication chamber 600. In the preferred embodiment, the cylindrical chamber 600 is used to decontaminate germs from elongated and horizontally displaced fomites 115 i.e., push-style door handles (ex: panic bars, crash bars, horizontal push bars), shopping cart handles and the like. In alternative embodiments, the cylindrical germ decontamination chamber 600 could be vertically or diagonally oriented on fomites 115 better served by a cylindrical chamber 600 than a linear chamber.

Referring now to the invention illustrated in FIGS. 37A-47E, a cylindrical germ decontamination chamber for shopping cart handles 600 (herein also referred to as "SC chamber") is presented. FIG. 37A provides a front view example of the SC chamber 600 adjacent to a shopping cart 609. FIG. 37B shows a front view of the SC chamber 600 detached from the shopping cart 609 with front facing components comprising the cylindrical access panel group 604 (herein also referred to as "cyl panels" or "access panels"), left housing 605, right housing 606, access sensor 106, status lights 105, and the undercarriage assembly 603.

FIGS. 38A-B show a front view and an elevated front perspective view, respectively, of the cylindrical baseplate 601 (herein also referred to as "cyl baseplate") of the SC chamber 600. As illustrated in FIG. 38B, the cyl baseplate 601 comprises UVC 125 positioned in proximity to the upper rear of the slope to deliver UVGI directly toward the shopping cart handle 610 (FIG. 40A). In the preferred embodiment, the UV-C 125 is embedded or affixed to UV adhesive strips 611 which are pre-wired to deliver power to the UV-C 125. Alternative embodiments include but are not limited to the UVC 125 could be embedded directly into the surface during the manufacturing process, adhered to the surface directly, mounted to the cyl baseplate 601 with the UV-C mounting stand 131, or through any other suitable method. In another alternative embodiment, the UV-C 125 could be affixed directly to one or more of the cyl panels 604.

FIG. 39A depicts a top perspective view of the cylindrical baseplate cover 602 (herein also referred to as "cyl baseplate cover") comprising a UV-reflective surface 124 comprised of UV-reflective paint, TPFE, aluminum foil, or any other substance/material proven to optimize ultraviolet reflectivity. The cyl baseplate cover 602 also comprises UV-C cutouts 612 which overlay the UV-C 125 from the cyl baseplate 601 to allow the light to be delivered to the shopping cart handle 610 (FIG. 40A) while preventing tampering by users.

FIG. 39B displays an elevated front perspective exploded view of the cyl baseplate cover 602 projected and seated upon the cyl baseplate 601 to form the undercarriage assembly 603 of the SC chamber 600. The cyl baseplate 601 and cyl baseplate cover 602 can be manufactured of metal, plastic, or any other suitable material.

The shopping cart handle 610 is flanked on each side by parallel containers identified as the left housing 605 and the right housing 606 as shown in the exploded front view of FIG. 40A. The left housing 605 (herein also referred to as the "drive housing") contains the functional power, electrical, and motorized components of the SC chamber 600 including the access sensor 106 and status lights 105. The right housing 606 (herein also referred to as the "driven housing") functions as a receiver for the right side of the cyl access panels 604 (FIG. 44B). Still referring to FIG. 40A, an exploded view illustrates the undercarriage assembly 603 being projected toward its position on the chamber 600 centered between and adjacent to the left 605 and right housings 606 and underneath the shopping cart handle 610.

FIG. 40B shows a side view of the left housing 605 comprising the battery access door 107, battery latch 108, and security lock 109. Both the left 605 and right housing 606 can be constructed of metal, plastic, or any other suitable material which can provide the necessary strength, rigidity, and durability to optimize the performance of the chamber 600.

FIG. 41A illustrates a side perspective exploded view of the components of the left housing 605 comprising the left housing chassis 607, microcontroller 128, battery 126, cylindrical drive motor 613 (herein also referred to as "cyl motor" or "motor"), drive shaft 615, motor support 614, drive hub 616 (herein also referred to as "hub"), driven drum 617 (herein also referred to as "drum"), and the end cap 618. The hub 616 connects directly to the cyl motor 613 and drive shaft 615 as depicted in FIG. 41A, rotating clockwise to retract the cyl access panels 604 in a stacked array providing access to the shopping cart handle 610 and counterclockwise to close and seal the chamber 600. The drum 617, by contrast, functions as a stationary component and as such does not rotate.

The open elliptical center of the end cap 618 is placed around the edges of the drum 617, securing it in place, and then attached to the left chassis 607 to seal the left housing 605. An assembled view of the left housing 605 in hub position "0" (closed) 635 is depicted in FIG. 41B.

FIG. 42A exhibits a front closeup exploded view of the left hub 616 projected into its position within the center of the left drum 617. The two integrated components form the left hub & drum assembly 621 (herein also referred to as "left H&D assembly") as illustrated in FIG. 42B. The cyl rails 630 which support the cyl panels 604 are also depicted in FIG. 42B. Additional detail regarding the interface between the hub 616, drum 617, and cyl access panels 604 is provided in FIGS. 44A-48E.

In more detail, still referring to the invention of FIG. 37A, a side perspective exploded view of the right housing 606 is depicted in FIG. 43A comprising the right chassis 608, free spinning hub 619, drive shaft 615, free spinning hub support 620, right H&D assembly 622, and end cap 618. The right housing 606 is a "driven housing" as previously mentioned; subordinated to the left housing 605 in that it has no power or control functions within the SC chamber 600. The right chassis 608 is additionally distinguished from the left chassis 607 by having less internal area due to the absence of a microcontroller 128 and battery 126 from the chassis 608 as previously depicted in FIG. 40A. Alternative embodiments could include, but are not limited to, a motorized H&D assembly in both the left and right housing 621, 622 through a single or plurality of cyl drive motors 613 and powered by a single or plurality of batteries 126.

Still referring to FIG. 43A in more detail, the right housing 606 comprises a free spinning hub 619 and a connected drive shaft 615 which is actuated through the movement of the components within the opposing left housing 605. The drum 617 overlays the free spinning hub 619 within the right chassis 608 and is secured in a stationary position when the end cap 618 is inserted into the chassis 608 to close the right housing assembly 606.

FIG. 43B represents a side perspective view of the left chassis 607 (illustrated with the side removed) and the left H&D assembly 621 (other internal components removed for visibility) connected to cyl panel #1 631 (herein also referred to as "the drive panel") which is connected to the right housing 606 in the closed position.

FIG. 44A presents a side closeup view of the left H&D assembly 621 in hub position "0" 635 (closed). The left hub 616, when viewed from the right side (inside) of the left chassis 608, rotates in a clockwise direction to retract the cyl access panels 604 upon each other in a stacking form as indicated by the directional arrows within the left H&D assembly 621 in FIG. 44A. In hub position "zero" 635 (closed position) cyl panel #1 631 (the drive panel as exhibited in FIG. 47A) is affixed to cyl rail #1 626 (herein also referred to as the "drive rail") in the 8-10 o'clock slot on the hub 616 as indicated in FIG. 44A. Each embedded rail within the drum 617 comprises an embedded nylon glide 140, illustrated in FIG. 44B, to promote freedom of movement and prevent friction during cyl panel 604 movement. Alternative embodiments include, but are not limited to, the cyl rails 630 comprising ball bearings or similar fittings, surface coatings, materials, or any other suitable solution that promotes freedom of movement and reduces friction for the cyl panels 604. In another alternative embodiment, the cyl panels 604 could be constructed of any material that promotes freedom of movement and reduces friction between the cyl rails 630 without the use of additional components.

FIGS. 45A-B show a top and bottom perspective view, respectively, of the cylindrical access panels 604 using cyl panel #1 631 in FIGS. 45A-45B and the left illustration in 45C. The bottom view of FIG. 45B reveals the cylindrical drive clips 623 (herein also referred to as "cyl drive clips" or "drive clips") and a UV-reflective coating 124 such as aluminum foil, UV-reflective paint, TPFE, or any other substance/material that optimizes reflectivity of UV-C light within the SC chamber 600. All interior areas within the undercarriage assembly 603 and access panels 604 of the SC chamber 600 are coated with a UV-reflective material/substance 124 as are all fomite-facing components within the various embodiments of this invention. FIG. 45C exhibits a bottom exploded view of a three-access panel 604 example of their interface with projection arrows indicating the placement of each access panel 604 within the array. Describing FIG. 45C in more detail as shown from left to right, the left panel is an example of cyl panel #1 631 (the drive panel) depicting a panel with cyl drive clips 623 but absent of channel guides 624. The cyl drive clips 623, as shown in the top and bottom of the illustration, are vertically oriented allowing them to fit within the recessed barrel of the channel guides 624 in adjacent cyl panel #3 633 (center) as illustrated by the arrows. The channel guides 624 have a solid edge at each end which causes the panel to be pushed or pulled, depending on the direction of the panel movement, by the cyl drive clips 623 attached to the adjacent panel. Cyl panel #3 633 (center) is comprised of channel guides 624 and cyl drive clips 623. The cyl drive clips 623 from the center panel are fitted within the parallel and oppositely disposed edges of the channel guides 624 on the panel on the right side of FIG. 45C referenced as cyl panel #4 634 (the exit panel). The right panel is characterized as an exit panel as evidenced by being comprised of channel guides 624 to allow it to be pushed and pulled during retraction and closing through the action of the preceding panel's cyl drive clips 623; however, it is not comprised of its own drive clips 623 since, as the final panel in the array, it is itself moved but does not otherwise move any other panels 604.

FIGS. 46A-E and FIGS. 47A-E further detail the operation of the cyl access panels 604 (previously illustrated in FIG. 37B) and their interface with the H&D assembly 621 (FIG. 47A). FIGS. 46A-E depict a side closeup view of the left H&D assembly 621 illustrating the five stages of panel retraction and FIGS. 47A-E exhibit a top perspective view of the corresponding cyl panels 604 (FIG. 47A) being retracted throughout the five-stage retraction process in the four-panel SC chamber 600 embodiment.

Referring to FIG. 46A, the hub 616 and drum 617 slots are in hub position "0" 635 (closed) within the left housing 605 (shown in FIG. 41B) which is mirrored within the opposite side right housing 606 (presented in FIG. 43B). Defining the cyl rails 630 by number, cyl rail #1 626 is the drive rail for which cyl panel #1 631, depicted in FIG. 47A, is affixed to the location on the drive hub 616 identified by the broken lines between 8-10 o'clock. Cyl rail #1 626 comprises a fixed width slot to which cyl panel #1 631 (drive panel shown in FIG. 47A) connects and rotates in synchronization with the hub 616. Continuing in a clockwise direction, the fixed-mount drum 617 comprises cyl rail #2 627, cyl rail #3 628, and cyl rail #4 629 as identified in FIG. 46A with the closed panel position for each respective rail indicated by broken lines. Each of the three rails on the drum 617 in this embodiment comprise an embedded rail with a nylon glide 149 (FIG. 44B) which continues throughout the rotation area terminating in the cyl panel bay 625 depicted in FIG. 46E. A corresponding view of the SC chamber 600 in this position with the cyl panels attached is shown in FIG. 47A.

FIG. 46B shows hub position #1 636 whereby the hub 616 and cyl rail #1 626 has rotated clockwise into a position underneath cyl rail #2 627 as indicated by the alignment of the broken lines. The corresponding position of the cyl panels 604 within the SC chamber 600 in this position is portrayed in FIG. 47B.

FIG. 46C represents hub position #2 637 whereby the hub 616 and cyl rail #1 626 has rotated into a position underneath cyl rail #3 628 and brought with it the cyl rail #2 627 creating three stacked panels as depicted by the alignment of the broken lines in FIG. 46C. The corresponding position of the cyl panels 604 within the SC chamber 600 in this position is portrayed in FIG. 47C.

FIG. 46D reveals hub position #3 638 whereby the hub 616 and cyl rail #1 626 has rotated into a position underneath cyl rail #4 629, moving the panels within cyl rail #2 627 and #3 628 with it thereby creating four stacked panels. The corresponding position of the cyl panels 604 within the SC chamber 600 in this position is represented in FIG. 47D illustrating the cyl panels 604 as being 75% open. Hub position #4 639 is the final stage in the panel retraction process as is presented in FIG. 46E. In this stage, the hub 616 and cyl rail #1 626 (drive rail) has rotated into the innermost position within the cyl panel bay 625 and brought with it the cyl panels 604 (FIG. 47E) attached to cyl rail #2 627, #3 628, and #4 629 so the cyl rail group 630 is aligned upon each other. The corresponding position of the cyl panels 604 within the SC chamber 600 in this position is represented in FIG. 47E revealing the cyl access panels 604 100% retracted and stacked upon each other within the cyl panel bay 625 as illustrated in FIG. 47E.

Referring to FIGS. 47A-E in more detail, these present a top perspective view of the five stages of panel retraction for the SC chamber 600. FIG. 47A illustrates a fully closed and sealed SC chamber 600 and identifies the individual cyl panels 604. Viewing FIG. 47A from left to right, cyl panel #1 631 serves as the drive panel which is connected to the hub 616 as illustrated in FIG. 46A; followed by cyl panel #2 632, cyl panel #3 633, and cyl panel #4 634 in order from left to right which are attached to their dedicated rail on the drum 617 as illustrated in FIG. 46A.

FIG. 47B shows cyl panel #1 631 retracted underneath cyl panel #2 632 which would reveal 25% of the shopping cart handle 610 (not shown). With cyl panel #1 631 drive now positioned beneath cyl panel #2 632, the continued rotation of cyl panel #1 631 pushes cyl panel #2 632 underneath cyl panel #3 633 to reveal 50% of the shopping cart handle 610 as depicted in FIG. 47C. Cyl panel #1 631 continues to rotate and push cyl panel #2 632 and cyl panel #3 633 to stack underneath cyl panel #4 634 revealing 75% of the shopping cart handle 610 as represented in FIG. 47D. In the final stage of retraction, as cyl panel #1 631 is pushing cyl panel #2 632, cyl panel #3 633, and cyl panel #4 634 into the cylindrical panel bay 625 where all four panels are stacked upon each other as revealed in FIG. 47E. To close the panels and seal the SC chamber 600 (as depicted in FIG. 37A), the process is repeated led by cyl panel #1.

As used herein, the term enclosure generally is as described above and can generally include or be a chamber or a chassis with one or more sides. An enclosure can be in a variety of geometric shapes and will generally completely enclose a fomite with the exceptions of a door or access panels and an opening to accommodate the fomite when the fomite is attached to something else. For example, a door handle connected to a door, or a gas pump handle connected to a gas pump, etc. In embodiments, an enclosure can be three dimensional rectangular in shape with six sides. In embodiments, the enclosure can be cube, rectangular prism, sphere, cone and/or cylindrical in shape but is not limited thereto. An enclosure may be airtight and/or watertight when the door or access panels are closed.

In embodiments, a sensor as used herein, may include an obstruction sensor, a motion sensor or detector, a light sensor, a sound sensor, and/or a heat or infrared sensor. As discussed above, in embodiments, a sensor can detect the presence of a user and then automatically trigger the opening of the door or access panels of the enclosure or chamber. Such a system allows a user to access the fomite without touching the door or access panel.

A trigger or a trigger event is an event or trigger which opens the access door and is generally detected by a sensor. That is, a user approaching a fomite may trigger a sensor causing the door or access panel of the enclosure to open allowing access to the fomite. Thus, a trigger event may be an event detectable by a sensor as described above. For example, in a restroom environment, a motion sensor or light sensor can be used to detect a trigger event and the presence of a user (as is routinely done at restroom stalls to trigger the flushing of the toilet, or turning on or off, of a water faucet). For a door handle, a trigger event could be a user approaching the door, or being near to the door or access panels, as detected by a motion sensor or light sensor. Nevertheless, the disclosure is not limited to the use of sensors and a trigger could also be produced by mechanical means, for example, a foot pedal.

An access door is generally a door or panel incorporated in, or integral to, the enclosure which can be opened to allow access to the interior of the enclosure. A door can be opened by any conventional means, for example, by swinging open, sliding open, an accordion-type access door or panel opening, etc. The size of the door or panel will necessarily vary in accordance with the size of the fomite and the access necessary to utilize the fomite. For example, for a door handle the opening will necessarily be large enough to accommodate the door handle and a hand of a user opening the door. For a point-of-sale terminal, an opening large enough to allow a user to use the point-of-sale terminal will necessarily be required. In embodiments therefore the size of the door or access panels will be at least large enough to accommodate a user's hand.

A door in an open position is any position which is not fully closed. A door in a closed position generally means the door is fully closed sealing or protecting the fomite from the outside environment. In embodiments, the door may be airtight, watertight, may include a clear or see-through material, for example a plastic polycarbonate, glass, or any other see-through material. In other embodiments the door or access panels may include metal or plastic or composite and may be light blocking.

The enclosure surrounding a fomite generally means that the enclosure or chamber completely encloses the fomite. In embodiments, the enclosure surrounds the fomite and provides an airtight or semi-airtight enclosure where air flow cannot easily pass from outside to the inside of the enclosure.

A UV light source is described above and can be any UV light source that can operate in the UV-C range. The UV light source will generally be able to produce a UV light intensity or power sufficient to kill germs, bacteria, virus, or other pathogens. The UV light power may range between 2,000 and 8,000 $\mu W \cdot s/cm^2$. See Ultraviolet germicidal irradiation, Wikipedia (en.wikipedia.org/wiki/Ultraviolet_germicidal_irradiation), Date of last revision: 20 Feb. 2021, herein incorporated by reference.

As mentioned above, the UV light source may preferably be an LED array capable of providing UV light in one or more frequency ranges optimized to kill germs, bacteria, viruses, and other pathogens. For example, a UV array may produce light at 265 nm, 220 nm, and/or 280 nm. In other embodiments, a UV array may produce light at 220 nm, 225 nm, 230 nm, 235 nm, 240 nm, 245 nm, 250 nm, 255 nm, 260 nm, 265 nm, 270 nm, 275 nm, and/or 280 nm.

Decontaminate as the term is used herein generally means the destruction or neutralization of bacteria or virus. In embodiments, 99% reduction of bacterial or virus is achieved in 5 seconds or less. In embodiments 99% reduction of bacteria or virus is achieved in 3 seconds or less. In embodiments 99% reduction of bacteria or virus is achieved in 1 second. In embodiments, 99.9% reduction of bacterial or virus is achieved in 5 seconds or less. In embodiments 99.9% reduction of bacteria or virus is achieved in 3 seconds or less. In embodiments 99.9% reduction of bacteria or virus is achieved in 1 second. In embodiments the virus is SARS-CoV or SARS-CoV-1 or variants including the alpha or delta variants. In embodiments 99.9% reduction of SARS-CoV or SARS-CoV-1 or variants including the alpha or delta variants is achieved in 1 second.

The decontamination can be of any relevant germ, bacteria, or virus, but is preferably a pathogen such as a virus, bacterium, protozoan, prion, viroid, or fungus that can produce disease in a mammal including a human. In one preferred embodiment the pathogen may be SARS-CoV or SARS-CoV-1 or variants including the alpha or delta variants. See e.g., Pathogen, Wikipedia (en.wikipedia.org/wiki/Pathogen), last edited 8 Jul. 2021, herein incorporated by reference.

Mounting stands are generally used to mount the UV light sources inside the enclosure or chamber. The mounting stands may be movable and may be capable of directing the dosage of UV light in different directions or at different angles inside the enclosure. Attaching or connecting the UV light sources to the mounting stands may be done by any conventional means including mechanical connections, screws, tacks, etc., or using adhesives.

Microprocessors as used herein can generally include any computer processor where data processing logic and control is included on a single integrated circuit, or a small number of integrated circuits. A microprocessor is generally a multipurpose, clock-driven, register-based, digital integrated circuit that accepts binary data as input, processes it according to instructions stored in its memory, and then provides results as output. Microprocessors as contemplated herein, will be capable of managing the sensors, drive system for opening the door or access panels, the UV light sources, as well as managing power sources including battery power.

While this disclosure includes specific examples, it will be apparent after an understanding of the disclosure of this application has been attained that various changes in form and details may be made in these examples without departing from the spirit and scope of the claims and their equivalents.

EXAMPLES

Example 1—COVID-19 Experiment

SARS-CoV-2 is the virus that causes COVID-19. To date, the current COVID-19 pandemic is responsible for more than 4.55 million deaths globally, of which over 645,000 wherein the United States.

Crystal IS (Green Island, NY) is an ISO 9001:2015 certified company that makes Klaran UVC LEDs and systems. IS initiated research with Boston University's National Emerging Infectious Diseases Laboratories (NEIDL) to understand how SARS-CoV-2 responds to ultraviolet light across the emission range of Klaran UVC LEDs (260 nm to 270 nm) and at different doses. Experiments were conducted using arrays of Klaran WD Series UVC LEDs at a distance of 7 cm from the test surface.

An array of Klaran UVC LEDs was used to irradiate a dried plastic surface containing SARS-CoV-2 at a distance of 7 cm.

Results show log reduction achieved from exposing the virus to a UVC intensity of 1.25 mW/cm$^2$ at different time intervals. A UVC dose of 6.25 mJ/cm$^2$ resulted in a 99.9% reduction of the virus (Table 1, below).

TABLE 1

Log Reduction as a function of Dose and LED Peak Wavelength.

| | UVC LED | | | |
|---|---|---|---|---|
| Wavelength | 1.25 mJ/cm$^2$ 1 sec. | 2.5 mJ/cm$^2$ 2 sec. | 3.75 mJ/cm$^2$ 3 sec. | 5 mJ/cm$^2$ 4 sec. |
| 260 nm | | | | 2.6 |
| 268 nm | 0.7 | 1.2 | 1.5 | 2.8 |
| 270 nm | | | | 2.8 |

The test was repeated using a dose of 5 mJ/cm$^2$ from LEDs of different peak wavelengths, representing both ends of the Klaran LED wavelength specification (260 nm and 270 nm). Results indicate similar efficacy across the tested wavelength range (Table 2, below). Comparing these results against published results from the University of Miyazaki (which used UVC LEDs emitting at 280 nm) highlights a marked dropin efficacy beyond 270 nm wavelength (see Inagaki et al. (2020) Rapid inactivation of SARS-CoV-2 with deep-UV LED irradiation, *Emerging Microbes & Infections*, 9(1): 1744-1747).

TABLE 2

Impact of Wavelength on Log Reduction.

| | UVC LED | | |
|---|---|---|---|
| Wavelength | 5 mJ/cm$^2$ | 6.25 mJ/cm$^2$ | 37 mJ/cm$^2$ |
| 268 nm | 2.8 | >3 | |
| 280 nm[1] | 0.9[1] | | 3.1[1] |

Conclusions

SARS-CoV-2 is a relatively weak virus that can be inactivated by low doses of UVC light. SARS-CoV-2 can be effectively inactivated in a matter of seconds through exposure to low doses of UVC light in the key germicidal range. Furthermore, UVC wavelength matters. Published results from the University of Miyazaki (which used UVC LEDs emitting at 280 nm) imply a marked drop in efficacy beyond 270 nm wavelength. Klaran UVC LEDs emit UVC light in the 260 nm to 270 nm wavelength range, which is the wavelength range that can achieve complete virus inactivation in a matter of seconds.

Example 2—MicroLumix Product Analysis and COVID-19

A simulation was conducted by Crystal IS of the efficacy of a germ decontamination apparatus according to an embodiment of the present invention against SARS-CoV-2. For a door handle, the minimum average intensity on all surfaces, including the back of the handle, was >6.25 mW/cm$^2$. Per the results of Example 1, this allows for a 99.9% SARS-CoV-2 reduction in 1 second.

The invention claimed is:

1. A portable germ decontamination apparatus adapted to decontaminate at least one fomite region of an object fixedly attached to a support structure, the apparatus comprising:
   a housing defining an interior enclosure;
   the housing including a rear housing portion and a front housing portion opposite the rear housing portion;
   the rear housing portion including a rear opening disposed therein, the rear opening being configured or designed to provide access to the interior enclosure;
   the housing being configured or designed to be attachable to the support structure in a first configuration which permits the entirety of the at least one fomite region to be exposed to the interior enclosure;
   the housing being further configured or designed to be attachable to the support structure according to the first configuration and in a manner which does not require moving or direct contact with the object;
   the front housing portion including a front opening configured or designed to provide access to the interior enclosure;
   a movable access door movably attached to the housing for preventing access to the interior enclosure via the front opening, the access door being configurable in a closed position which prevents access to the interior enclosure, the access door being further configurable in an open position which permits access to the interior enclosure;
   wherein the access door comprises a plurality of stackable access panels including a first access panel and a second access panel, the second access panel being movable into a first stacked configuration such that the second access panel is stacked either behind or in front of the first access panel;
   the first access panel including at least one first edge portion and a first body portion, the at least one first edge portion being different from the first body portion, the first body portion including a first curved body portion;
   the second access panel including at least one second edge portion and a second body portion, the at least one second edge portion being different from the second body portion, the second body portion including a second curved body portion;
   a drive mechanism for causing the access door to open or close in response to at least one triggering event;
   one or more ultraviolet light sources disposed at the interior enclosure and configured to decontaminate the at least one fomite region;
   one or more sensors configured to detect the at least one triggering event; and
   a controller configured to control the one or more sensors, the drive mechanism, and/or the one or more ultraviolet light sources.

2. The apparatus of claim 1:
   wherein the first and second access panels are configured in the first stacked configuration while the access door is configured in the open position; and
   wherein the first and second access panels are configured in a non-planar, stepped configuration while the access door is configured in the closed position.

3. The apparatus of claim 1 wherein the first and second access panels are movable into the first stacked configuration such that the second access panel is stacked either behind or in front of the first access panel.

4. The apparatus of claim 1:
   wherein the second curved body portion is movable into a second stacked configuration such that the second curved body portion is stacked either behind or in front of the first curved body portion.

5. The apparatus of claim 1:
   wherein the first access panel includes a first cylindrically-shaped panel portion;
   wherein the second access panel includes a second cylindrically-shaped panel portion; and
   wherein the second cylindrically-shaped panel portion is movable into a second stacked configuration such that the second cylindrically-shaped panel portion is stacked either behind or in front of the first cylindrically-shaped panel portion in a non-telescoping configuration.

6. The apparatus of claim 1, wherein the housing is configured or designed to envelope the at least one fomite region while the housing is attached to the support structure according to the first configuration, and while the access door is configured in the closed position.

7. The apparatus of claim 1, wherein the rear housing includes attachment means for fixedly attaching the housing to the support structure in a manner which causes the entirety of the at least one fomite region to be exposed, via the rear opening, to the interior enclosure.

8. The apparatus of claim 1, wherein the rear opening is configured or designed to enable the at least one fomite region to pass therethrough.

9. The apparatus of claim 1:
   wherein the object is a fixture fixedly attached to the support structure, and
   wherein the housing is configured or designed to be fixedly attachable to the support structure in a manner which causes the entirety of the at least one fomite region to be exposed to the interior enclosure via the rear opening.

10. The apparatus of claim 1 further comprising at least one portable power source for providing power to at least one electronic component of the portable germ decontamination apparatus.

11. The apparatus of claim 1, wherein the controller is configured or designed to execute a plurality of instructions for:

verifying that the access door is configured in the closed position; and initiating decontamination of the at least one fomite region in response to verifying that the access door is configured in the closed position.

12. The apparatus of claim 1, wherein the one or more sensors comprise an obstruction sensor, a motion sensor or detector, a light sensor, a sound sensor, and/or a heat or infrared sensor.

13. The apparatus of claim 1, wherein the controller is configured or designed to execute a plurality of instructions for:

implementing the decontamination of the at least one fomite region in a manner which causes inactivation of germ populations of the at least one fomite region by at least 99%.

14. The apparatus of claim 1, wherein the one or more ultraviolet light sources are configured or designed to produce UV-C radiation with a wavelength in the range of 200-280 nm.

15. The apparatus of claim 1, wherein the one or more ultraviolet light sources comprise light emitting diodes (LEDs), and wherein the LEDs comprise one or more semiconductor chips and/or one or more LED arrays.

16. The apparatus of claim 1, wherein one or more surfaces inside the interior enclosure are coated with a UV reflective coating.

17. The apparatus of claim 1, wherein the object corresponds to a fixture selected from a group consisting of: a door handle, a fixture comprising a restroom stall latch, a fixture comprising a deadbolt, a fixture comprising a gas pump handle, a fixture comprising a retail point of-sale (POS) terminal, an automatic teller machine, a fixture comprising a shopping cart handle, a fixture comprising an elevator control panel, a fixture comprising a telephone, a fixture comprising a paper towel extraction lever, a fixture comprising a toilet handle, and a fixture comprising a keyboard or keypad.

18. The apparatus of claim 1, wherein the housing is configured or designed to provide a substantially airtight interior enclosure while the housing is attached to the support structure via the first configuration, and while the access door is in the closed position.

19. The apparatus of claim 1 being further configured or designed to decontaminate all exposed fomite regions of the object while the housing is attached to the support structure via the first configuration, and while the access door is in the closed position.

20. The apparatus of claim 1, wherein the apparatus is configured or designed to prevent airborne pathogens from re-contaminating exposed surfaces of the object while the housing is attached to the support structure via the first configuration.

21. A portable germ decontamination apparatus adapted to decontaminate at least one fomite region of an object fixedly attached to a support structure, the apparatus comprising:

a housing defining an interior enclosure;

the housing including a rear housing portion and a front housing portion opposite the rear housing portion;

the rear housing portion including a rear opening disposed therein, the rear opening being configured or designed to provide access to the interior enclosure;

the housing being configured or designed to be attachable to the support structure in a first configuration which permits at least one fomite region to be exposed to the interior enclosure;

the housing being further configured or designed to be attachable to the support structure according to the first configuration and in a manner which does not require moving or direct contact with the object;

the front housing portion including a front opening configured or designed to provide access to the interior enclosure;

a movable access door movably attached to the housing for preventing access to the interior enclosure via the front opening, the access door being configurable in a closed position which prevents access to the interior enclosure, the access door being further configurable in an open position which permits access to the interior enclosure;

wherein the access door comprises a plurality of stackable access panels including a first access panel and a second access panel, the second access panel being movable into a first stacked configuration such that the second access panel is stacked either behind or in front of the first access panel;

the first access panel including at least one first edge portion and a first body portion, the at least one first edge portion being different from the first body portion, the first body portion including a first curved body portion;

the second access panel including at least one second edge portion and a second body portion, the at least one second edge portion being different from the second body portion, the second body portion including a second curved body portion;

a drive mechanism for causing the access door to open or close; and a first decontamination mechanism disposed at the interior enclosure and configured or designed to decontaminate the at least one fomite region.

22. The apparatus of claim 21:

wherein the access door comprises a plurality of stackable access panels including a first access panel and a second access panel, the first and second access panels being movable into a first stacked configuration such that the second access panel is stacked either behind or in front of the first access panel.

23. The apparatus of claim 21:

wherein the second curved body portion is movable into a second stacked configuration such that the second curved body portion is stacked either behind or in front of the first curved body portion.

24. The apparatus of claim 21:

wherein the first access panel includes a first cylindrically-shaped panel portion;

wherein the second access panel includes a second cylindrically-shaped panel portion; and wherein the second cylindrically-shaped panel portion is movable into a second stacked configuration such that the second cylindrically-shaped panel portion is stacked either behind or in front of the first cylindrically-shaped panel portion, in a non-telescoping configuration.

25. The apparatus of claim 21;

wherein the drive mechanism is response to at least one triggering event for causing the access door to open or close;

wherein the first decontamination mechanism includes a first ultraviolet light source;

wherein the apparatus further comprises one or more sensors configured to detect the at least one triggering event; and a controller configured to control the one or more sensors, the drive mechanism, and/or the one or more ultraviolet light sources.

26. The apparatus of claim 21:
wherein the object is a fixture fixedly attached to the support structure, and
wherein the housing is configured or designed to be fixedly attachable to the support structure in a manner which causes the entirety of the at least one fomite region to be exposed to the interior enclosure via the rear opening.

27. The apparatus of claim 21, wherein the apparatus is configured or designed to prevent airborne pathogens from re-contaminating the at least one fomite region while the housing assembly is attached to the support structure via the first configuration.

* * * * *